US010259888B2

(12) United States Patent
Michon et al.

(10) Patent No.: US 10,259,888 B2

(45) **Date of Patent: *Apr. 16, 2019**

(54) ANTIBODIES TARGETED TO FUNGAL CELL WALL POLYSACCHARIDES

(71) Applicant: Wellstat Vaccines, LLC, Rockville, MD (US)

(72) Inventors: Francis Michon, Bethesda, MD (US); Samuel J. Wohlstadter, Madison, VA (US); Frank Comer, Gaithersburg, MD (US); Kuishu Ren, Columbia, MD (US)

(73) Assignee: Wellstat Vaccines, LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/583,396

(22) Filed: May 1, 2017

(65) Prior Publication Data

US 2018/0251573 A1 Sep. 6, 2018

Related U.S. Application Data

(63) Continuation of application No. 14/771,923, filed as application No. PCT/US2014/021128 on Mar. 6, 2014, now abandoned.

(60) Provisional application No. 61/777,631, filed on Mar. 12, 2013.

(51) Int. Cl.

| | |
|---|---|
| ***A61K 39/385*** | (2006.01) |
| ***C07K 16/14*** | (2006.01) |
| ***C08B 37/08*** | (2006.01) |
| ***A61K 39/00*** | (2006.01) |
| ***A61K 47/64*** | (2017.01) |

(52) U.S. Cl.

CPC ........ *C08B 37/003* (2013.01); *A61K 39/0002* (2013.01); *A61K 39/385* (2013.01); *A61K 47/646* (2017.08); *A61K 47/6415* (2017.08); *C07K 16/14* (2013.01); *A61K 2039/6031* (2013.01); *A61K 2039/6037* (2013.01); *A61K 2039/627* (2013.01)

(58) Field of Classification Search

None

See application file for complete search history.

(56) References Cited

U.S. PATENT DOCUMENTS

| | | | |
|---|---|---|---|
| 4,804,750 | A | 2/1989 | Nishimura et al. |
| 5,312,908 | A | 5/1994 | Nakao |
| 5,705,634 | A | 1/1998 | Bredehorst et al. |
| 6,602,508 | B2 | 8/2003 | Michon et al. |
| 7,824,688 | B2 | 11/2010 | Cassone et al. |
| 9,480,748 | B2 | 11/2016 | Saint-Lu et al. |
| 2008/0311595 | A1 | 12/2008 | Mattsby-Baltzer |
| 2009/0232831 | A1 | 9/2009 | Wong et al. |
| 2009/0281058 | A1 | 11/2009 | Gislason et al. |
| 2011/0150880 | A1 | 6/2011 | Pier et al. |
| 2016/0017062 | A1* | 1/2016 | Michon ............. A61K 39/0002 424/137.1 |

FOREIGN PATENT DOCUMENTS

| | | | |
|---|---|---|---|
| EP | 1506009 | B1 | 5/2008 |
| JP | 3-163092 | H | 7/1991 |
| JP | 7-2679 | H | 1/1995 |
| JP | 2010280654 | A | 12/2010 |
| JP | 2012506922 | A | 3/2012 |
| JP | 2012241084 | A | 12/2012 |
| WO | 2003042250 | A1 | 5/2003 |
| WO | 2006096970 | A1 | 9/2006 |
| WO | 2010015022 | A1 | 2/2010 |
| WO | 2010026239 | A1 | 3/2010 |
| WO | 2010048244 | A1 | 4/2010 |
| WO | 2011080595 | A2 | 7/2011 |

OTHER PUBLICATIONS

Cutler et al., "Advances in combating fungal diseases: vaccines on the threshold", Nat. Rev. Microbiol. (2007). 5: 13-28.

Ostrosky-Zeichner et al., "An insight into the antifungal pipeline: selected new molecules and beyond", Nat. Rev. Drug Discov. (2010). 9: 719-727.

Pfaller et al., "Epidemiology of invasive candidiasis: a persistent public health problem", Clin. Microbiol. Rev. (Jan. 2007). 20(1): 133-163.

Casadevall et al., "Antibody-mediated protection through cross-reactivity introduces a fungal heresy into immunological dogma", Infect. Immunity. (Nov. 2007). 75(11): 5074-5078.

Spellberg, "Prospects for and barriers to a fungal vaccine", Expert Opin. Biol. Ther. (2007). 7(12): 1785-1788.

Cassone et al., "Opportunistic fungi and fungal infections: the challenge of a single, general antifungal vaccine", Expert Rev. Vaccines (2006). 5(6): 859-867.

Torosantucci et al., "A novel glyco-conjugate vacccine against fungal pathogens", J. Exp. Med. (2005). 202: 597-606.

Xin et al., "Synthetic glycoeptide vacccines combining [beta]-mannan and peptide epitopes induce protection against candidiasis", PNAS (Sep. 9, 2008). 105(36): 13526-13531 and 9 pages Supporting Information.

Han et al., "Antibody response that protects against disseminated candidiasis", Infect. Immunity (Jul. 1995). 63(7): 2714-2719.

Rachini et al., "An anti-[beta]-glucan monoclonal antibody inhibits growth and capsule formation of Cryptococcus neoformans in vitro and exerts therapeutic, anticryptococcal activity in vivo", Infect. Immunity (Nov. 2007). 75(11): 5085-5094.

(Continued)

*Primary Examiner* — Padmavathi Baskar

(74) *Attorney, Agent, or Firm* — Lewis J. Kreisler

(57) ABSTRACT

A compound comprising one or more polysaccharide moieties each independently represented by the formula $\beta(1\rightarrow4)$-[GlcNH—R]$_n$-2,5-anhydromannose, wherein n is a positive integer from 3 to 500, and R is H or an acyl group, is described. The compound can be manufactured by (a) reacting chitosan with an acylating agent sufficient to partially N-acylate the chitosan, yielding a modified chitin/chitosan mixed polymer; and (b) reacting the modified chitin/chitosan mixed polymer with a deaminating agent to cleave the mixed polymer at the unacylated chitosan moieties. The compound can be used to immunize against fungal infection. Antibodies specific to the compound, and the use of such antibodies to protect against fungal infection are also described.

19 Claims, 46 Drawing Sheets

(56) References Cited

OTHER PUBLICATIONS

Lenardon et al., "Chitin synthesis and fungal pathogenesis", Current Opin. Microbiol. (2010). 13: 416-423.
Baker et al., "Chitosan, the deacetylated form of chitin, is necessary for cell wall integrity in Cryptococcus neoformans", Eukaryotic Cell (May 2007). 6(5): 855-867.
Latge, "The cell wall: a carbohydrate armour for the fungal cell", Mol. Microbiol. (2007). 66(2): 279-290.
Levitz, "Innate recognition of fungal cell walls", PLos Pathog. (Apr. 2010). 6(4): e1000758 (3 pages).
Shibata et al., "Alveolar macrophage priming by intravenous administration of chitin particles, polymers of N-acetyl-D-glucosamine, in mice", Infection and Immunity (May 1997). 65(5): 1734-1741.
Shibata et al., "Th1 adjuvant N-acetyl-D-glucosamine polymer up-regulates Th1 immunity but down-regulates Th2 immunity against a mycobacterial protein (MPB-59) in interleukin-10-knockout and wild-type mice", Infection and Immunity (Oct. 2001). 69(10): 6123-6130.
Sendid et al., "Antibodies against glucan, chitin, and *Saccharomyces cerevisiae* mannan as new biomarkers of Candida albicans infection that complement tests based on C. albicans mannan", Clin. and Vaccine Immunol. (Dec. 2008). 15(12): 1868-1877.
Lee, "Chitin, chitinases and chitinase-like proteins in allergic inflammation and tissue remodeling", Yonsei Med. J. (2009). 50(1): 22-30.
Limam et al., "Extraction and characterization of chitin and chitosan from crustacean by-products: Biological and physicochemical properties", African J. Biotech. (Jan. 2011). 10(4): 640-647.
New England Biolabs catalog (2011), Catalog # S6654S: Anti-chitin binding domain serum.
Baaten et al., "Nasal mucosal administration of chitin microparticles boosts innate immunity against influenza A virus in the local pulmonary tissue", Vaccine (2010). 28: 4130-4137.
Hamajima et al., "Chitin micro-particles (CMP): A useful adjuvant for inducing viral specific immunity when delivered intranasally with an HIV-DNA vaccine", Viral Immunology (2003). 16(4): 541-547.
Sorlier et al., "Preparation and development of anti-chitosan antibodies", J. Biomed. Materials Res. Part A. 67(3): 766-774. 2003.
Bromuro et al., "Beta-glucan-CRM197 conjugates as candidates antifungal vaccines", Vaccine. 28: 2615-2623. 2010.
Minke et al., "The structure of [alpha]-chitin", J. Mol. Biol. 120: 167-181. 1978.
Ballou, "Yeast cell wall and cell surface" in The molecular biology of the yeast *Saccharomyces*. Metabolism and gene expression. pp. 335-360 (Strathern et al. eds., Cold Spring Harbor Laboratory Press 1982).
Cassone et al., "Immunological Moieties of the cell well" in Candida albicans. pp. 89-107 (Prasad ed., Springer-Verlag 1991).
Bulawa, "Attenuated virulence of chitin-deficient mutants of Candida albicans", Proc. Nat'l Acad. Sci. USA. 92: 10570-10574. Nov. 1995.
Rementeria et al., "Resistance to candidiasis and macrophage activity in chitin-treated mice", FEMS Immunol. Med. Microbiol. 19: 223-230. 1997.
Martinez et al., "Serologic response to cell wall mannoproteins and proteinns of Candida albicans", Clin. Microbiol. Rev. 11(1): 121-141. 1998.
Uchiyama et al., "Solubilized cell wall [beta]-glucan, CSBG, is an epitope of Candida immune mice", Biol. Pharm. Bull. 23(5): 672-676. 2000.
Bromuro, "Interplay between protective and inhibitory antibodies dictates the outcome of experimentally disseminated Candidasis in recipients of a Candida albicans vaccine", Infect. Immunol. 70(10): 5462-5470. Oct. 2002.
Masuoka, "Surface glycans of Candida albicans and other pathogenic fungi: Physiological roles, clinical uses, and experimental challenges", Clin. Microbiol. Rev. 17(2): 281-310. Apr. 2004.
Sendid, "Antibodies against glucan, chitin, and *Saccharomyces cerevisiae* mannan as new biomarkers of Candida albicans infection that complement tests based on C. albicans mannan." Clin. and Vaccine Immunol. 15(12): 1868-1877. Dec. 2008.
Torosantucci, "Protection by Anti-[beta]-glucan antibodies is associated with restricted [beta]-1,3 glucan binding specificity and inhibition of fungal growth and adherence", PloS one. 4(4): e5392 (17 pages). Apr. 2009.
De Jonge et al., "Conserved fungal LysM Effector Ecp6 Prevents Chitin-Triggered Immunity in Plants", Science. 329(5994): 953-955. Aug. 2010.

* cited by examiner

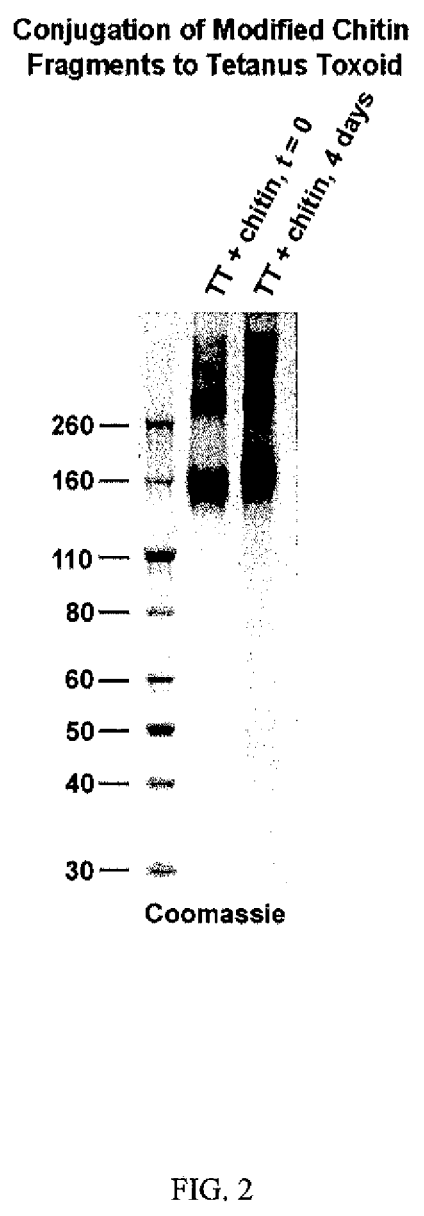

Conjugation of Modified Chitin Fragments to Tetanus Toxoid

TT + chitin, t = 0
TT + chitin, 4 days

260 —
160 —
110 —
80 —
60 —
50 —
40 —
30 —

Coomassie

FIG. 2

Immunization Schedule:

| | Group 1 | Group 2 | Group 3 | Group 4 |
|---|---|---|---|---|
| **Day -4** | **Collect pre-immune serum from each group** | | | |
| **Day 0** | PBS + Complete Freund's Adjuvant (CFA) i.p. 200 μL | Modified Chitin-TT conjugate + CFA 25 μg/injection i.p. 200 μL | Modified Chitin-TT conjugate + CFA 50 μg/injection i.p. 200 μL | Modified Chitin-TT conjugate + CFA 100 μg/injection i.p. 200 μL |
| **Day 28** | PBS + Incomplete Freund's Adjuvant (IFA) i.p. 200 μL | Modified Chitin-TT conjugate + IFA 25 μg/injection i.p. 200 μL | Modified Chitin-TT conjugate + IFA 50 μg/injection i.p. 200 μL | Modified Chitin-TT conjugate + IFA 100 μg/injection i.p. 200 μL |
| **Day 38** | **Collect serum from each group** | | | |
| | PBS + Incomplete Freund's Adjuvant (IFA) i.p. 200 μL | Modified Chitin-TT conjugate + IFA 25 μg/injection i.p. 200 μL | Modified Chitin-TT conjugate + IFA 50 μg/injection i.p. 200 μL | Modified Chitin-TT conjugate + IFA 100 μg/injection i.p. 200 μL |
| **Day 50** | **Collect serum from each group** | | | |

FIG. 3

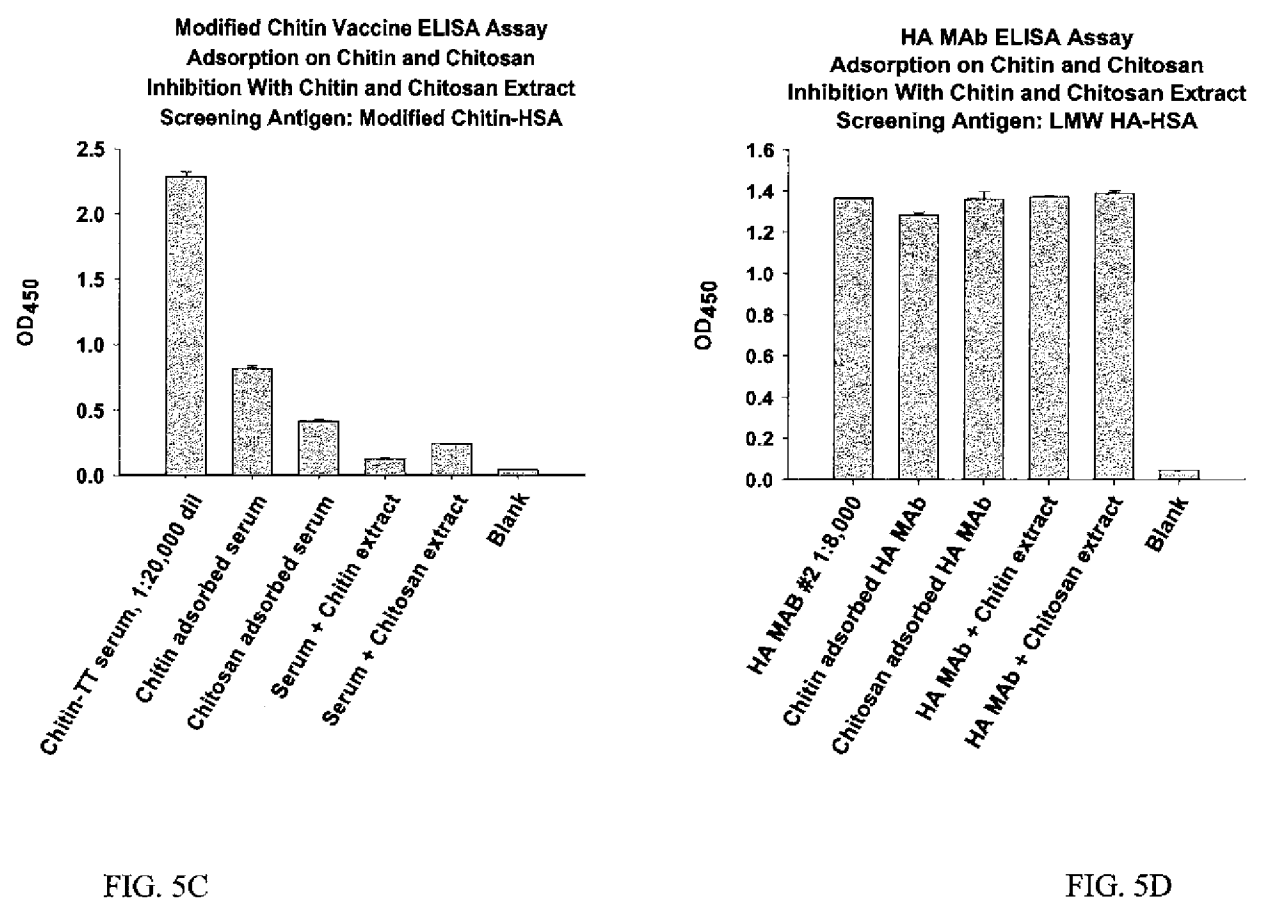

Modified Chitin Vaccine ELISA Assay
Adsorption on Chitin and Chitosan
Inhibition With Chitin and Chitosan Extract
Screening Antigen: Modified Chitin-HSA

OD450

2.5
2.0
1.5
1.0
0.5
0.0

Chitin-TT serum, 1:20,000 dil
Chitin adsorbed serum
Chitosan adsorbed serum
Serum + Chitin extract
Serum + Chitosan extract
Blank

FIG. 5C

HA MAb ELISA Assay
Adsorption on Chitin and Chitosan
Inhibition With Chitin and Chitosan Extract
Screening Antigen: LMW HA-HSA

OD450

1.6
1.4
1.2
1.0
0.8
0.6
0.4
0.2
0.0

HA MAB #2 1:8,000
Chitin adsorbed HA MAb
Chitosan adsorbed HA MAb
HA MAb + Chitin extract
HA MAb + Chitosan extract
Blank

FIG. 5D

Assay Controls

Gating Strategy

Positive Controls-Rabbit Polyclonal antibody to candida

Positive Controls-Rabbit Polyclonal antibody to candida

Positive Controls-Rabbit Polyclonal antibody to candida

Tetanus toxoid (GCMP-TT) Negative Controls

Tetanus toxoid (GCMP-TT) Negative Controls mChitin-TT mChitin-TT mChitin-TT mChitin-TT mChitin-TT mChitin-TT

Laminarin-TT Group

Laminarin-TT Group

O/N 30 C, YPD

Laminarin-TT Group

Laminarin-TT Group

Laminarin-TT Group

300 Min, 37 C, YPD+Serum

1:10 dilution

Laminarin-TT Group mChitin TT Group

O/N 30 C, YPD

1:50 dilution mChitin TT Group

300 Min, 37 C, YPD+Serum

1:50 dilution

Human Sera (12062-12072) on Modified Chitin-HSA Coated Plate

Inhibition of Human Serum (12017) with Different Inhibitors on Modified Chitin-HSA Coated Plate

Human Sera Inhibition with Oligo-GlcNAc on

Chito-Hexa-(GlcNAc)6-HSA Coated Plate

Human Sera IgG(γ) on Laminarin-HSA Coated Plate

Cryptococcus neoformans Type A (H99) FACS Binding Assay

Cryptococcus neoformans Type A (H99) FACS Binding Assay

Cryptococcus neoformans Type A (H99) FACS Binding Assay

Cryptococcus neoformans Type A (H99) FACS Binding Assay

Cryptococcus neoformans Type A (H99) FACS Binding Assay

Cryptococcus neoformans Type A (H99) FACS Binding Assay

ANTIBODIES TARGETED TO FUNGAL CELL WALL POLYSACCHARIDES

BACKGROUND OF THE INVENTION

A dramatic rise in the incidence of invasive fungal disease in recent years, as well as the emergence of drug resistant and previously rare fungal species, has highlighted the need for broadly effective new therapeutic and prophylactic antifungal treatment strategies (3-5). The increased incidence of invasive fungal infection is partly attributable to an increase in the immunocompromised patient population, owing to the growing number of patients with disease associated acquired immunodeficiencies, those in critical care units, patients undergoing surgery or immunosuppressive treatment, and those receiving organ or cellular transplant therapies. Importantly, the risk factors that predispose individuals to invasive fungal disease do not preclude the possibility of mounting an effective immune response and responding favorably to immunotherapy (6, 7), giving promise to the development of effective vaccine or immunotherapy based approaches to meet this underserved medical need.

The two most prevalent pathogenic fungi affecting humans, *Aspergillus* and *Candida* spp., account for an estimated 8-10% of all health care acquired infections, with an attributable mortality of 30-40% (5, 8). *Candida* species are the fourth leading cause of nosocomial sepsis cases in the US and the rising incidence of invasive fungal disease from all pathogenic fungi represents a significant healthcare burden worldwide. Excess healthcare costs due to increased length of stay and treatment of hospital acquired fungal infections are in the range of US$ 1 thousand million annually in the US alone. Furthermore, comprehensive antifungal susceptibility testing of clinical isolates has made it evident that, despite advances in safe and effective antifungal drugs, all classes of currently available antifungal agents are subject to the emergence of resistant strains (5). Cryptococcal meningitis, an infection with the fungus *Cryptococcus* also known as cryptococcosis, is a very serious opportunistic infection among people with advanced HIV/AIDS. Cryptococcosis is not contagious, meaning it cannot spread from person-to-person. Cryptococcal meningitis specifically occurs after *Cryptococcus* has spread from the lungs to the brain. A global problem, worldwide, approximately 1 million new cases of cryptococcal meningitis occur each year, resulting in 625,000 deaths. Most cases are opportunistic infections that occur among people with HIV/AIDS. Although the widespread availability of antiretroviral therapy (ART) in developed countries has helped reduce cryptococcal infections in these areas, it is still a major problem in developing countries where access to healthcare is limited. Throughout much of sub-Saharan Africa, for example, *Cryptococcus* is now the most common cause of adult meningitis. Cryptococcal meningitis is one of the leading causes of death in HIV/AIDS patients; in sub-Saharan Africa, it may kill as many people each year as tuberculosis.(24).

These significant challenges of combating fungal disease point to the critical need for a highly effective pan-fungal vaccine as a valuable component of the anti-fungal arsenal. To date, two fungal cell wall carbohydrate components, β-mannan and β-glucan, have been explored as targets for anti-fungal vaccination. Conjugate vaccines composed of either linear β-(1→3)-glucan or β-(1→2)-mannotriose have been shown to confer protection against fungal disease, with efficacy in both active and passive immunization (9-11). In animal models of fungal disease, the β-glucan vaccine proved effective against *C. albicans, A. fumigatus*, and *C. neoformans*, validating the possibility of successful vaccination against multiple, disparate fungal pathogens (9, 12). Nevertheless, the production of effective vaccine responses requires careful consideration of the fine structure of the target antigens, as there is mounting evidence that one mechanism of immune evasion employed by fungal pathogens is the expression of immunodominant epitopes that induce non-protective or inhibitory antibody responses. These decoy epitopes ablate the efficacy of responses toward protective epitopes. For example, vaccines composed of linear β-(1→3)-glucan epitopes produce protective responses, while vaccines composed of β-(1→3)-glucans with β-(1→6)-glucan branches produce antibodies to both structures but do not confer protection against fungal disease (13, 14).

Moreover, the fundamental utility of the vaccine is dependent on the universality of target antigens. For example, the β-(1→2)-mannotriose epitope does not appear in all *Candida* species and the vaccine antigen employing this epitope relies on protective peptide epitopes to expand its utility (10). Considering the limited distribution of some cell wall carbohydrate epitopes and in view of the mechanisms employed by fungal pathogens to avoid productive immune responses to cell wall components, there is a need for a universally effective fungal vaccine. This invention is designed to target highly conserved fungal cell wall carbohydrate epitopes in order to provide a pan-fungal vaccine.

Chitin has not been examined as an antifungal vaccine target, largely for reasons related to its highly insoluble nature. Methods available in the art for degrading chitin into soluble fragments are not stoichiometrically controlled and it is thus difficult to modulate the degree of depolymerization.

SUMMARY OF THE INVENTION

This invention provides a compound comprising one or more polysaccharide moieties each independently represented by the formula β(1→4)-[GlcNH—R]$_n$-2,5-anhydromannose, wherein n is a positive integer from 3 to 500, and R is H or an acyl group.

This invention also provides a process for manufacturing a compound represented by the formula β(1→4)-[GlcNH—R]$_n$-2,5-anhydromannose, wherein n is a positive integer from 3 to 500, comprising:

(a) reacting chitosan with an amount of an acylating agent sufficient to partially N-acylate the chitosan, yielding a modified chitin/chitosan mixed polymer;

(b) reacting the modified chitin/chitosan mixed polymer with a deaminating agent to cleave the mixed polymer at the unacylated chitosan moieties, yielding the compound of formula β(1→4)-[GlcNH—R]$_n$-2,5-anhydromannose.

This invention provides a method of immunizing a mammalian subject against a fungal infection or pathogen, comprising administering to the subject an immunogenic amount of the compound or a composition containing it. This invention provides a method of stimulating an immune response in a mammalian subject against a fungal pathogen, comprising administering to the subject an immunogenic amount of the compound or a composition containing it. This invention also provides an antibody specific to the compound described above. And it provides a method of protecting a mammalian subject against a fungal infection or pathogen, comprising administering the antibody to the subject in an amount effective to protect the subject against the fungal infection.

Reaction scheme for the one pot preparation of modified chitin fragments from chitosan.

FIG. 2: Analysis of modified chitin conjugation to tetanus toxoid.

Coomassie Blue stained SDS-PAGE gel showing conjugation of modified chitin fragments to tetanus toxoid (TT) protein.

FIG. 3: Dose and immunization schedule modified chitin-TT conjugate.

Chart showing dose and immunization schedule for administration of modified chitin-TT conjugate vaccine to Balb/C mice.

Figure 4:
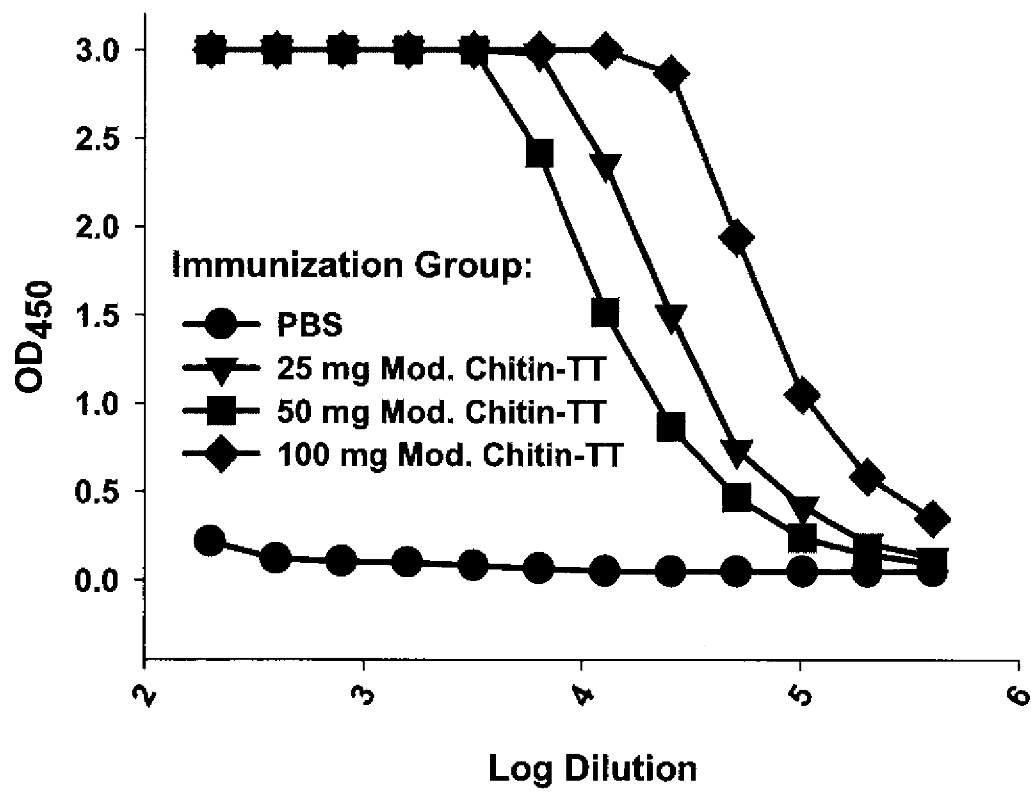

FIG. 4: Immunogenicity of modified chitin-TT conjugate vaccine in Balb/C mice.

Line plot showing immunogenicity of modified chitin-TT vaccine conjugate in Balb/C mice. The screening antigen was modified chitin cross linked to human serum albumin (HSA).

Figure 5A:
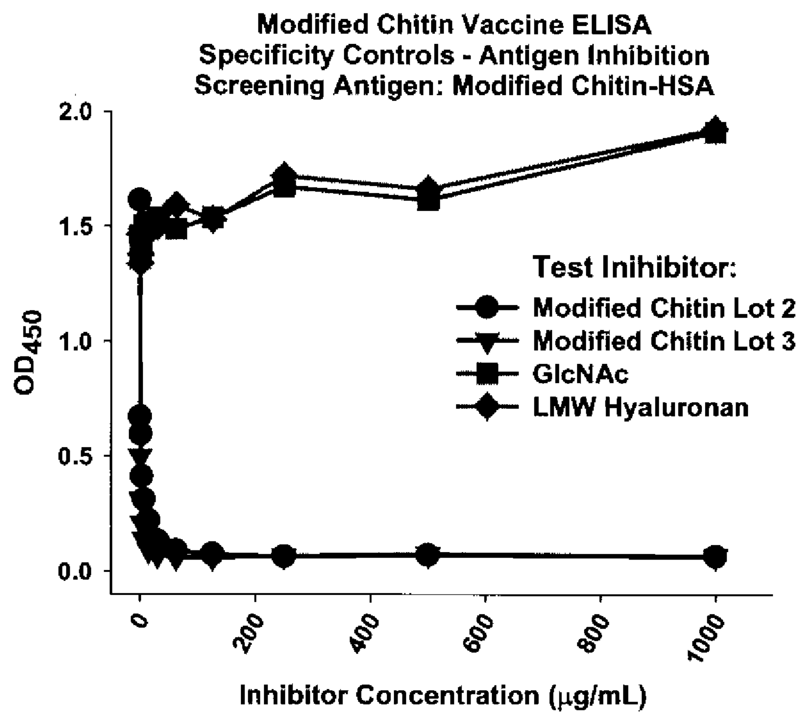

FIG. 5A: Specificity of immune response in Balb/C mice immunized with modified chitin-TT vaccine conjugate.

Line plot comparing inhibition of vaccine serum binding to modified chitin-HSA screening antigen.

Figure 5B:
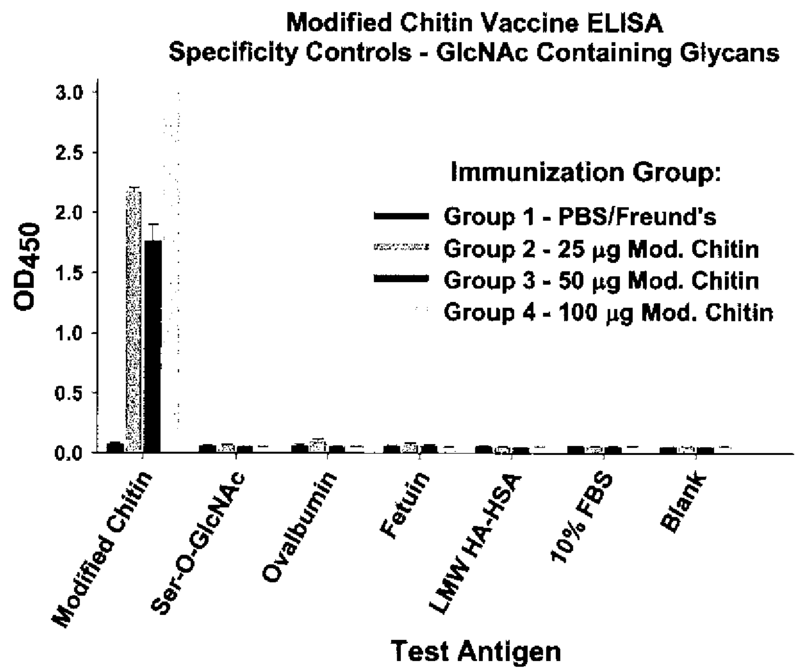

FIG. 5B: Specificity of immune response in Balb/C mice immunized with modified chitin-TT vaccine conjugate.

Bar graph showing lack of cross reactivity of vaccine sera toward multiple GlcNAc containing glyconjugates.

FIG. 5C: Specificity of immune response in Balb/C mice immunized with modified chitin-TT vaccine conjugate.

Bar graph showing reactivity of vaccine sera toward chitin/chitosan polysaccharides. The graph shows that antibodies reactive toward modified chitin can be depleted by adsorption on particulate chitin or chitosan. In addition, soluble extracts from chitin or chitosan inhibit binding of vaccine sera to modified chitin-HSA.

FIG. 5D: Specificity of immune response in Balb/C mice immunized with modified chitin-TT vaccine conjugate.

Bar graph showing reactivity of vaccine sera toward chitin/chitosan polysaccharides.

The graph shows that binding of an irrelevant antibody (anti-HA) to its epitope is unaffected by the same treatments.

Figure 6A:
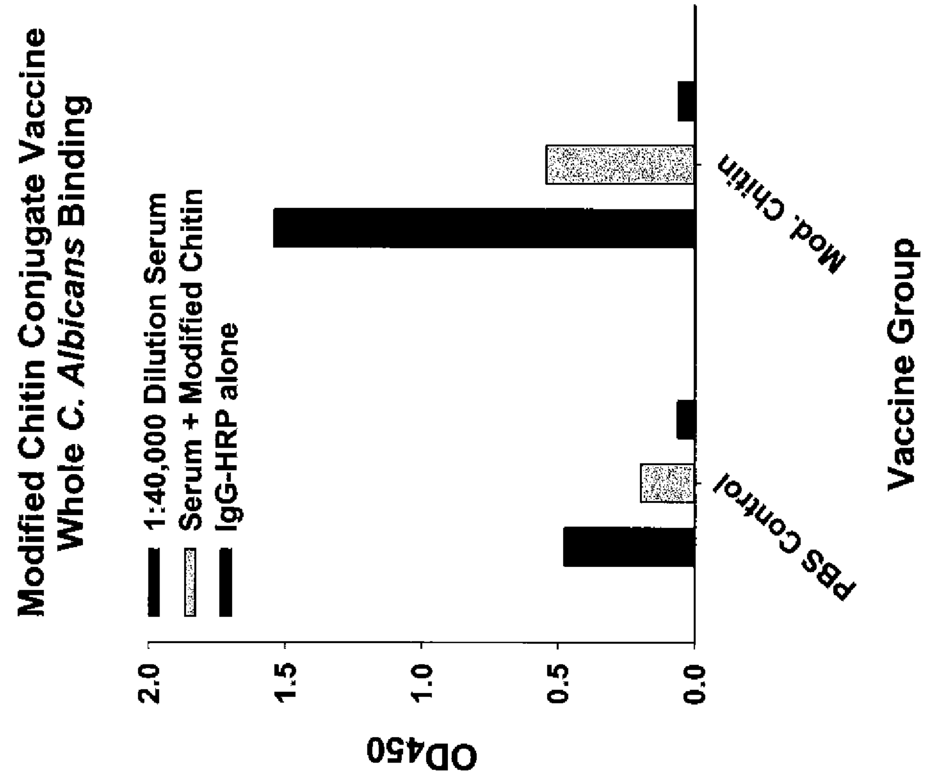

FIG. 6A: Binding of modified chitin-TT conjugate vaccine induced antibodies to whole *Candida albicans* fungi.

Bar graph showing that serum antibodies from mock (PBS) and modified chitin-TT immunized Balb/C mice bind to whole *C. albicans*. Reactivity is specifically competed away with modified chitin fragments.

Figure 6B:
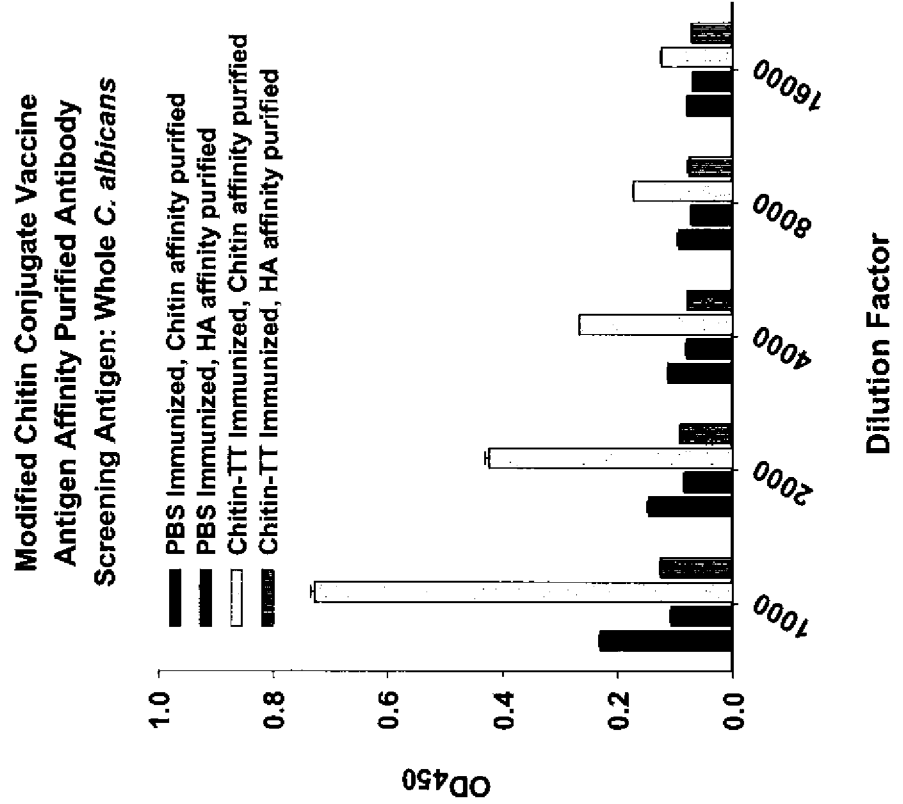

FIG. 6B: Binding of modified chitin-TT conjugate vaccine induced antibodies to whole *Candida albicans* fungi.

Bar graph showing that antigen affinity purified chitin reactive antibodies bind to whole *C. albicans.*

Figure 7B:
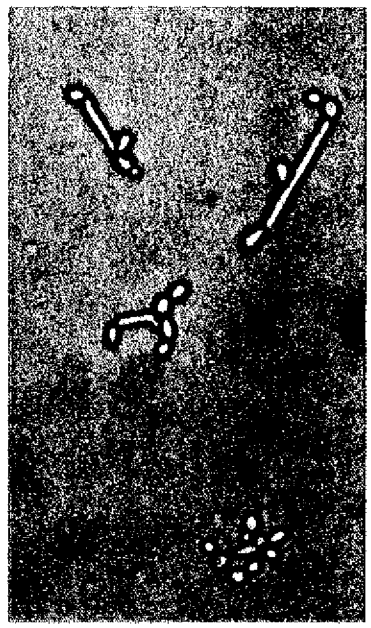
Figure 7A:
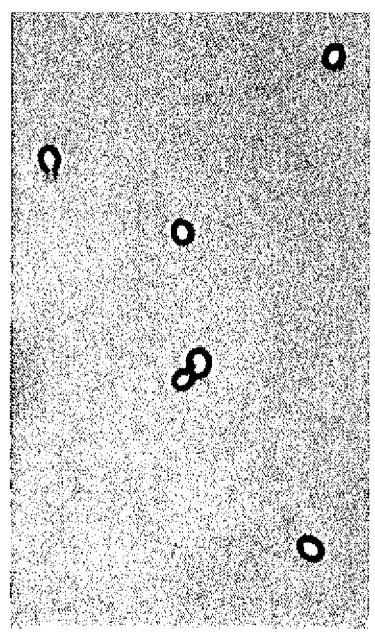

FIG. 7A: Morphology of *Candida albicans* yeast cells grown under various conditions Yeast cells grown at 30 C in YPD medium o/n.

FIG. 7B: Morphology of *Candida albicans* yeast cells grown under various conditions Intermediate filaments cells grown at 37 C in YPD medium and serum for 150 min.

Figure 7C:
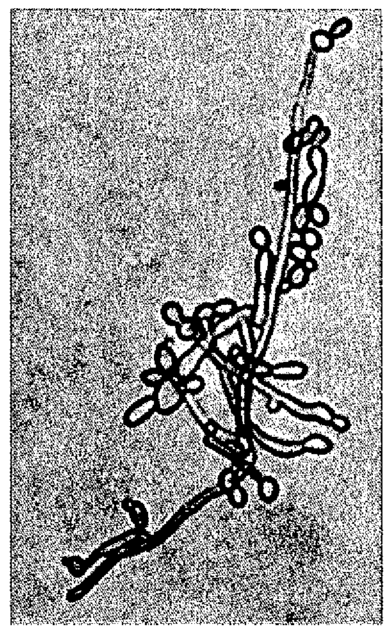

FIG. 7C: Morphology of *Candida albicans* yeast cells grown under various conditions Filaments grown into mycelia at 37 C in YPD medium and serum for 300 min.

Figure 8A:
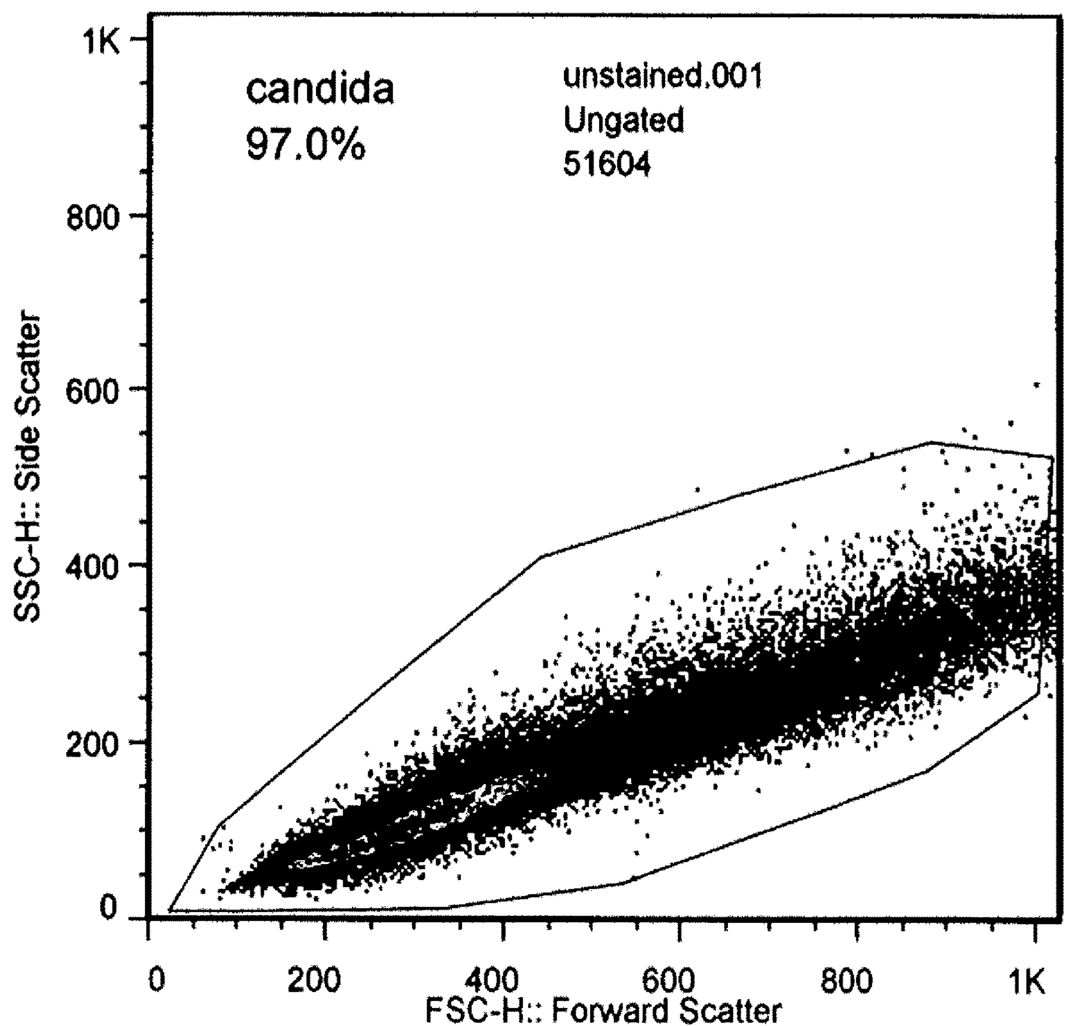

FIG. 8A: Binding of modified chitin and laminarin vaccine-induced antibodies to whole *Candida albicans* by flow cytometry.

Assay control (gating strategy) for antibody binding to yeast cells.

Figure 8B:
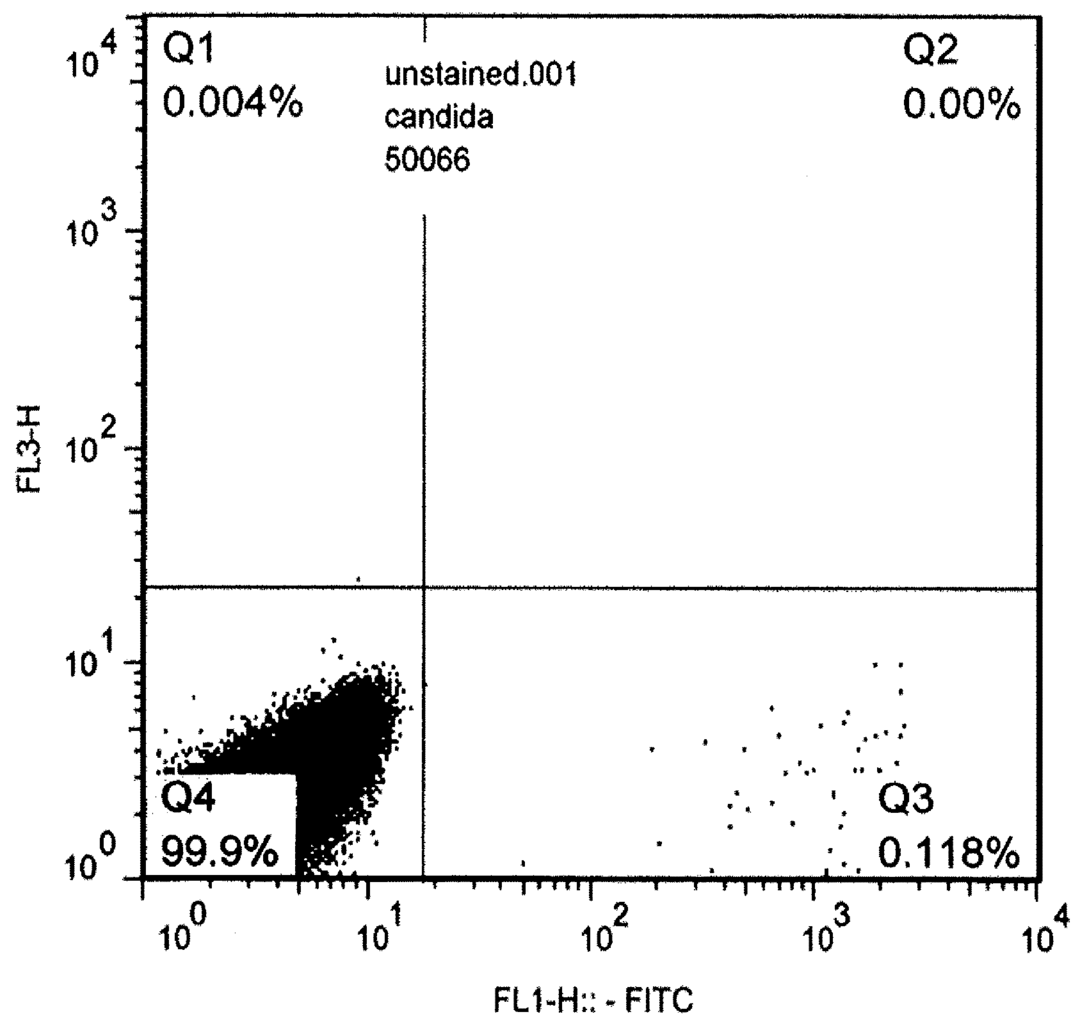

FIG. 8B: Binding of modified chitin and laminarin vaccine-induced antibodies to whole *Candida albicans* by flow cytometry.

Assay controls (unstained control) for antibody binding to yeast cells.

Figure 8C:
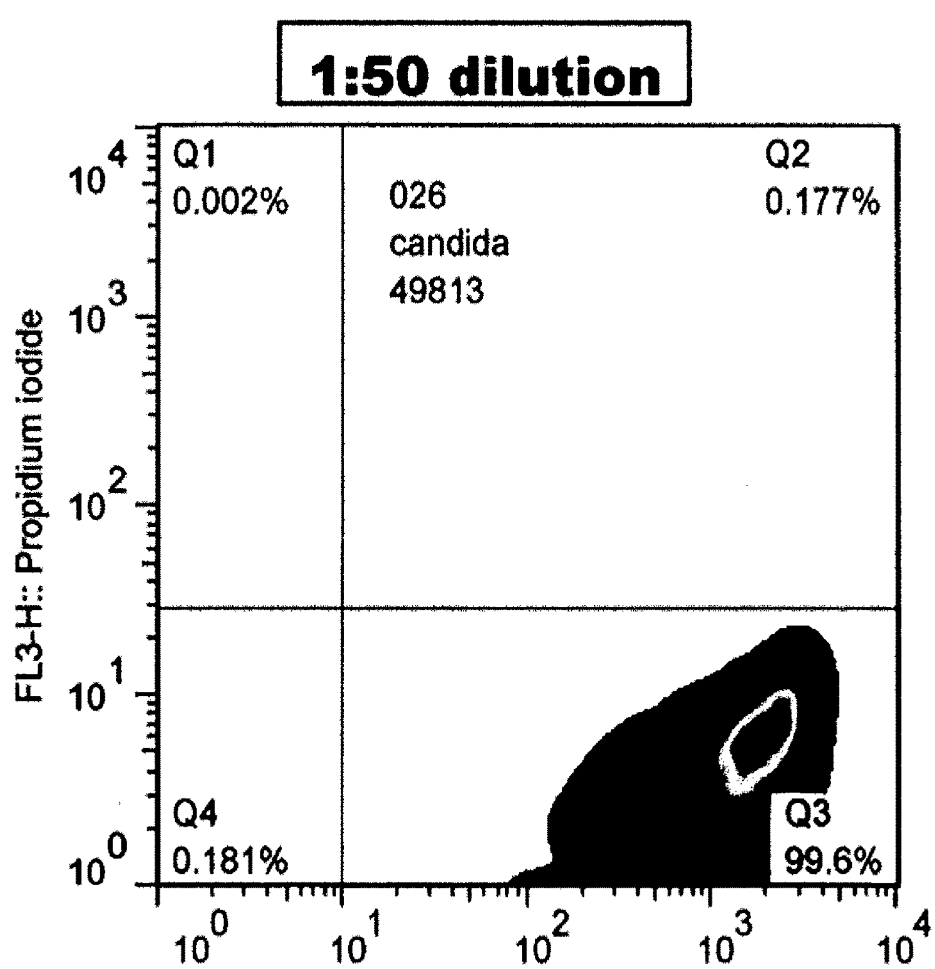

FIG. 8C: Binding of modified chitin and laminarin vaccine-induced antibodies to whole *Candida albicans* by flow cytometry.

Positive assay control (rabbit polyclonal antibody to *candida*) for antibody binding to yeast cells (1:50 dilution).

Figure 8D:
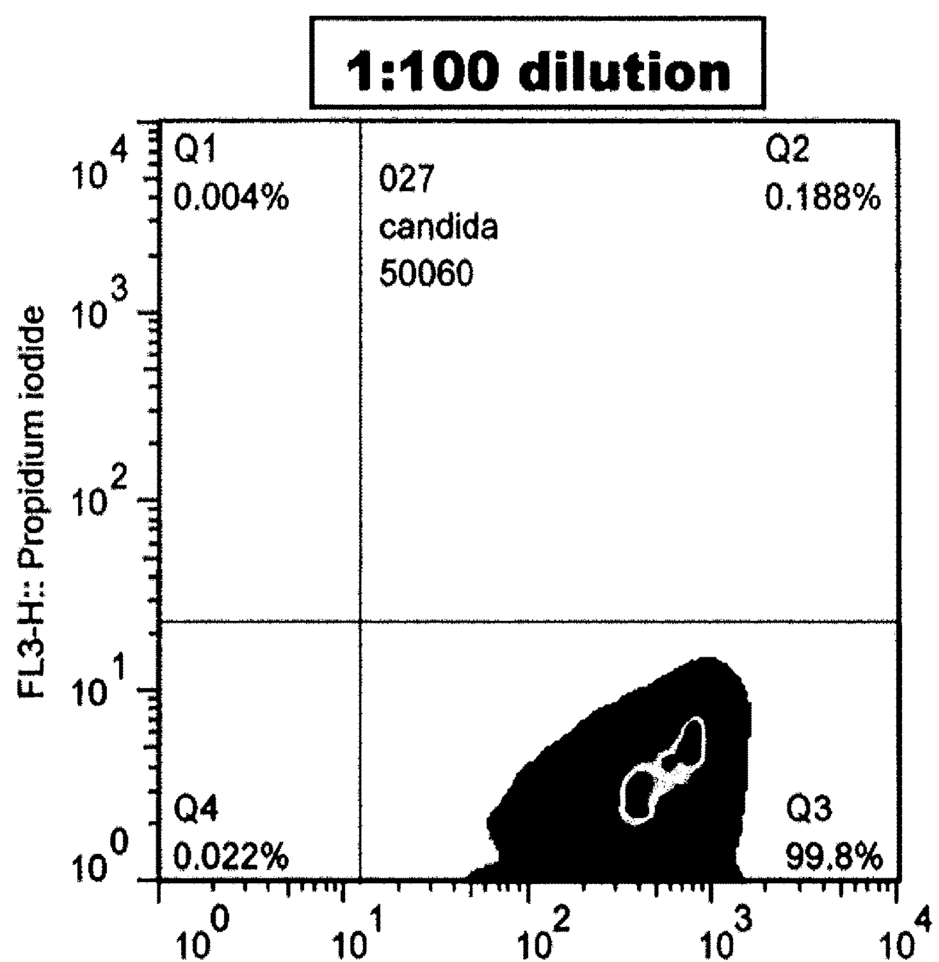

FIG. 8D: Binding of modified chitin and laminarin vaccine-induced antibodies to whole *Candida albicans* by flow cytometry.

Positive assay control (rabbit polyclonal antibody to *candida*) for antibody binding to yeast cells (1:100 dilution).

Figure 8E:
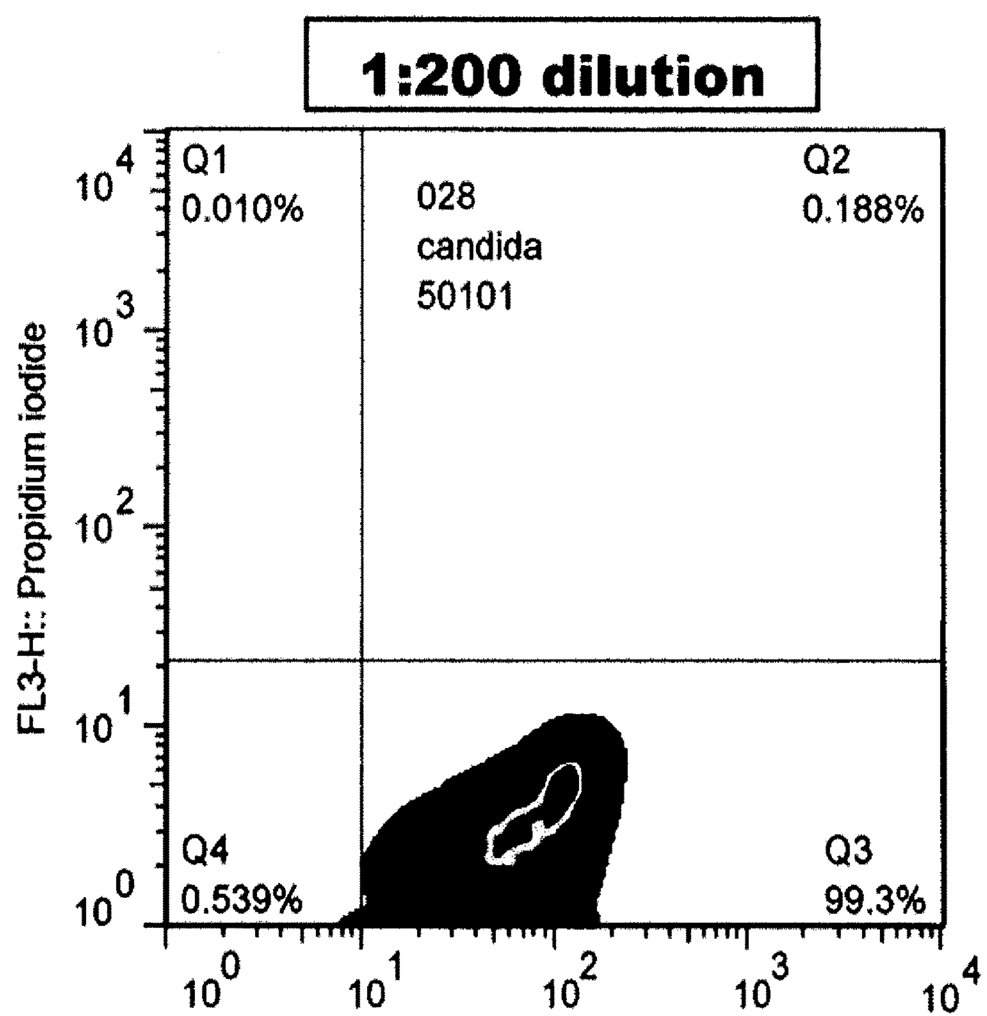

FIG. 8E: Binding of modified chitin and laminarin vaccine-induced antibodies to whole *Candida albicans* by flow cytometry.

Positive assays control (rabbit polyclonal antibody to *candida*) for antibody binding to yeast cells 1:200 dilution.

Figure 9A:
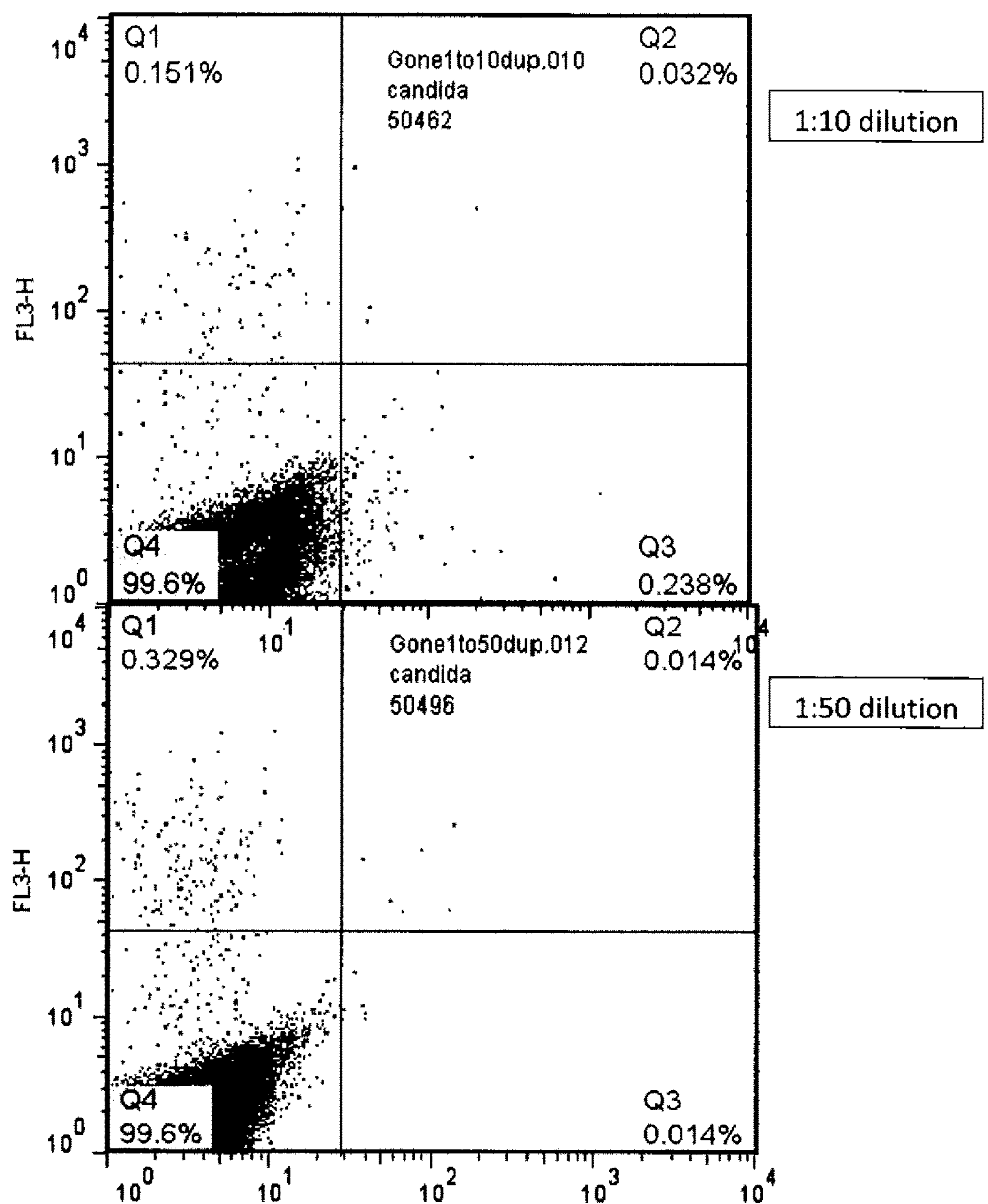

FIG. 9A: Binding of modified chitin and laminarin vaccine-induced antibodies to whole *Candida albicans* by flow cytometry.

Tetanus toxoid antibody controls binding to yeast cells.

Figure 9B:
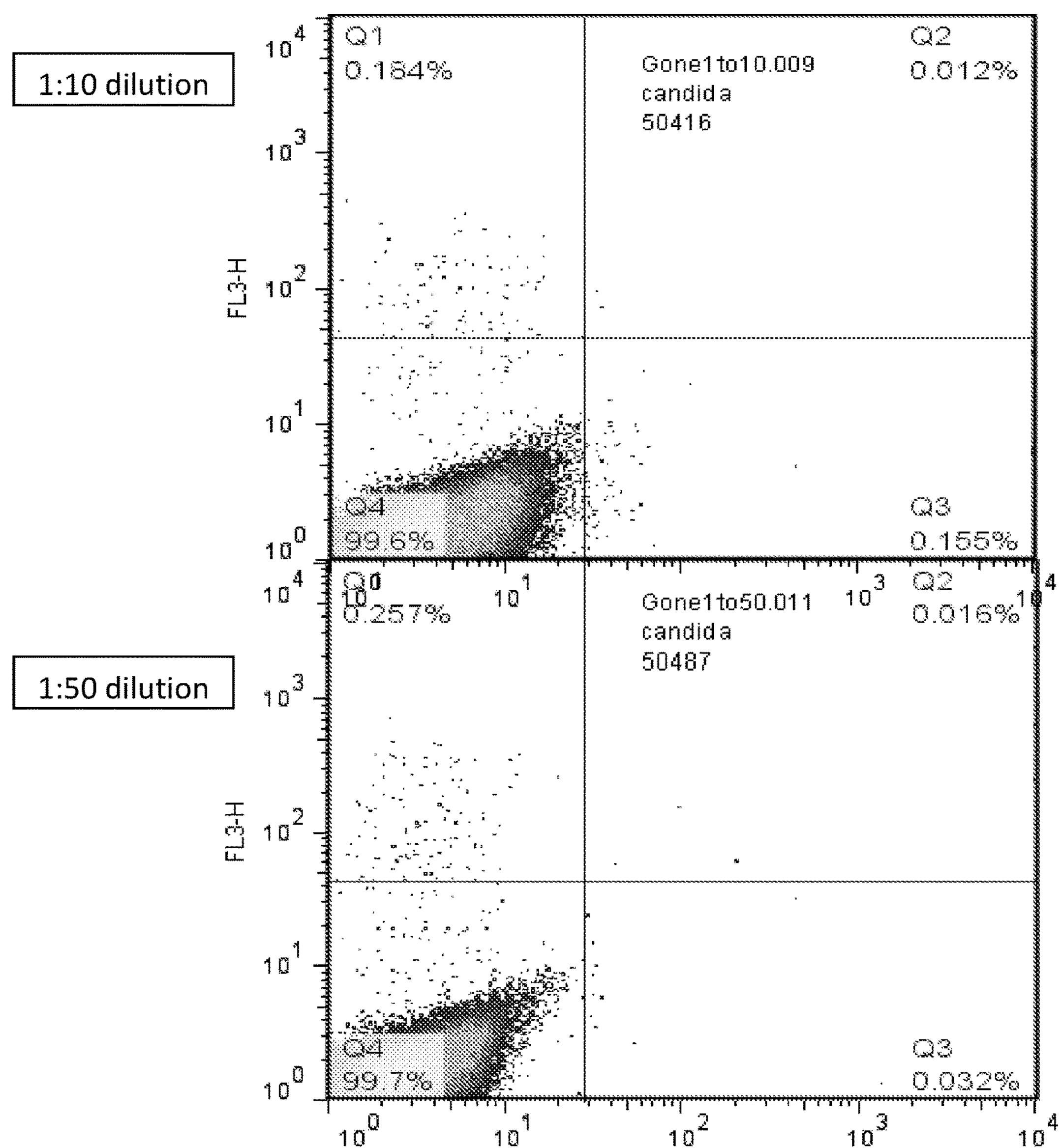

FIG. 9B: Binding of modified chitin and laminarin vaccine-induced antibodies to whole *Candida albicans* by flow cytometry.

Tetanus toxoid antibody controls binding to yeast cells.

Figure 10A:
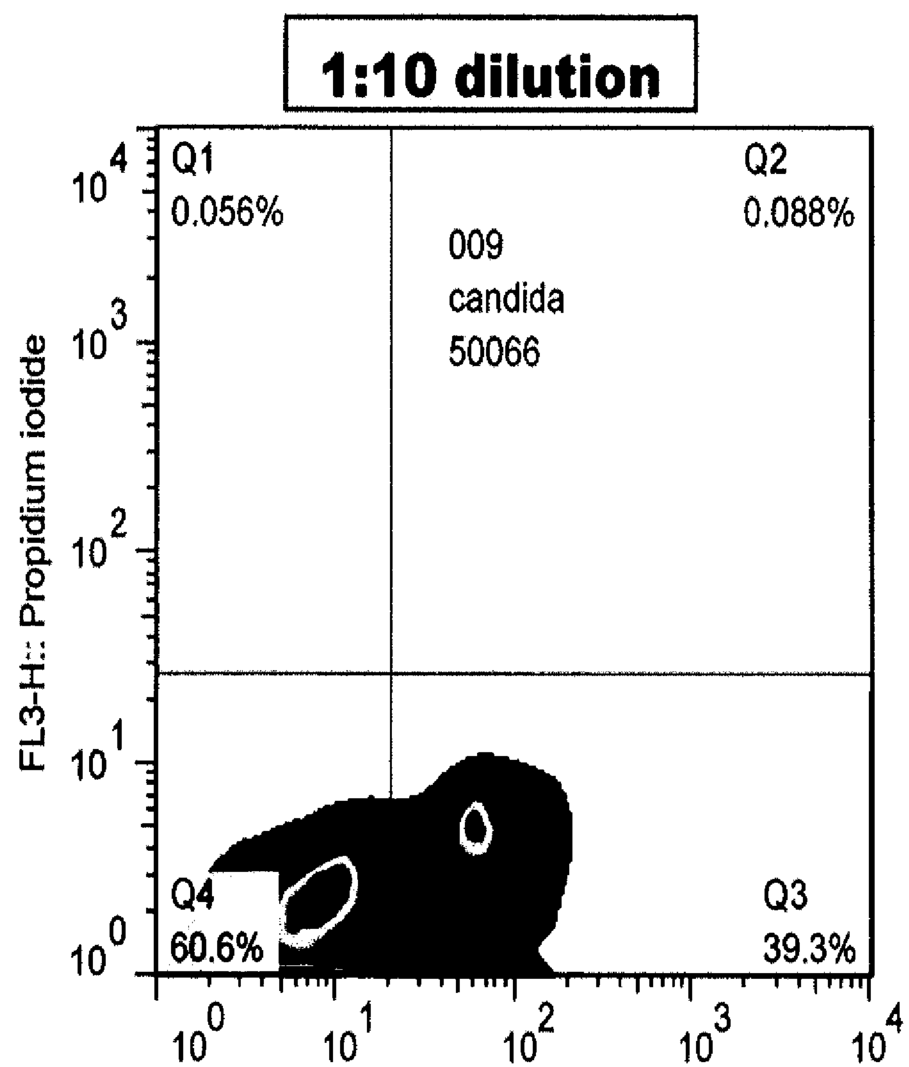

FIG. 10A: Binding of modified chitin and laminarin vaccine-induced antibodies to whole *Candida albicans* by flow cytometry.

Laminarin antibody binding to yeast cells grown at 30 C in YPD medium o/n.

Figure 10B:
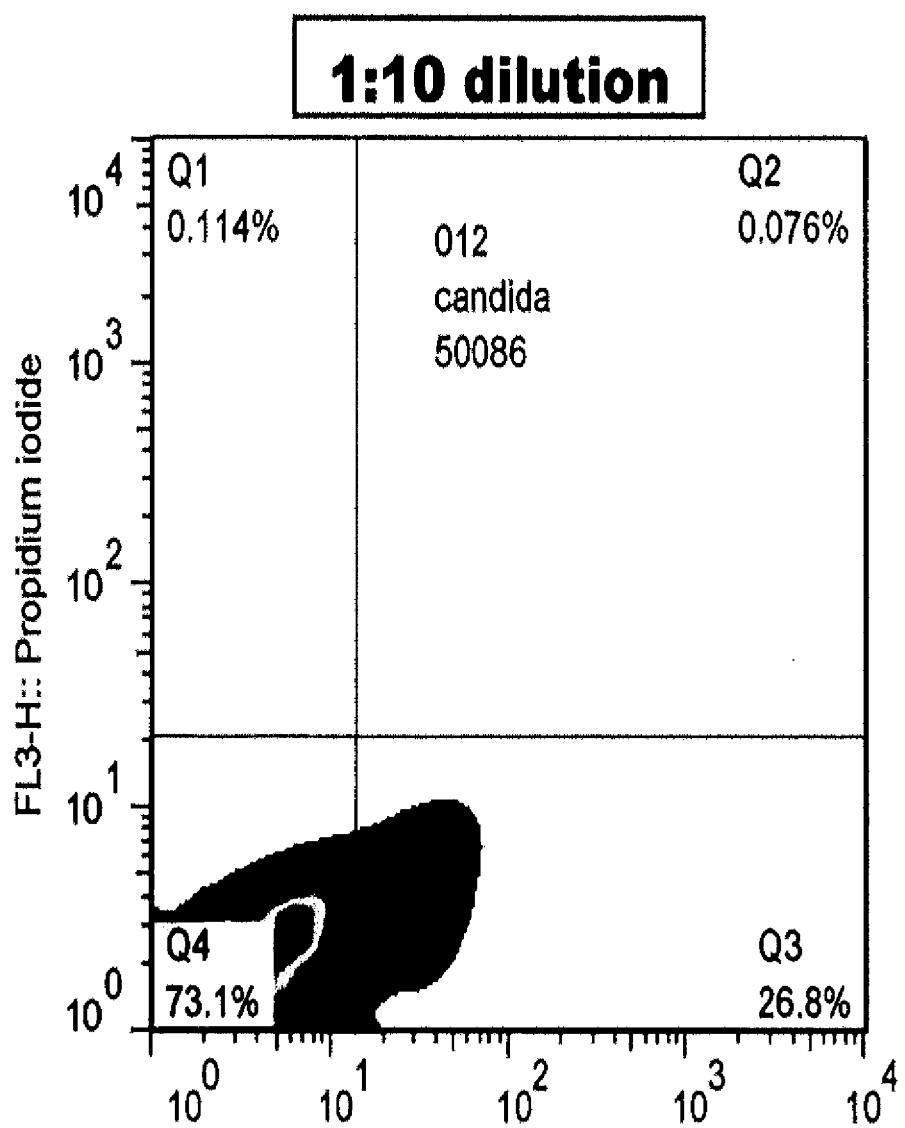

FIG. 10B: Binding of modified chitin and laminarin vaccine-induced antibodies to whole *Candida albicans* by flow cytometry.

Modified chitin antibody binding to yeast cells grown at 30 C in YPD medium o/n.

Figure 10C:
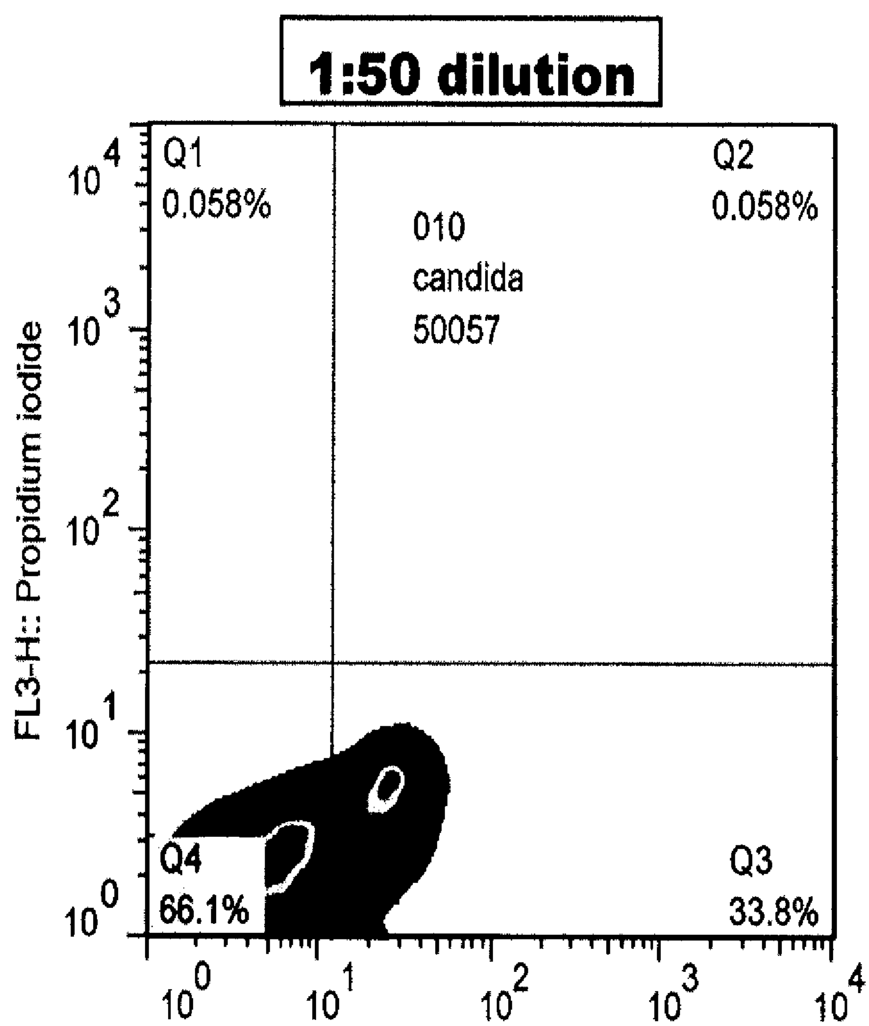

FIG. 10C: Binding of modified chitin and laminarin vaccine-induced antibodies to whole *Candida albicans* by flow cytometry.

Laminarin antibody binding to yeast cells grown at 30 C in YPD medium o/n.

Figure 10D:
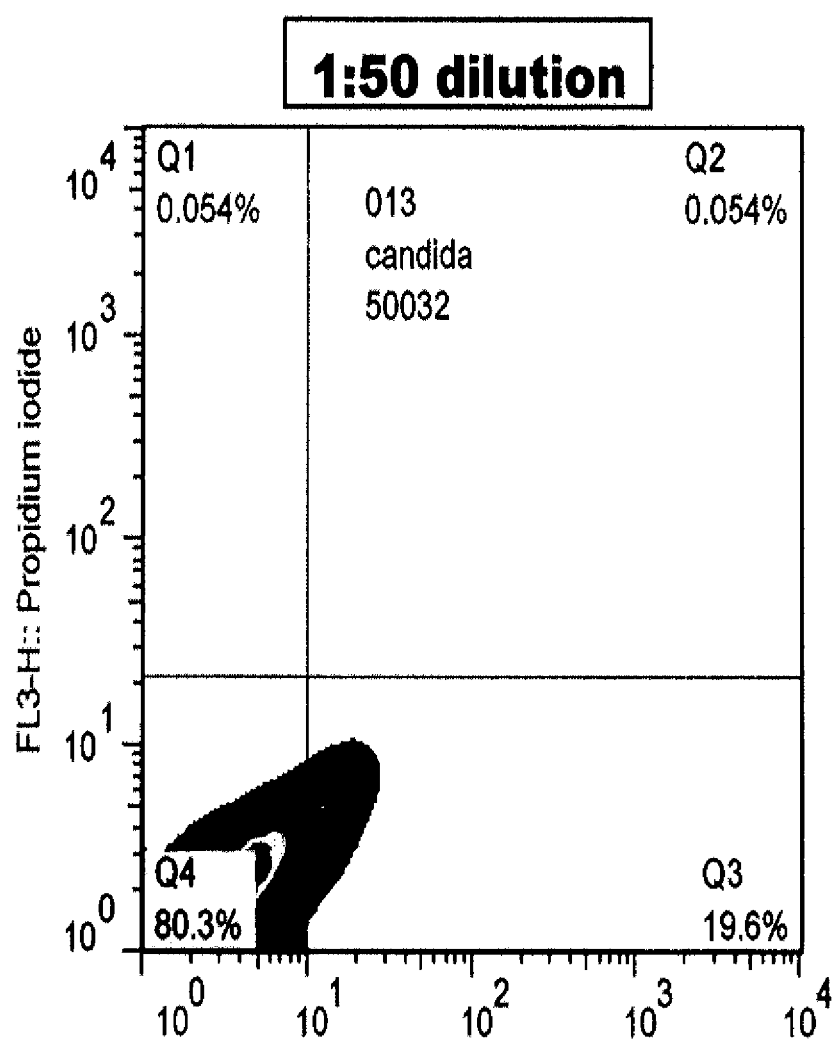

FIG. 10D: Binding of modified chitin and laminarin vaccine-induced antibodies to whole *Candida albicans* by flow cytometry.

Modified chitin antibody binding to yeast cells grown at 30 C in YPD medium o/n.

Figure 10E:
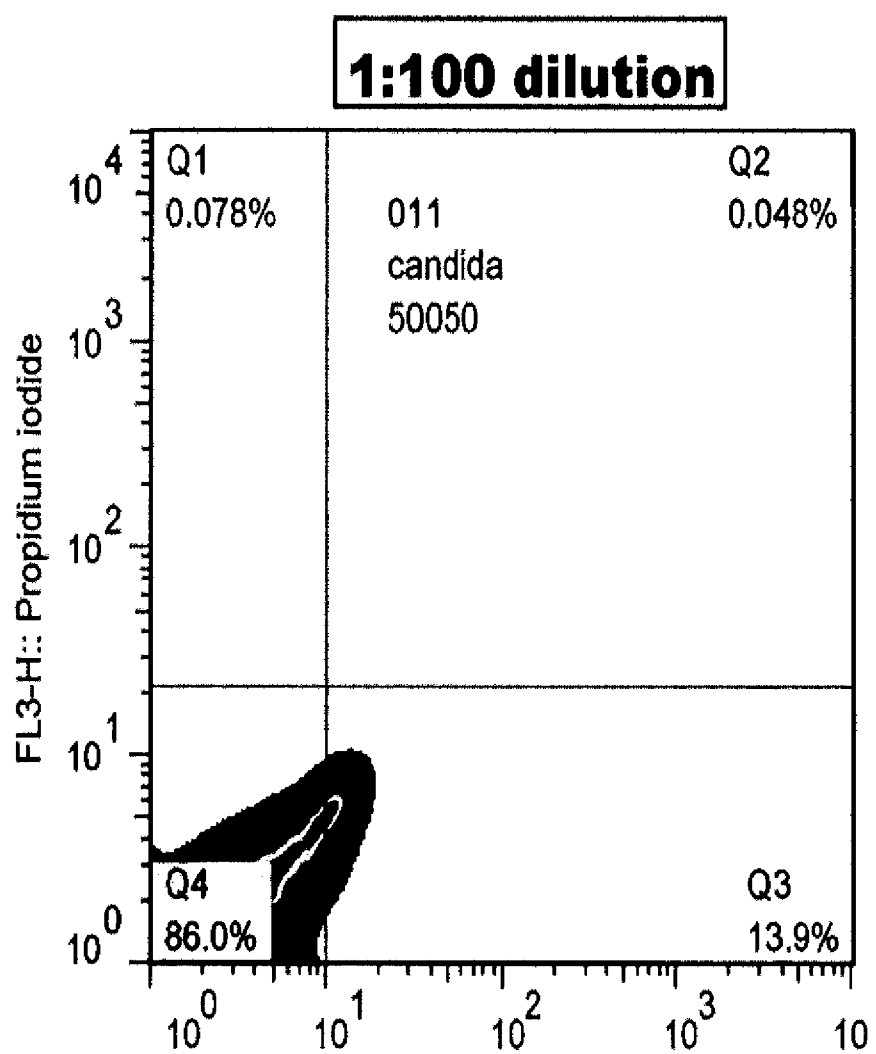

FIG. 10E: Binding of modified chitin and laminarin vaccine-induced antibodies to whole *Candida albicans* by flow cytometry.

Laminarin antibody binding to yeast cells grown at 30 C in YPD medium o/n.

Figure 10F:
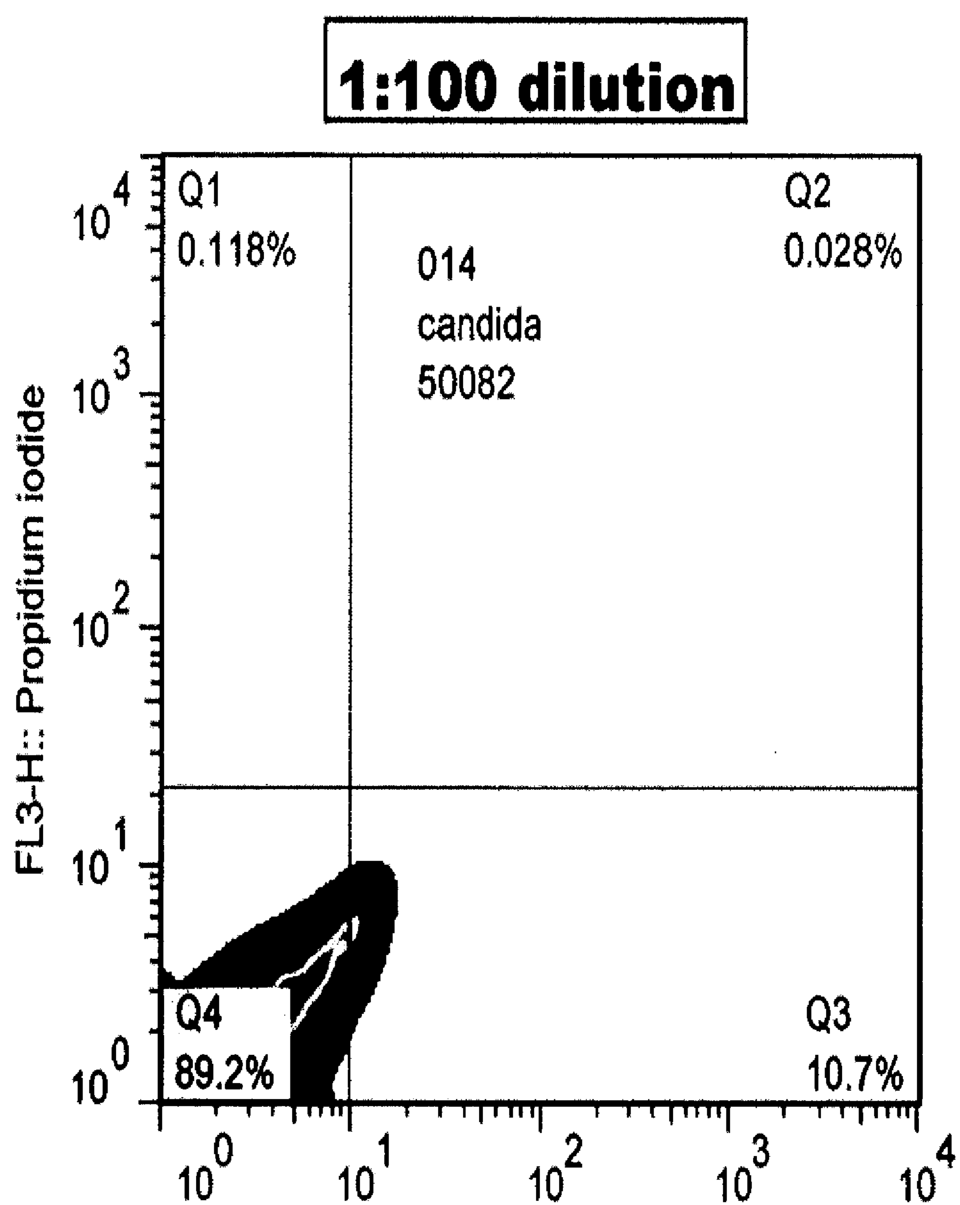

FIG. 10F: Binding of modified chitin and laminarin vaccine-induced antibodies to whole *Candida albicans* by flow cytometry.

Modified chitin antibody binding to yeast cells grown at 30 C in YPD medium o/n.

Figure 11A:
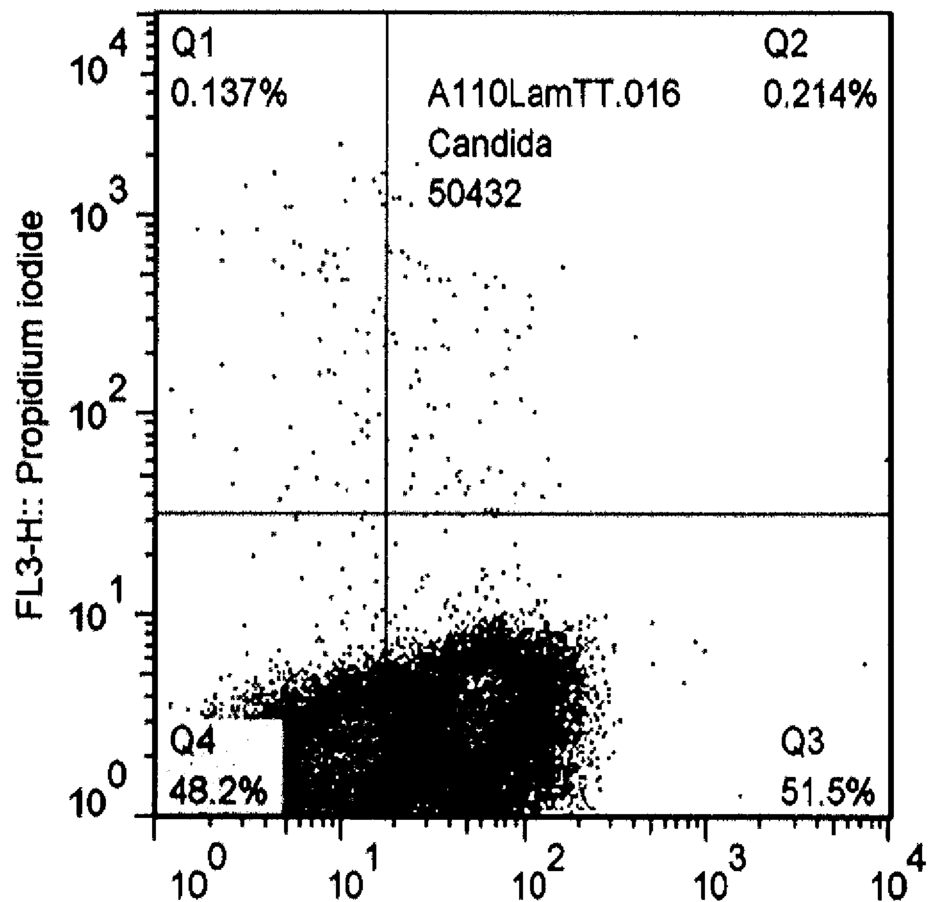

FIG. 11A: Binding of modified chitin and laminarin vaccine-induced antibodies to whole *Candida albicans* by flow cytometry.

Laminarin antibody binding to yeast cells grown at 30 C in YPD medium o/n (1:10 dilution).

Figure 11B:
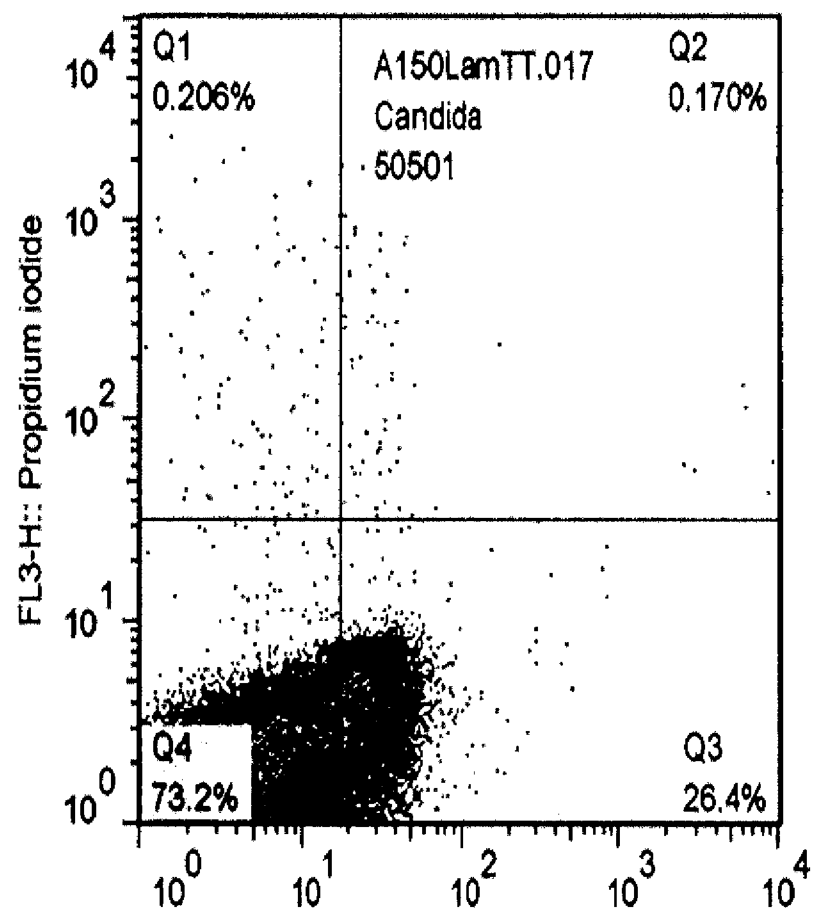

FIG. 11B: Binding of modified chitin and laminarin vaccine-induced antibodies to whole *Candida albicans* by flow cytometry.

Laminarin antibody binding to yeast cells grown at 30 C in YPD medium o/n (1:50 dilution).

Figure 11C:
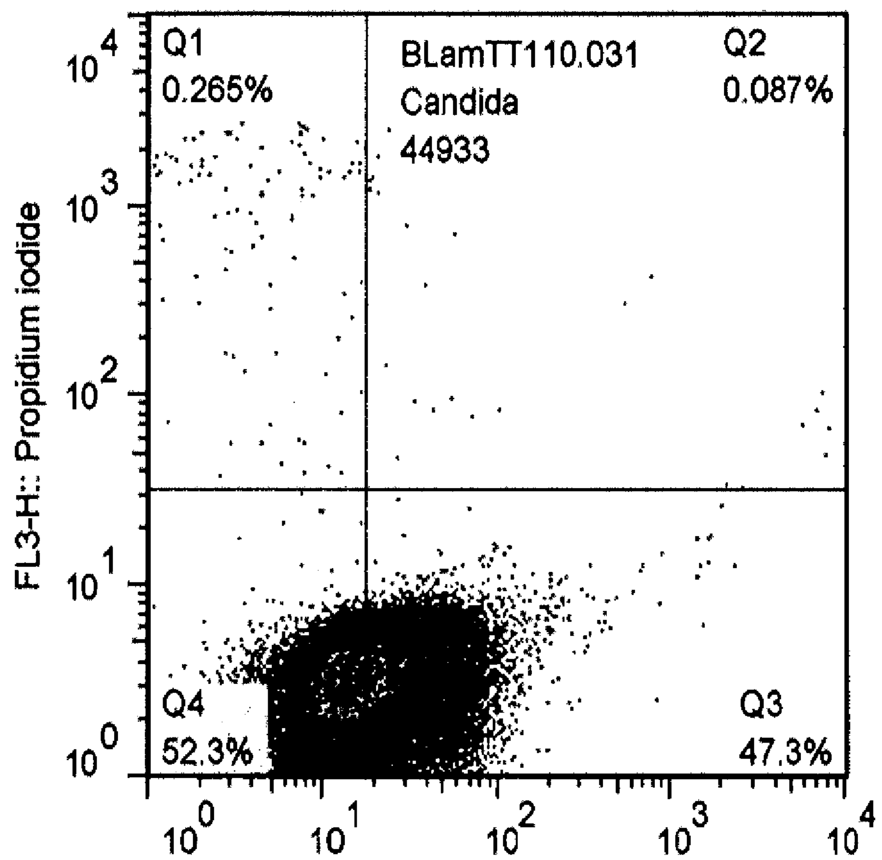

FIG. 11C: Binding of modified chitin and laminarin vaccine-induced antibodies to whole *Candida albicans* by flow cytometry.

Laminarin antibody binding to yeast cells grown at 37 C in YPD medium and serum for 150 min (1:10 dilution).

Figure 11D:
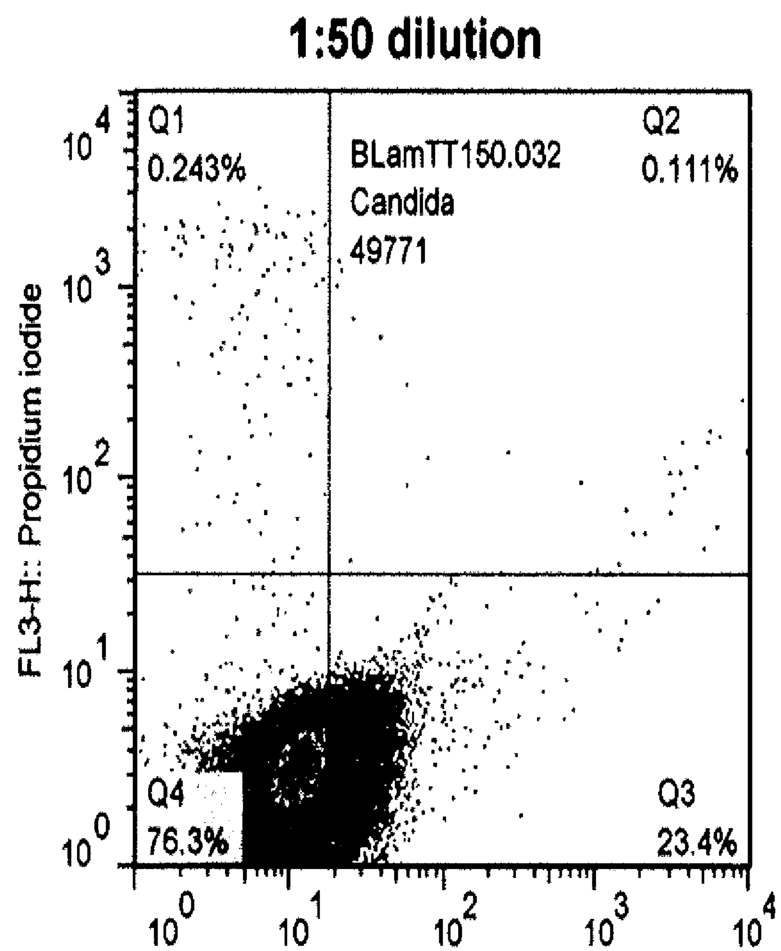

FIG. 11D: Binding of modified chitin and laminarin vaccine-induced antibodies to whole *Candida albicans* by flow cytometry.

Laminarin antibody binding to yeast cells grown at 37 C in YPD medium and serum for 150 min (1:50 dilution).

Figure 11E:
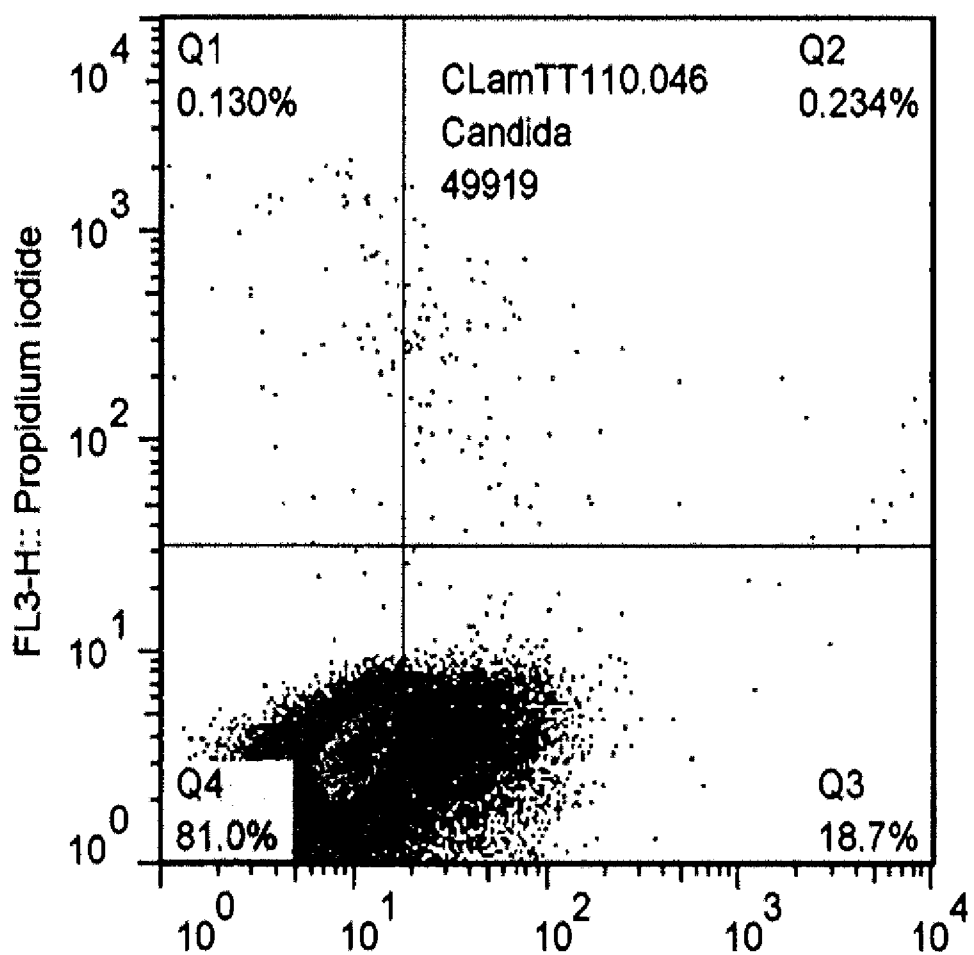

FIG. 11E: Binding of modified chitin and laminarin vaccine-induced antibodies to whole *Candida albicans* by flow cytometry.

Laminarin antibody binding to yeast cells grown at 37 C in YPD medium and serum for 300 min (1:10 dilution).

Figure 11F:
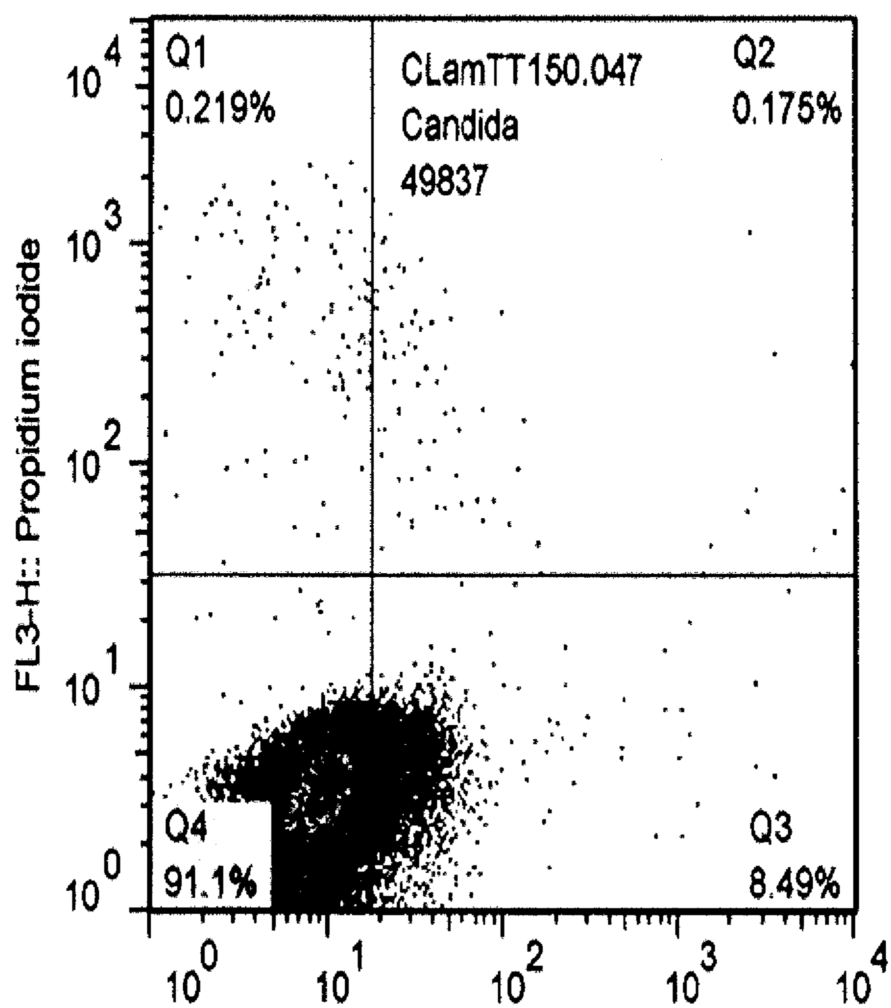

FIG. 11F: Binding of modified chitin and laminarin vaccine-induced antibodies to whole *Candida albicans* by flow cytometry.

Laminarin antibody binding to yeast cells grown at 37 C in YPD medium and serum for 300 min (1:50 dilution).

Figure 12A:
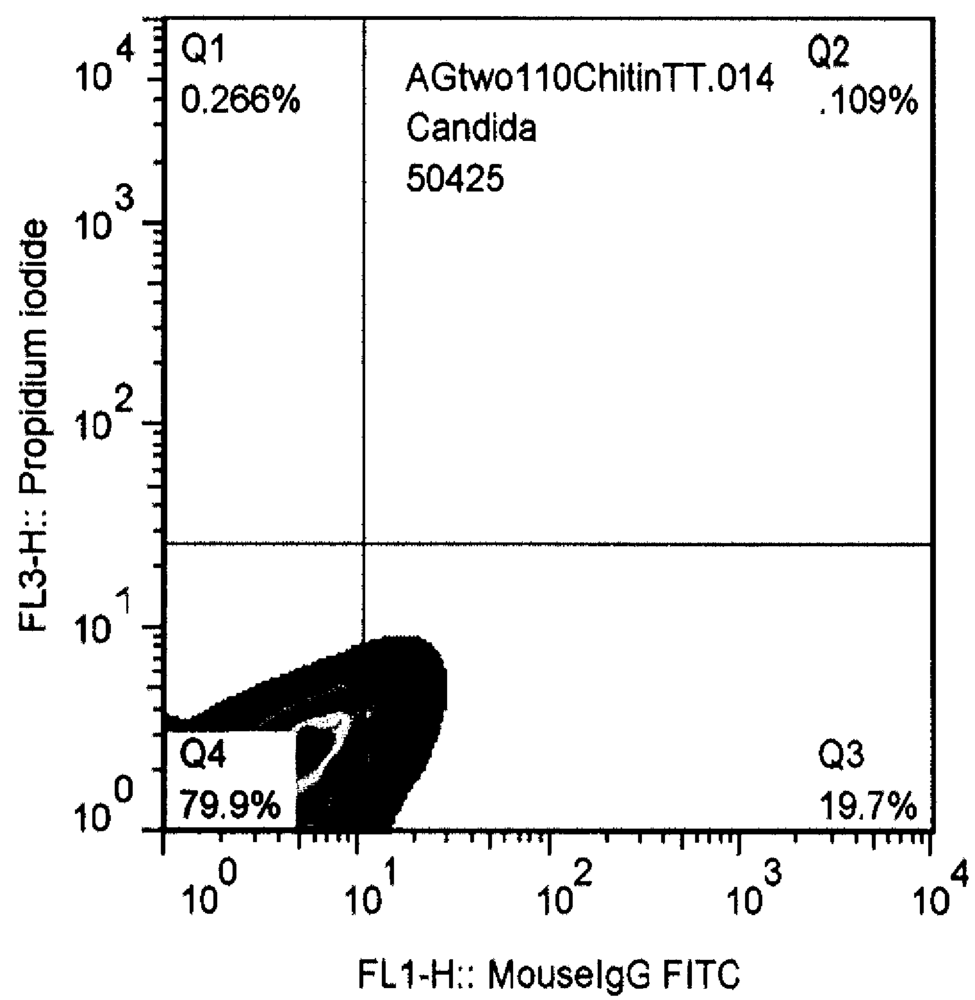

FIG. 12A: Binding of modified chitin and laminarin vaccine-induced antibodies to whole *Candida albicans* by flow cytometry.

Modified chitin antibody binding to yeast cells (mycelia) when grown at 30 C in YPD medium o/n (1:10 dilution).

Figure 12B:
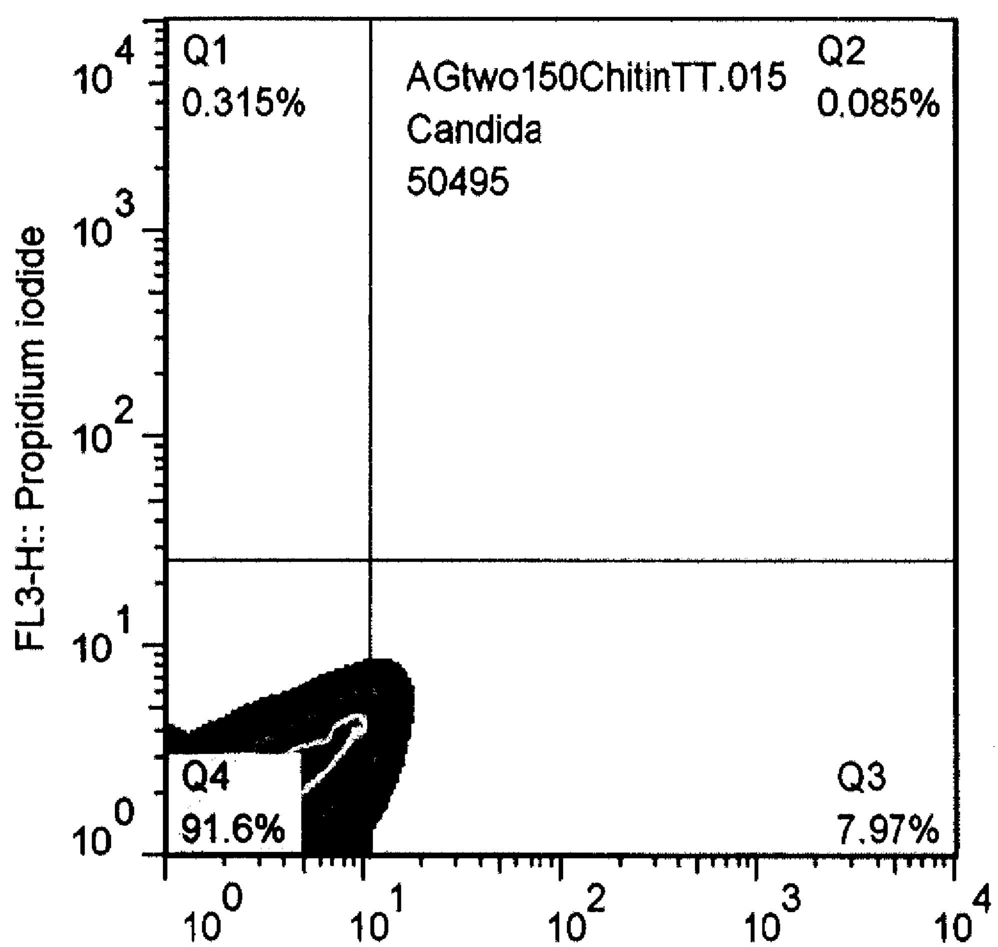

FIG. 12B: Binding of modified chitin and laminarin vaccine-induced antibodies to whole *Candida albicans* by flow cytometry.

Modified chitin antibody binding to yeast cells (mycelia) when grown at 30 C in YPD medium o/n (1:50 dilution).

Figure 12C:
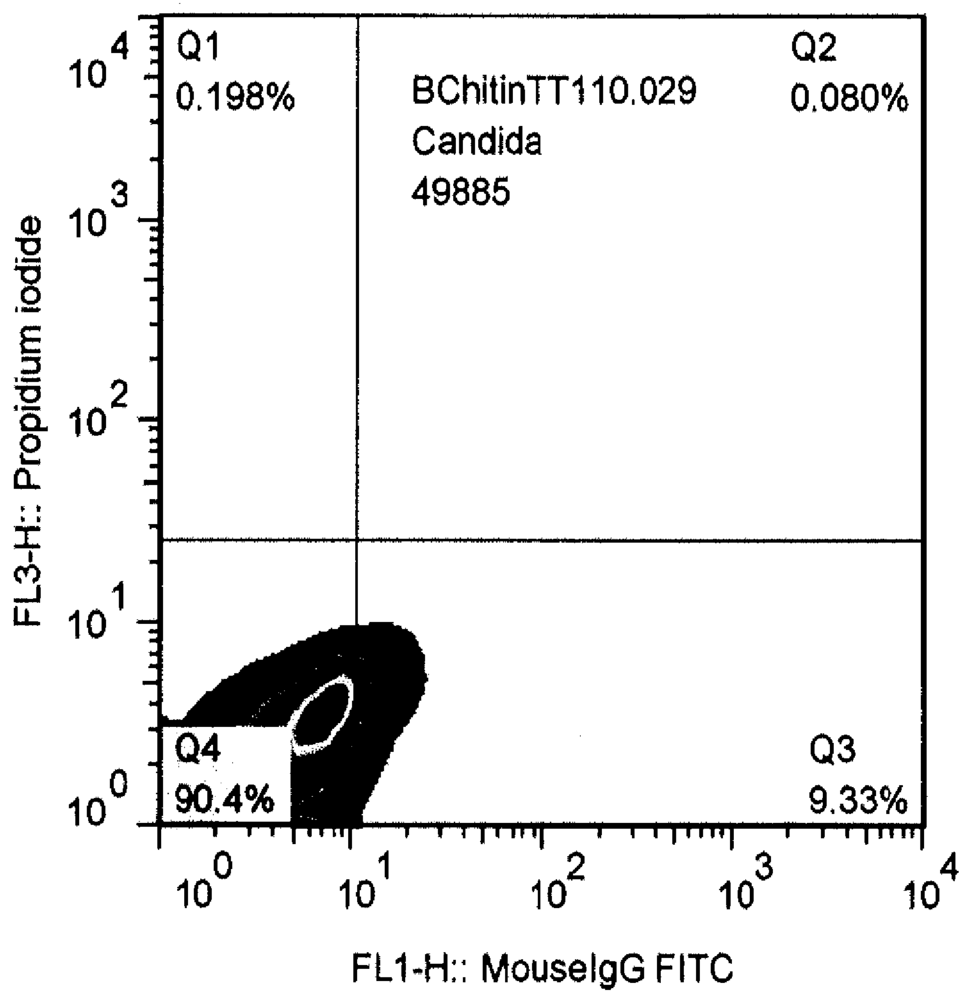

FIG. 12C: Binding of modified chitin and laminarin vaccine-induced antibodies to whole *Candida albicans* by flow cytometry.

Modified chitin antibody binding to yeast cells (mycelia) when grown at 37 C in YPD medium and serum for 150 min (1:10 dilution).

Figure 12D:
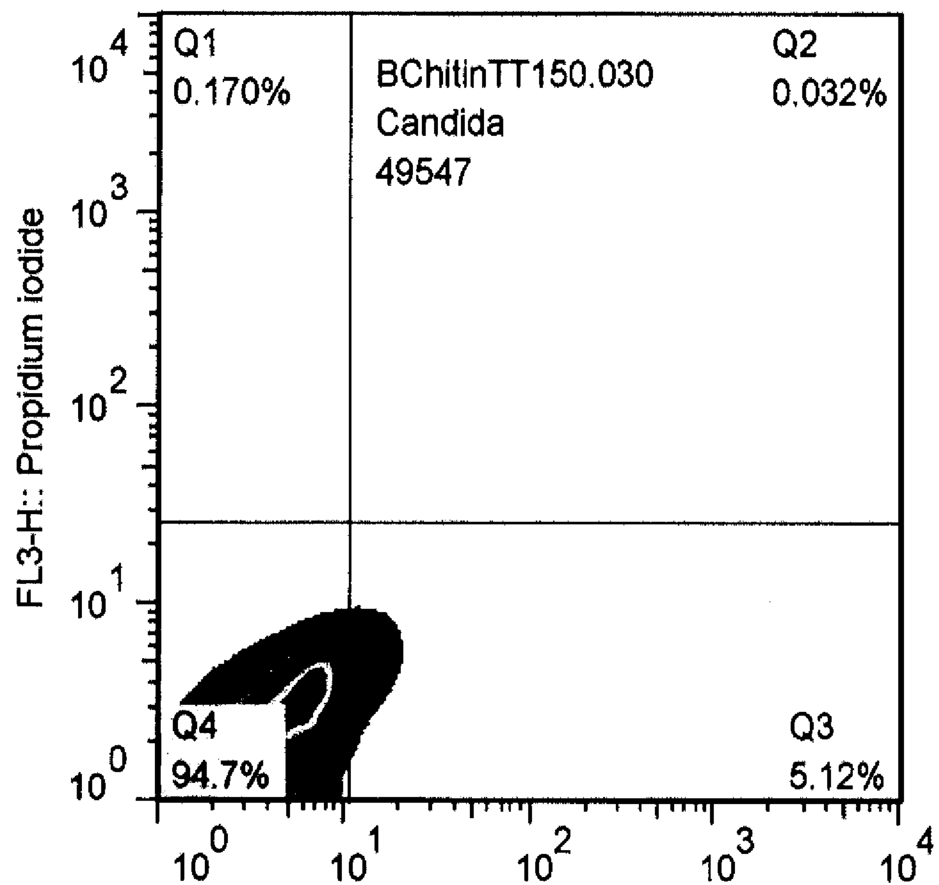

FIG. 12D: Binding of modified chitin and laminarin vaccine-induced antibodies to whole *Candida albicans* by flow cytometry.

Modified chitin antibody binding to yeast cells (mycelia) when grown at 37 C in YPD medium and serum for 150 min (1:50 dilution).

Figure 12E:
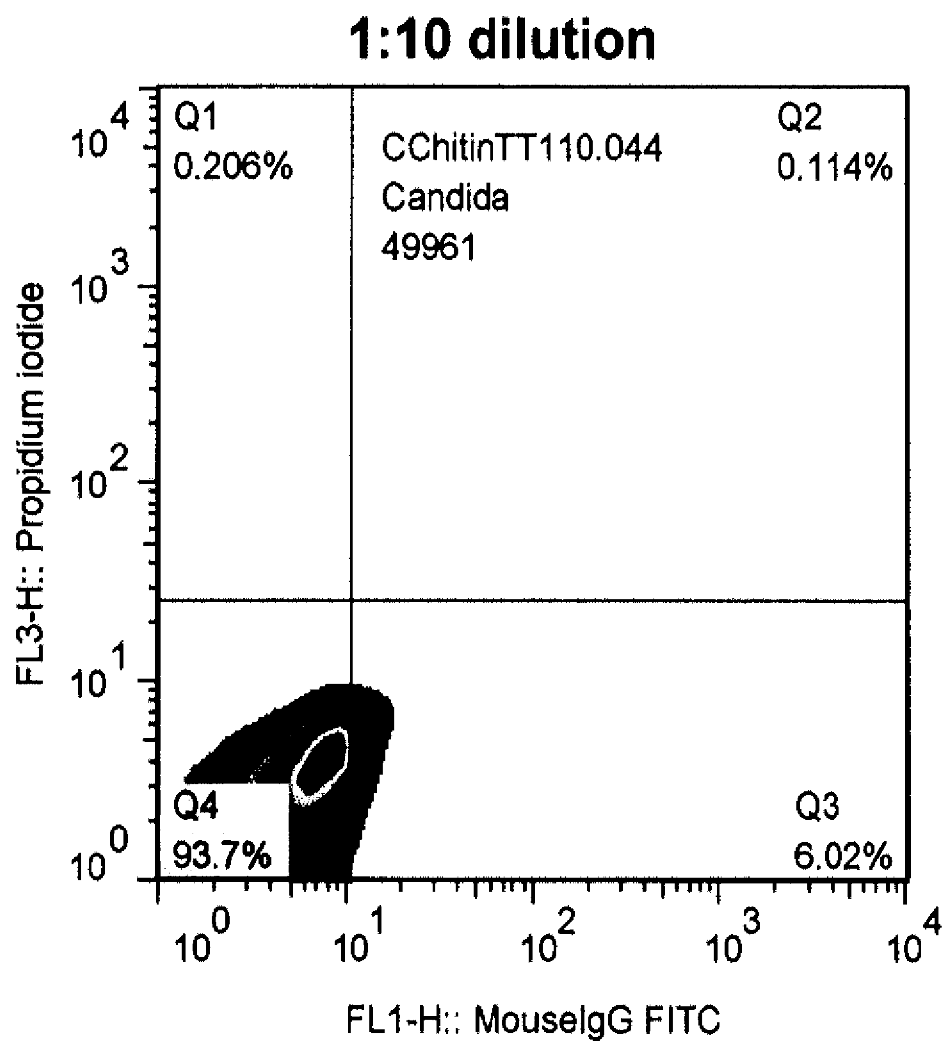

FIG. 12E: Binding of modified chitin and laminarin vaccine-induced antibodies to whole *Candida albicans* by flow cytometry.

Modified chitin antibody binding to yeast cells (mycelia) when grown at 37 C in YPD medium and serum for 300 min (1:10 dilution).

Figure 12F:
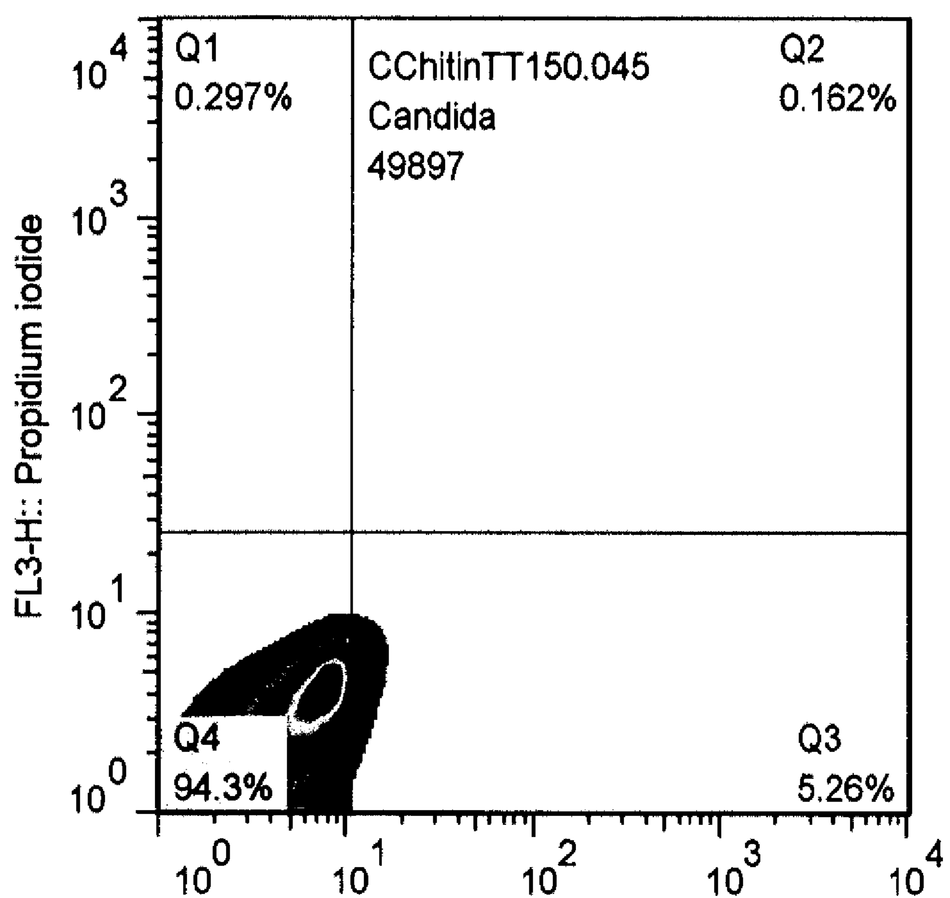

FIG. 12F: Binding of modified chitin and laminarin vaccine-induced antibodies to whole *Candida albicans* by flow cytometry.

Modified chitin antibody binding to yeast cells (mycelia) when grown at 37 C in YPD medium and serum for 300 min (1:50 dilution).

Figure 13A:
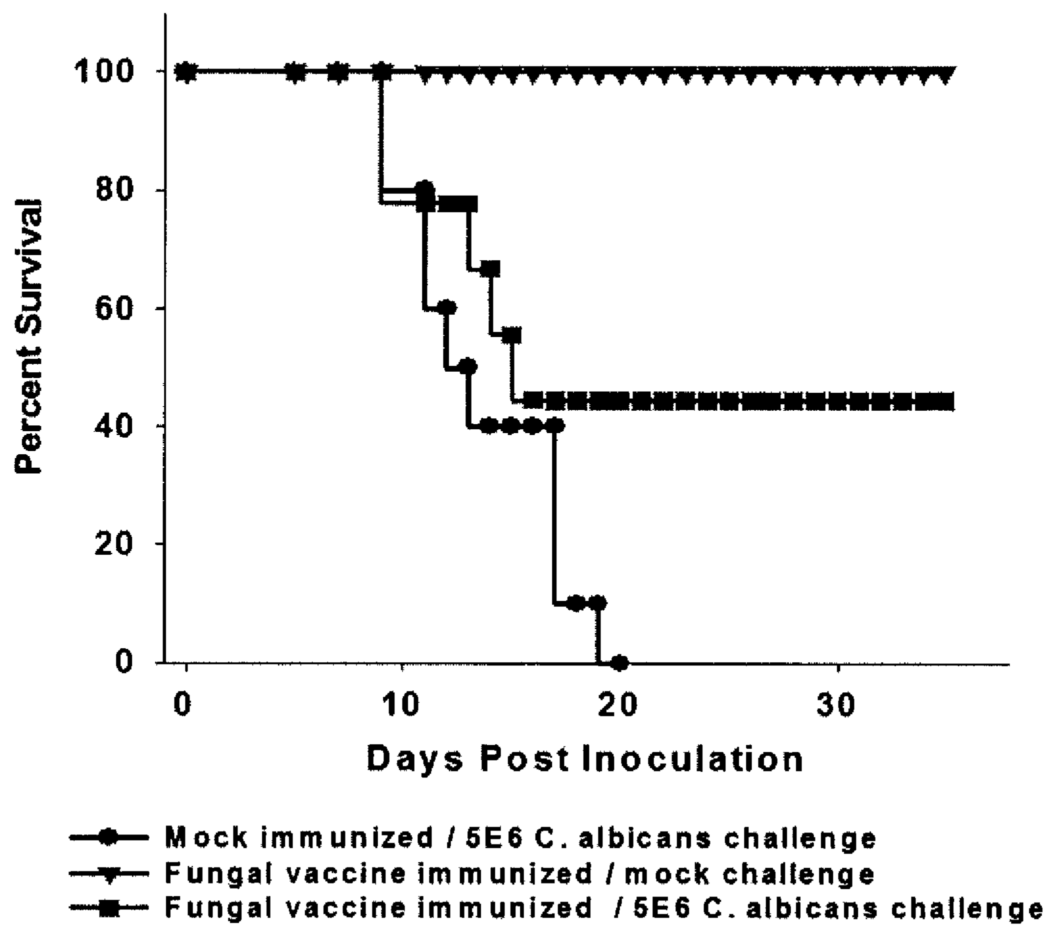

FIG. 13A: Modified chitin-TT vaccine mediated protection from a lethal challenge of *C. albicans*

Mice (Balb/C) were immunized with a modified chitin-TT vaccine and subsequently challenged with a lethal dose of live *C. albicans*. Survival was monitored for 36 days after fungal challenge.

Figure 13B:
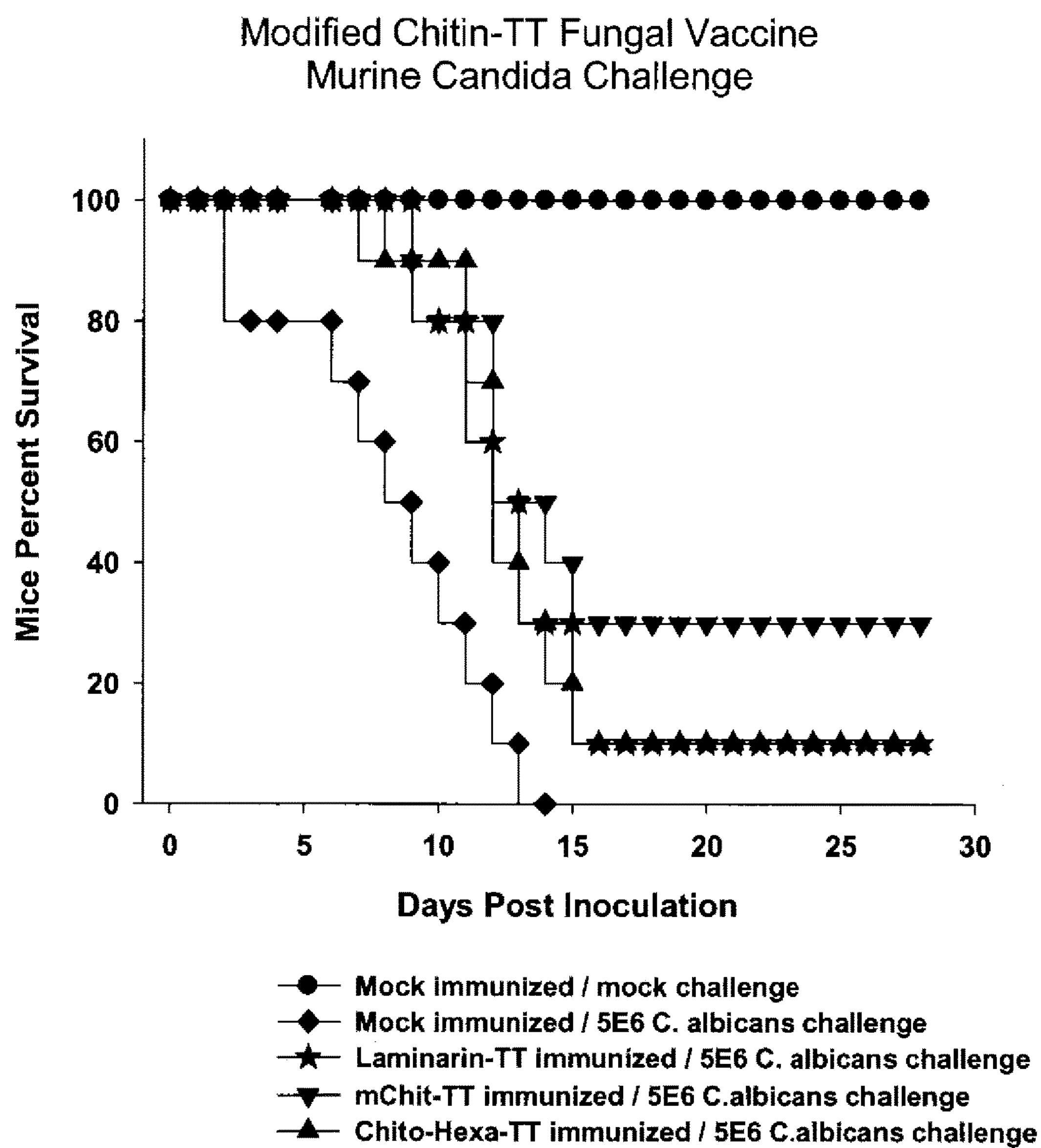

FIG. 13B: Modified chitin-TT vaccine mediated protection from a lethal challenge of *C. albicans*

Mice (CD1) were immunized with a modified chitin-TT and laminarin-TT conjugate vaccines and subsequently challenged with a lethal dose of live *C. albicans*. Survival was monitored for 28 days after fungal challenge.

Figure 14A:
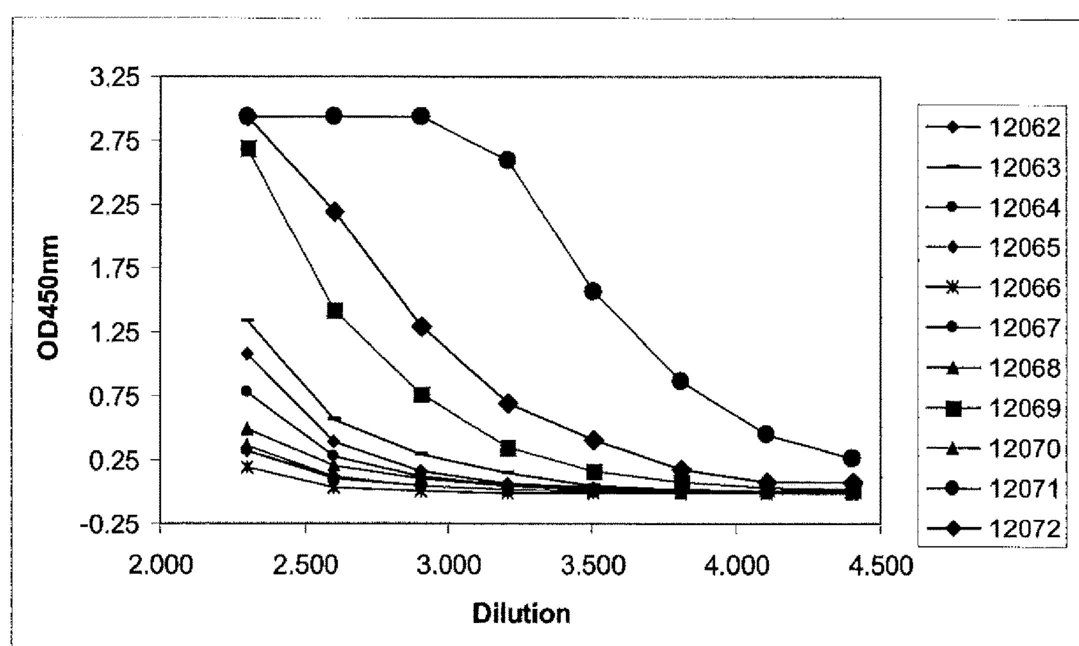

FIG. 14A: Immunoreactivity by ELISA of normal human sera with chitin; modified chitin and laminarin Reactivity of normal human sera (IgG gamma) on a modified chitin-HSA coated plate. All sera react significantly with modified chitin suggesting the presence of naturally acquired chitin-specific antibodies in human through either exposure to fungi or other chitin containing foreign antigens.

Figure 14B:
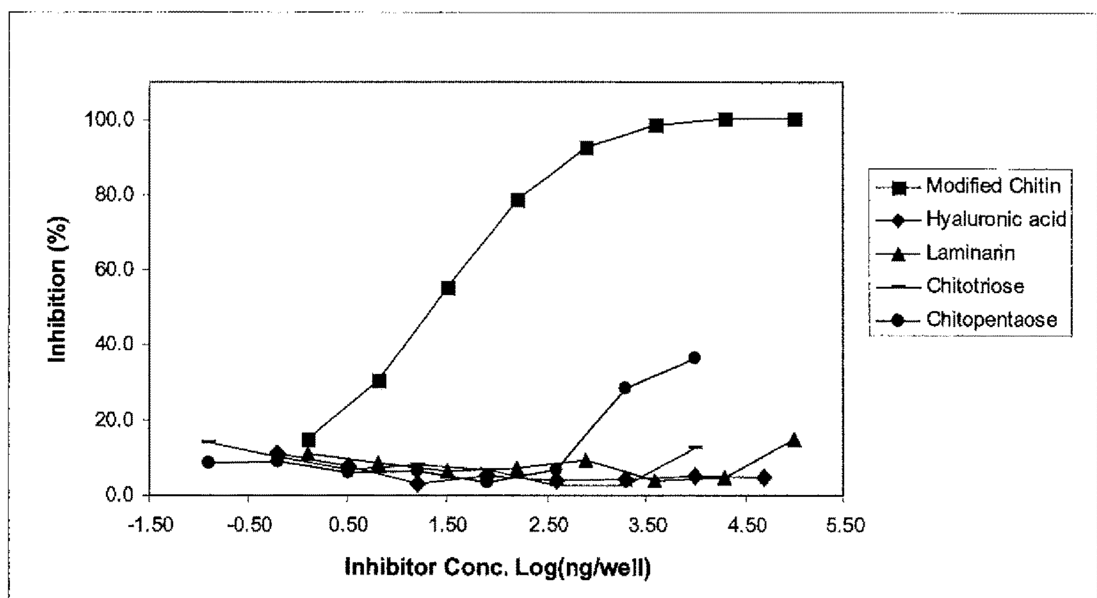

FIG. 14B: Immunoreactivity by ELISA of normal human sera (NHS) with chitin; modified chitin and laminarin Antibody specificity of binding of a high-titer NHS to modified chitin-HSA coated plate by competitive inhibition with various inhibitors. NHS specificity towards modified chitin is the highest, followed by the small chitin oligosaccharide inhibitors (DP5 and DP3).

Figure 14C:
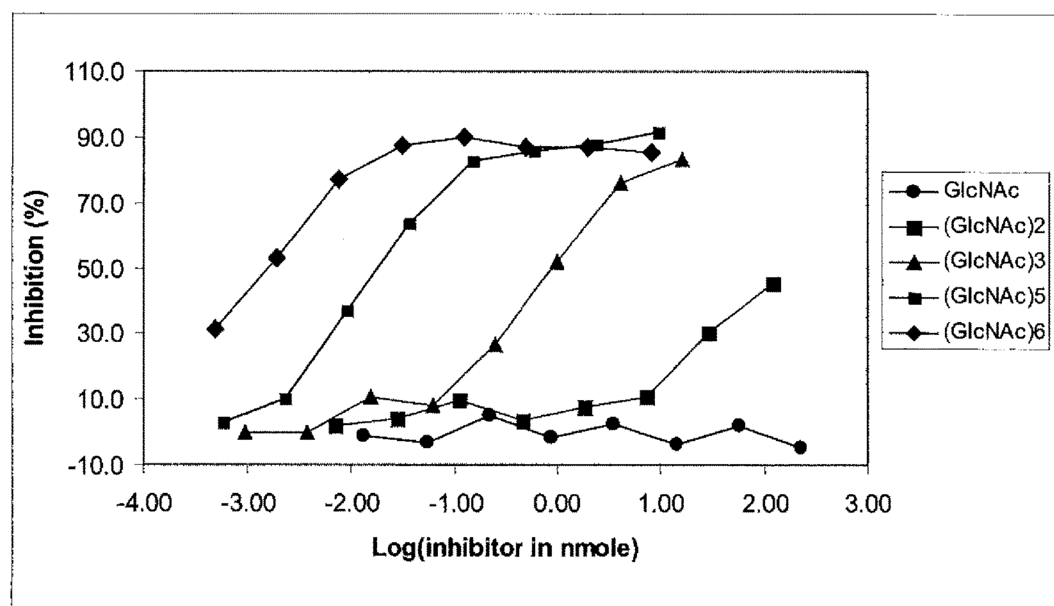

FIG. 14C: Immunoreactivity by ELISA of normal human sera with chitin; modified chitin and laminarin Antibody specificity of binding of a high-titer NHS to Chitohexaose-HSA coated plate by competitive inhibition with chitin oligosaccharides of increasing DP. There is an increase inhibition with increasing size of the chitin oligosaccharides from DP2 to DP6, suggesting that these human antibodies recognize a conformational epitope of chitin with a minimum size of an hexasaccharide.

Figure 14D:
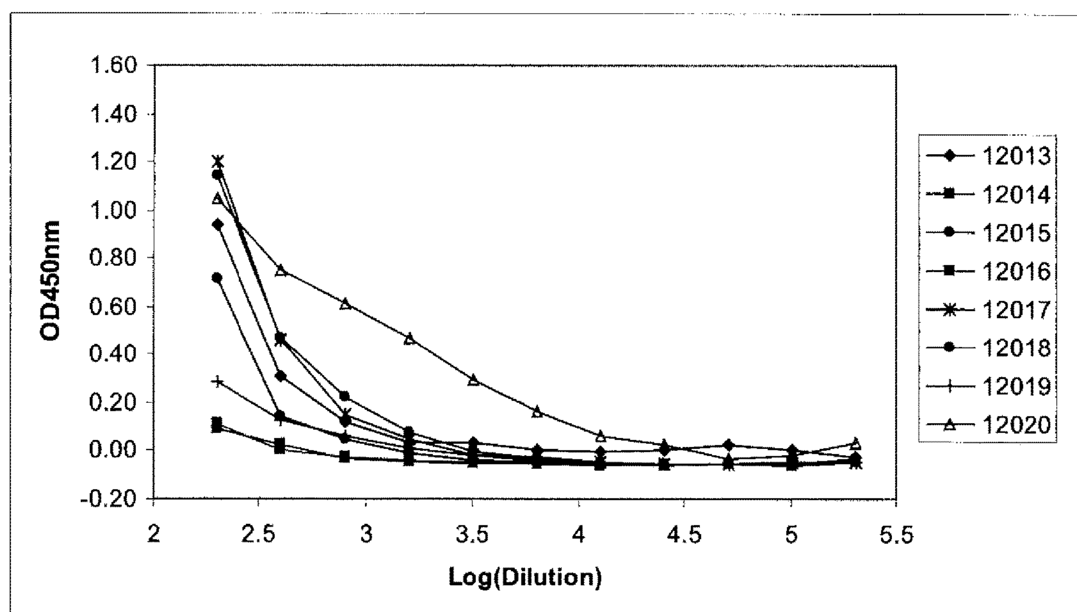

FIG. 14D: Immunoreactivity by ELISA of normal human sera with chitin; modified chitin and laminarin Reactivity of normal human sera (IgG gamma) on a laminarin-HSA coated plate. NHS recognize laminarin (beta glucan) antigen although not to the same degree as modified chitin.

Figure 15A:
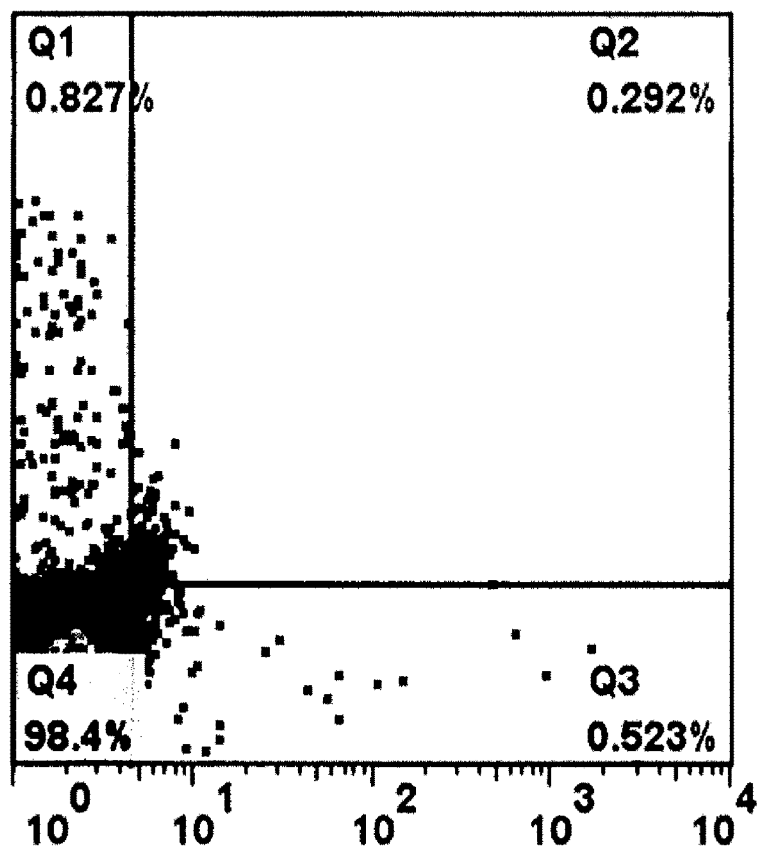

FIG. 15A: Binding of modified chitin and laminarin vaccine-induced antibodies to whole *Cryptococcus neoformans* type A (H99) by flow cytometry. Assays control for antibody binding to yeast cells. This panel shows GCMP-TT Negative Control FIG. 15B: Binding of modified chitin and laminarin vaccine-induced antibodies to whole *Cryptococcus neoformans* type A (H99) by flow cytometry. Assays control for antibody binding to yeast cells. This panels shows Laminarin-TT FIG. 15C: Binding of modified chitin and laminarin vaccine-induced antibodies to whole *Cryptococcus neoformans* type A (H99) by flow cytometry. Assays control for antibody binding to yeast cells. This panel shows Positive Control: Mouse monoclonal antibody to *Cryptococcus.*

Figure 15B:
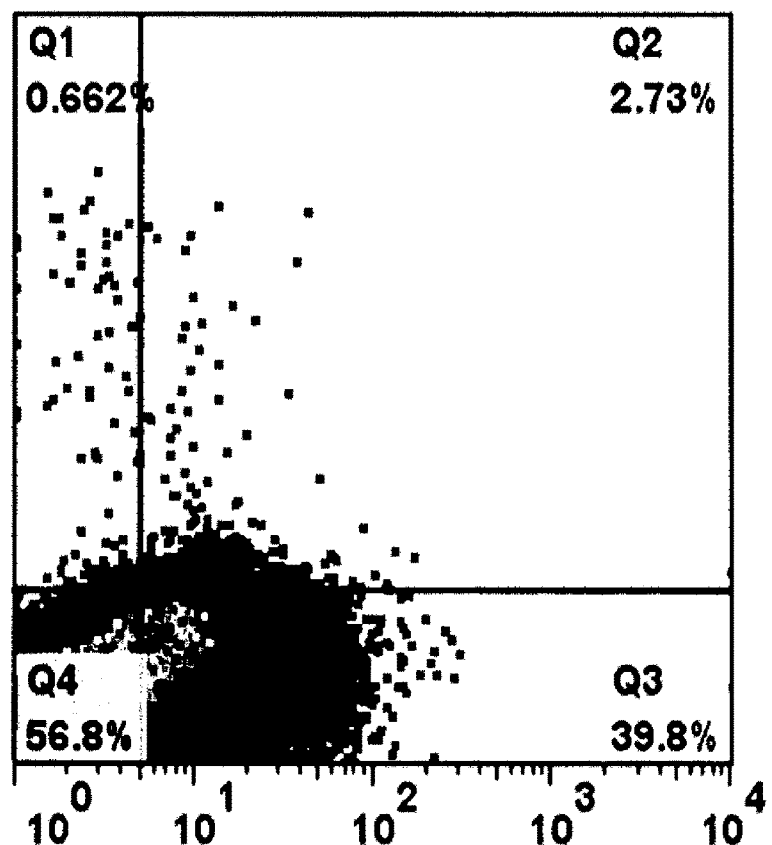
Figure 15C:
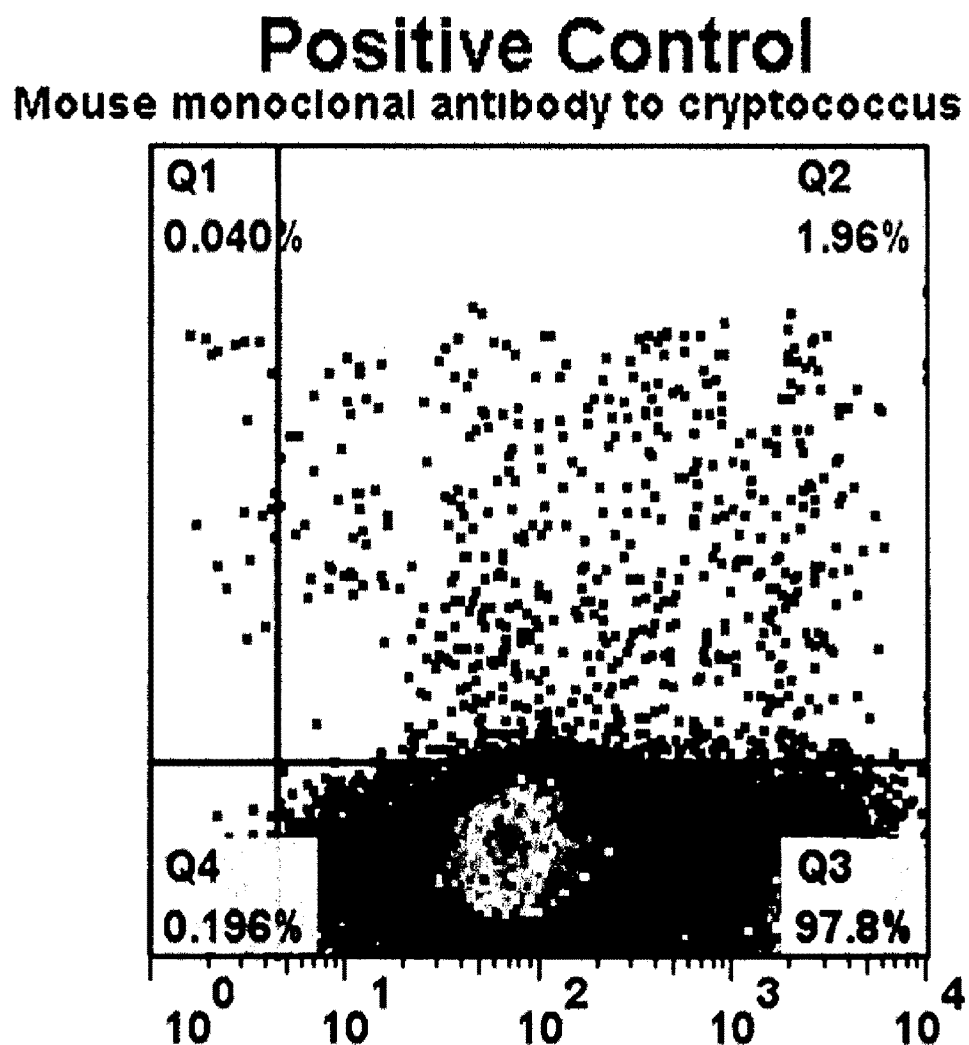
Figure 15D:
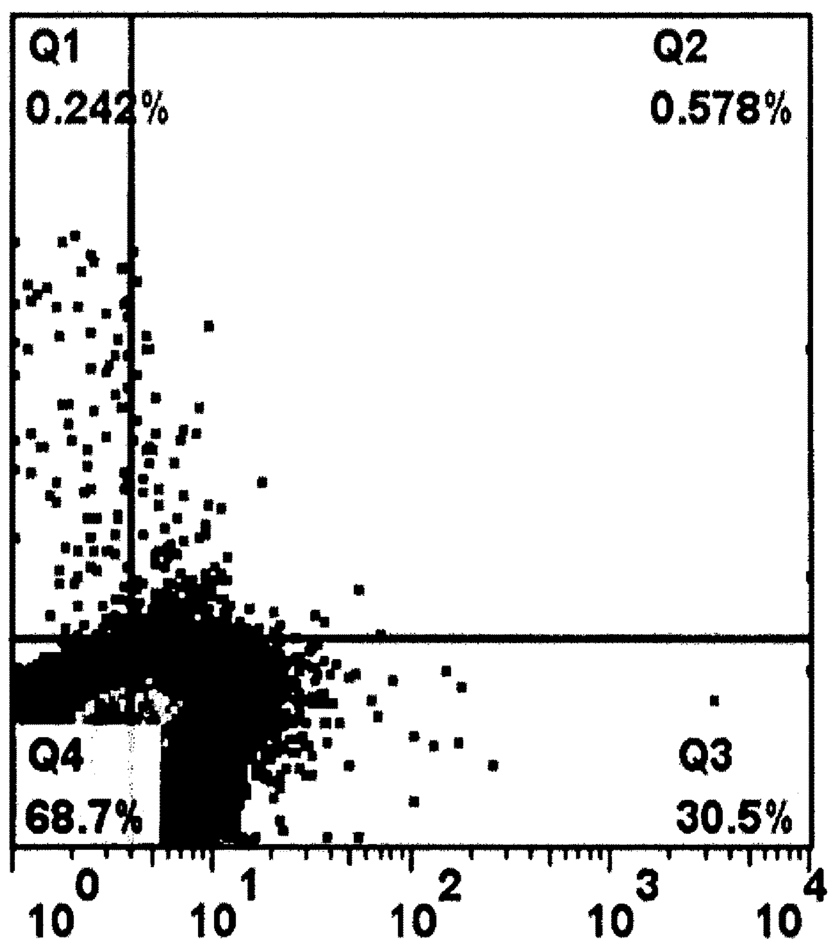

FIG. 15D: Binding of modified chitin and laminarin vaccine-induced antibodies to whole *Cryptococcus neoformans* type A (H99) by flow cytometry. Assays control for antibody binding to yeast cells. This panel shows mChitin-25%-TT.

Figure 15E:
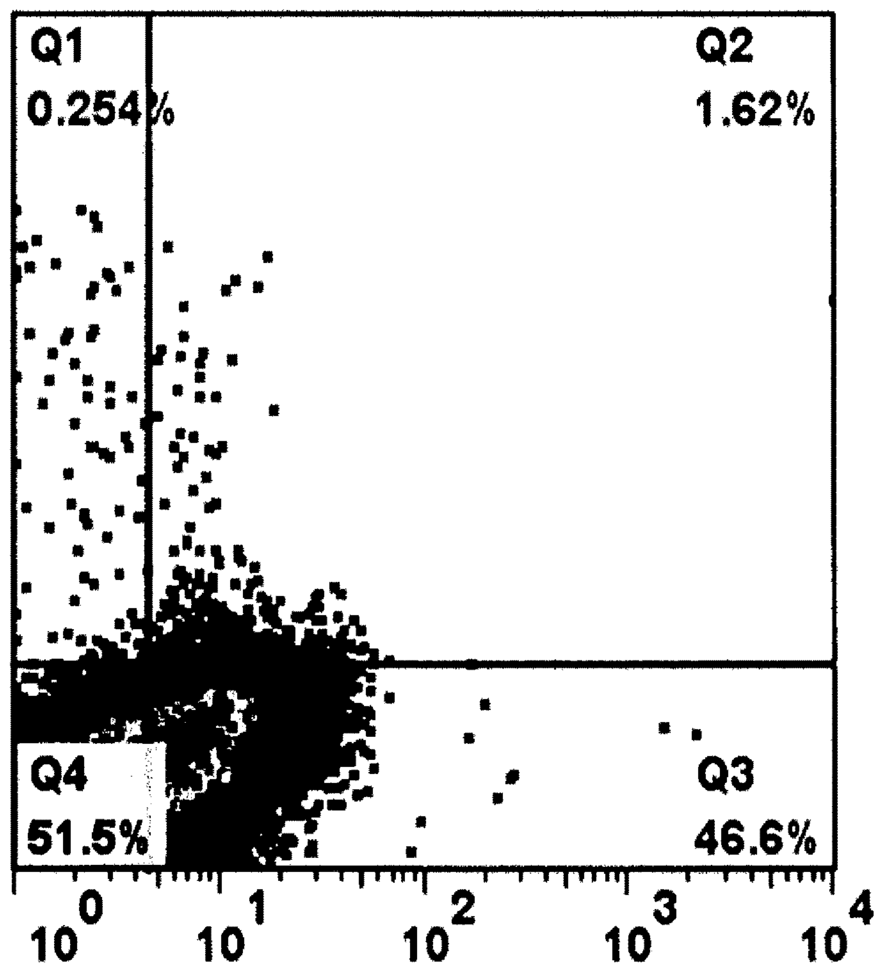

FIG. 15E: Binding of modified chitin and laminarin vaccine-induced antibodies to whole *Cryptococcus neoformans* type A (H99) by flow cytometry. Assays control for antibody binding to yeast cells. This panel shows mChitin-75%-TT.

Figure 15F:
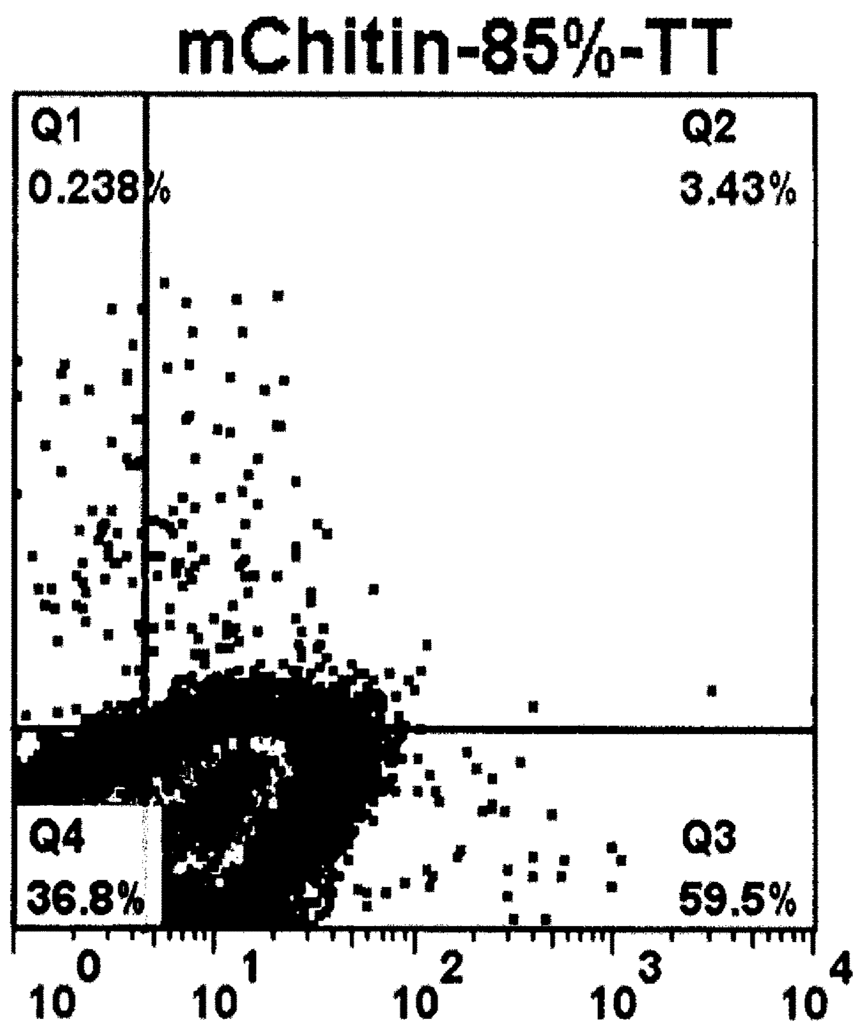

FIG. 15F: Binding of modified chitin and laminarin vaccine-induced antibodies to whole *Cryptococcus neofor-*

*mans* type A (H99) by flow cytometry. Assays control for antibody binding to yeast cells. This panel shows mChitin-85%-TT.

DETAILED DESCRIPTION OF THE INVENTION

This invention provide s compound comprising one or more polysaccharide moieties each independently represented by the formula β(1→4)-[GlcNH—R]$_n$-2,5-anhydromannose, wherein n is a positive integer from 3 to 500, and R is H or an acyl group. In more specific embodiments of this invention, n is a positive integer from 3 to 100, or from 6 to 50. In an embodiment the acyl group R is an acetyl. In another embodiment at least 30% of the acyl groups in the compound are acetyl.

The technical field is prevention, treatment, and detection of fungal infections. Specifically, vaccines or immunotherapeutics that target carbohydrate components of the fungal cell wall can provide treatment for disseminated or locally invasive fungal infections. The disease indications are numerous, including, but not limited to those caused by human pathogenic forms of *Candida, Aspergillus*, and *Cryptococcus* species. Additionally, the ability to generate an antibody response to the conserved carbohydrate components of these pathogenic fungi could lead to the development of diagnostic reagents for detection of these fungal agents in patient biological samples (eg. plasma, serum, or other bodily fluids, as well as tissue sections, etc.). Finally, since Th2 type inflammatory responses to chitin have been implicated in allergic asthma and other allergic conditions (2), a chitin based vaccine that results in a shift toward a Th1 type immune response may ameliorate the symptoms of allergen induced inflammation.

Another fundamental cell wall carbohydrate of interest is the surface α-1,3-glucan. Successful infection by fungal pathogens depends on subversion of host immune mechanisms that detect conserved cell wall components such as beta-glucans. A less common polysaccharide, α-(1,3)-glucan, is a cell wall constituent of most fungal respiratory pathogens and has been correlated with pathogenicity or linked directly to virulence. However, the precise mechanism by which α-(1,3)-glucan promotes fungal virulence is unknown. α-(1,3)-glucan is present in the outermost layer of the *Histoplasma capsulatum* yeast cell wall and contributes to pathogenesis by concealing immunostimulatory beta-glucans from detection by host phagocytic cells. Production of proinflammatory TNFalpha by phagocytes was suppressed either by the presence of the α-(1,3)-glucan layer on yeast cells or by RNA interference based depletion of the host beta-glucan receptor dectin-1. Rappleye et al. have functionally defined key molecular components influencing the initial host-pathogen interaction in histoplasmosis and have revealed an important mechanism by which *H. capsulatum* thwarts the host immune system. Furthermore, they propose that the degree of this evasion contributes to the difference in pathogenic potential between dimorphic fungal pathogens and opportunistic fungi (25). Another study suggested the relevance of cell wall α-1,3-glucan for fungal infection. Because many fungal species could potentially utilize the same or similar stealth infection strategies, targeting the fungal α-1,3-glucan, for example, by conferring α-1,3-glucanase activity to crop plants or applying an inhibitor of the fungal α-1,3-glucan synthase might provide a versatile strategy for the prevention of a wide variety of fungal diseases in important crops. Although the detailed mechanism is still remains to be solved, the fact is that the removal of the surface α-1,3-glucan rapidly activates the defenses responses of the host plant against the fungal pathogens prior to the fungal invasion, resulting in the inhibition of pathogen infection (26). Yeast cell walls are critical for maintaining cell integrity, particularly in the face of challenges such as growth in mammalian hosts. The pathogenic fungus *Cryptococcus neoformans* additionally anchors its polysaccharide capsule to the cell surface via α(1-3) glucan in the wall. Cryptococcal cells disrupted in their alpha glucan synthase gene were sensitive to stresses, including temperature, and showed difficulty dividing. These cells lacked surface capsule, although they continued to shed capsule material into the environment. Electron microscopy showed that the alpha glucan that is usually localized to the outer portion of the cell wall was absent, the outer region of the wall was highly disorganized, and the inner region was hypertrophic. Analysis of cell wall composition demonstrated complete loss of alpha glucan accompanied by a compensatory increase in chitin/chitosan and a redistribution of beta glucan between cell wall fractions. The mutants were unable to grow in a mouse model of infection, but caused death in nematodes. These studies integrate morphological and biochemical investigations of the role of alpha glucan in the cryptococcal cell wall (27).

Thus a vaccine comprising chitin/chitosan and one or more glucan antigens, for example glucan antigens containing homopolymers of α-1,3 linkagers, β-1,3 linkages or both, will target highly conserved fungal cell wall epitopes and provide a pan-fungal vaccine.

This invention provides anti-fungal conjugate vaccines that target conserved carbohydrate cell wall components that are common structural elements across multiple phyla of pathogenic fungi. The composition of these vaccines can include one or more epitopes consisting of oligosaccharides or polysaccharides derived from chitin, alone or in combination with β-mannan or glucan epitopes. The carbohydrate components may be conjugated to an appropriate immunogenic protein carrier, such as tetanus toxoid, diptheria toxoid, or specific protein virulence factors present on the fungal cell surface. In an embodiment of this invention the carrier protein is covalently linked directly to the one or more polysaccharide moieties at the anhydromannose group of each of the polysaccharide moieties. In an embodiment, the carrier protein is covalently linked to the one or more polysaccharide moieties via one or more immunogenic scaffold moieties. Any conventional scaffold moiety can be used, examples of which include a polysaccharide, a peptidoglycan, a polypeptide, and a polyglycerol. The scaffold can be linear or dendrimeric. Envisioned multicomponent vaccines can include, but are not limited to, a simple mixture of chitin, β-mannan and/or glucan epitopes (linear α-1,3- and/or β-1,3-glucans) or derivatives conjugated individually to a carrier protein or immunogenic scaffold of choice.

In one embodiment, the β-mannan can be a β-1,2-mannose tetrasaccharide. In the simplest embodiment of a β-1,2 mannose tetrasaccharide/scaffold complex, the oligosaccharides can be reacted with a modified chitin polysaccharide, to produce a multivalent molecule. The β-1,2 mannose tetrasaccharide can be chemically synthesized (23). The condensation of the oligosaccharide can be accomplished by any of numerous methods available in the art for reaction between the reducing end of the oligosaccharide with the free amino groups of the modified chitin or via a spacer arm equipped with a squarate group (23). In addition, the invention envisions a further step of conjugating the scaffolded oligosaccharide/polysaccharide to a suitable carrier protein. This conjugation may be achieved by a number of means available to a practitioner skilled in the art. For example, the scaffold complex can be conjugated directly by reductive amination, or indirectly by employing a suitable cross-linker containing a spacer length suitable to relieve steric hindrance between the carbohydrate construct and the carrier protein. In yet another embodiment of the invention, a dendrimeric polysaccharide scaffold can be prepared by first reacting the scaffold component with a multifunctional cross-linking reagent, such as Tris-succinimidyl-aminotriacetate (TSAT). This reaction would yield a multivalent array of available scaffolds, in a dendrimer like pattern, for subsequent condensation of the β-1,2 mannose oligosaccharides component.

Alternatively, the different carbohydrate components can be chemically cross linked, either directly or indirectly. For example, the carbohydrates can be joined by linking them together on a common scaffold matrix, such as a dendrimeric substrate, or by co-conjugation to a protein carrier. Yet another embodiment is to directly scaffold the components together by creating chemical cross links between the carbohydrate components and subsequently conjugating the scaffolded polysaccharide matrix to an immunogenic protein or peptide carrier. These chemical cross links can be achieved by any number of means available to a practioner skilled in the art, including, but not limited to reductive amination or the use of heterobifunctional or homobifunctional chemical cross linking reagents.

This invention provide a composition comprising the compound as described above, wherein for at least 80% of molecules of the compound in the composition n has a value from 6 to 50. In an alternative embodiment, this invention provides a composition comprising molecules of the compound as described above, wherein the mean value of n is from 10 to 50.

Methods to produce chitin or chitosan derived fragments for use in an anti-fungal vaccine were tested. Numerous strategies were tested, under various conditions, based in part on methods available in the literature (15-18). Approaches included methods to directly obtain chitin oligosaccharides, such as partial acid hydrolysis of chitin. Variables tested included time, temperature, and scale of reaction. In all tested methods, solubility was a major problem and yield of oligosaccharides of the desired size was in the disappointing range of 1% or less, consistent with published yields, but undesirable for efficient production of a vaccine antigen. Also tested were various conditions, based on published methods, to achieve limited nitrous deamination of chitosan oligosaccharides or polysaccharides, which deaminates free amino groups with concomitant glycosidic bond cleavage (polymer fragmentation) at the deaminated residue. The variables tested for nitrous deamination included varying the mole fraction of nitrous acid and starting with chitosan of varying size and degree of acetylation. In all of these cases, the nitrous acid treatment solubilized the chitosan suspensions, but the reaction was difficult to control and once again, the yield of oligosaccharides of the desired size was low. Finally, in an attempt to produce a partially de-N-acetylated chitin as the starting material for the nitrous deamination reaction, chitin was treated with NaOH to effect a limited de-N-acetylation prior to nitrous deamination. This treatment only produced chitin oligosaccharides of very low molecular weight.

Failing to obtain chitin derived fragments of the desired size in acceptable yield with the existing methods according to the art, another strategy for obtaining the desired product was devised, which was to partially re-N-acylate (e.g., re-N-acetylate) chitosan in order to produce a chitin/chitosan mixed polymer with a limited number of glucosamine residues containing free amino groups. Because the subsequent nitrous deamination reaction only occurs at glucosamine residues containing free amino groups, the N-acyl glucosamine (e.g., N-acetyl glucosamine) residues would be resistant to cleavage. Since the acylation (e.g., acetylation) reaction is not catalytic in nature, whether the reaction could be controlled by adjusting the mole fraction of acetylating reagent present in the reaction was tested. By adjusting the quantity of acylating (e.g., acetylating) reagent, it was found that one could directly control the size of the chitin derived fragments in the subsequent nitrous deamination reaction. Furthermore, the two reactions leading from chitosan to modified chitin fragments could be performed as a one pot reaction, consisting of a solid phase acylation (e.g., acetylation) reaction, followed by acidification and nitrous deamination to yield modified chitin fragments. Any convention acylating agent can be used, for example acetic anhydride or acetyl chloride, both of which are acetylating agents, or N-propionic anhydride or propionic chloride, which are propionylating agents.

Figure 1:
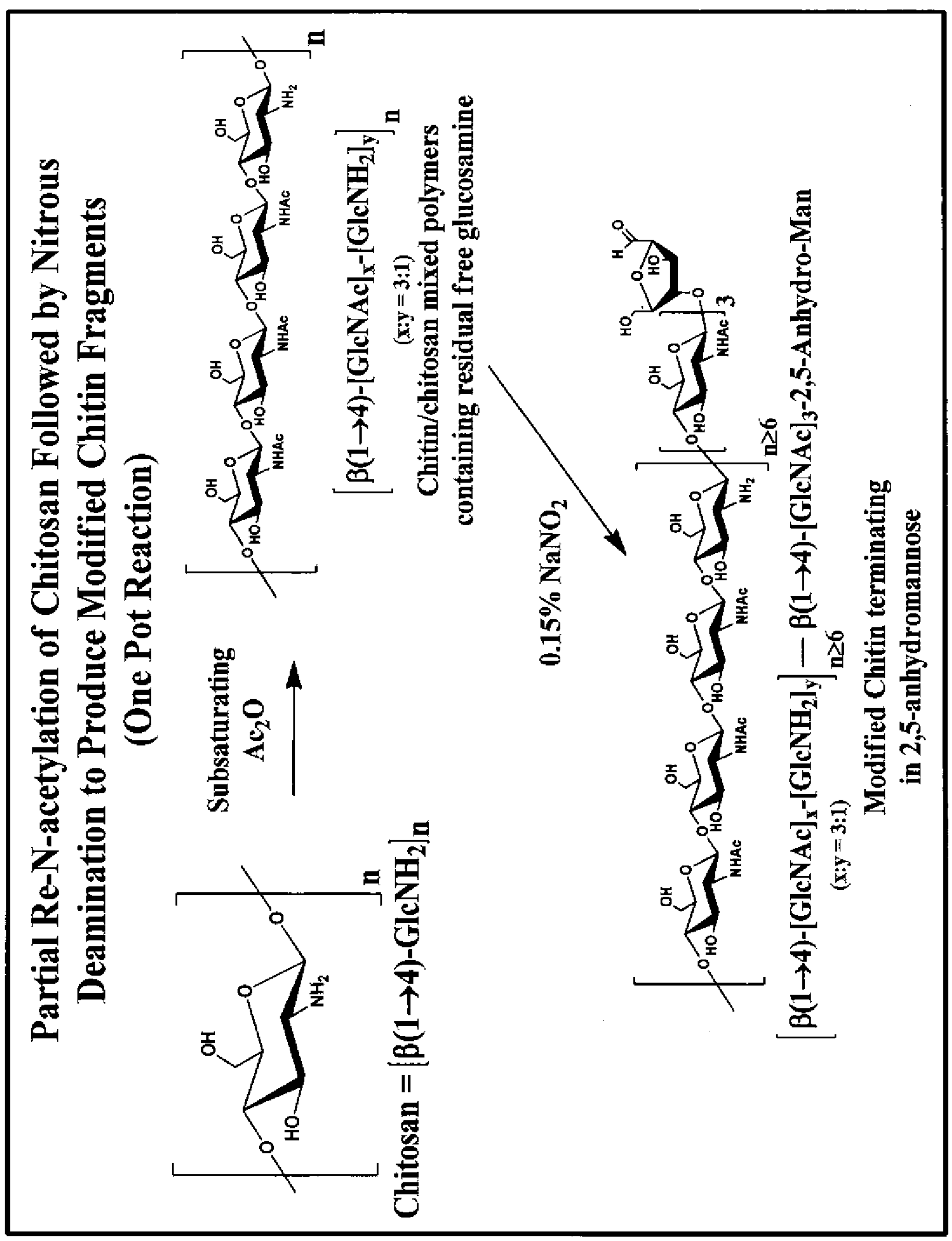
FIG. 1: Reaction scheme for the preparation of modified chitin fragments.

A major impediment to employing chitin in a vaccine formulation is its highly insoluble nature. Methods available in the art for degrading chitin into soluble fragments are not stoichiometrically controlled and it is thus difficult to modulate the degree of depolymerization. The aim was to efficiently produce chitin derived fragments of sufficient size to induce vaccine responses against native chitin polymers in the fungal cell wall, while also meeting the potentially competing criteria that the fragments be soluble or sufficiently uniform that they are suitable for formulation as an injectable vaccine. The non-limiting examples below demonstrate how success was achieved in meeting these criteria in a one pot reaction. By employing a first step of partial re-N-acetylation of chitosan in a stoichiometrically limited reaction, it was possible to subsequently fragment the modified polymer by nitrous deamination, in a controlled fashion (Example 1 and FIG. 1).

This invention provides a method of immunizing a mammalian subject against a fungal infection, comprising administering to the subject an immunogenic amount of a compound or composition as described above. The subject can be a human or non-human animal.

In order to improve the immunogenicity of the carbohydrate antigen and to promote a T-cell dependent memory response, the modified chitin fragment was conjugated to tetanus toxoid. Tetanus toxoid is a non-limiting example of an immunogenic protein that contains multiple T-helper epitopes which make it suitable for use as a protein carrier for carbohydrate conjugate vaccines. Example 2 and FIG. 2 demonstrate a non-limiting example of a method for conjugation of the aldehyde containing chitin fragments to tetanus toxoid via reductive amination. Example 3 and FIG. 3 provide a typical example of an immunization strategy to induce vaccine responses in test animals.

Evaluation of antibody responses in Balb/C mice immunized with the modified chitin vaccine, as outlined here, demonstrates that the vaccine produces robust and specific immune responses toward both the immunizing antigen (Example 4 and FIG. 4) and toward whole *C. albicans* fungi (Example 6 and FIGS. 6A and 6B). The mock (PBS) immunized animals exhibit a basal level of binding to whole *C. albicans* (Example 6A and FIG. 6A), consistent with prior fungal exposure. Immunization with the modified chitin vaccine markedly elevated the titer of serum antibodies that recognize *C. albicans*, indicating an enhancement of the adaptive response to the fungus. Binding of *C. albicans* was substantially inhibited with modified chitin fragments, demonstrating that a significant portion of the serum antibodies recognize chitin and, importantly, that the antibodies recognize chitin in the native fungus. Antigen inhibition experiments verified the specificity of the vaccine response toward the immunizing antigen (Example and FIG. 5A). Furthermore, the induced antibodies showed no detectable cross reactivity with multiple GlcNAc containing glycoconjugates that are present in mammals (Example 5B and FIG. 5B). These negative specificity controls included O-linked GlcNAc-Serine, a major intracellular glycan; ovalbumin and fetuin, which both contain many different N- and O-linked carbohydrate antigens; hyaluronic acid (HA), which is a major component of the extracellular matrix; and crude serum, which contains a multitude of glycoproteins. When the vaccine sera was preadsorbed on a suspension of chitin or chitosan particles, or incubated with soluble chitin/chitosan, binding to the modified chitin antigen was dramatically inhibited (Example 5C and FIGS. 5C and 5D), further demonstrating the specificity of the vaccine response. Antigen affinity purification of the vaccine induced serum antibodies show that the chitin specific fraction is capable of binding whole *C. albicans*. These data provide a concrete example of a vaccine directed toward a conserved and essential component of the fungal cell wall, namely chitin, which is present in all known pathogenic fungi.

Analysis of the binding of modified chitin vaccine induced antibodies to *C. albicans* yeast cells by flow cytometry indicate that the modified Chitin antibodies stained positively *candida* cells with about 25% of live population binding at 1:10 dilution (Example 6C and FIGS. 10B, 10D and 10F) further supporting the binding data detailed in Example 6. High titer laminarin (β-glucan) antibodies generated with a laminarin-TT conjugate also stained positively *C. albicans* (FIGS. 10A, 10C and 10E). These data suggest that both carbohydrates are exposed at the surface of the fungus.

The binding of modified chitin antibodies as well as beta-glucan antibodies at various stages of *candida* growth in culture was also examined by flow cytometry. Yeast cells (following overnight incubation at 300 C), and mycelial (filament) forms (following incubation at 370 C for 150 minutes and 300 minutes respectively, were obtained by culture in YPD medium containing serum (FIGS. 7A-C).

The flow cytometry staining results indicate that the binding of the vaccine-induced laminarin antibodies to *candida* cells is highest on yeast cells and decreases as the cells differentiate to the more virulent filament forms of the fungus (FIGS. 11A through 11F) whereas the binding of modified chitin induced antibodies are not affected by the differentiation stages of the fungus indicating their consistent antigenic expression throughout the invasive process (FIGS. 12A through 12F). These results are important for the development of an effective pan-fungal vaccine formulation in that it stresses the need to incorporate more than one cell wall carbohydrate component in the vaccine formulation for an optimum efficacy throughout the fungal invasive process.

Analysis of the binding of modified chitin vaccine induced antibodies to *Cryptococcus neoformans* type A (H99) yeast cells by flow cytometry indicate that the modified Chitin antibodies stained positively cryptococcal cells with about 31%, 47% and 60% of live population binding at 1:10 dilution with the 25%, 75% and 85% modified chitin-TT conjugate antibodies respectively (Example 6 and FIGS. 15D, 15E and 15) further supporting the binding data detailed in Example 6. High titer laminarin (β-glucan) antibodies generated with a laminarin-TT conjugate also stained positively *Cryptococcus neoformans* (FIGS. 15A, 15B and 15C). As for *Candida albicans* these data suggest that both carbohydrates are exposed at the surface of the cryptococcal fungus.

In a preliminary example of protection against a lethal challenge with a pathogenic fungus, Balb/C and CD1 mice that received a single cell wall component vaccine comprising a modified chitin-tetanus toxoid conjugate, showed partial protection against a 100% lethal dose of live *C. albicans* (Example 7 and FIGS. 13A and 13B). In a repeat lethal challenge experiment, the same modified chitin-tetanus toxoid conjugate vaccine displayed similar partial protection against live *C. albicans*, albeit greater protection than the a laminarin (β-glucan)-tetanus toxoid conjugate or an chitohexaose-tetanus toxoid conjugate (FIG. 13B). These results will be extended and further embodiments of the invention, such as vaccines comprising multiple cell wall components (Example 9 and FIGS. 8A through 12F) will be examined for efficacy in similar in vivo lethal challenge models employing, for example, *C. albicans, A. fumigatus*, and *C. neoformans*.

Analysis of normal human sera (NHS) for the presence of chitin, modified chitin and laminarin antibodies outlined here demonstrate that these antibodies are naturally acquired and exist in healthy individuals (FIGS. 14A through 14D). Chitin antibodies seem to be present at significant levels (FIG. 14A) and these levels are significantly higher than those against β-glucan (FIG. 14D), It is interesting to note that chitin antibodies are directed towards a conformational epitope made up of at least a saccharide of DP6 (FIG. 14C). These results are important for the design of a chitin-based vaccine because they suggest that an optimum conjugate vaccine should contain chitin fragments of a least 6 GlcNAc residues.

The vaccine produced as outlined in the preceding specification can be formulated in a pharmaceutically acceptable carrier, such as phosphate buffered saline, normal saline or other appropriate carrier. Additionally, the vaccine can optimally include one or more adjuvants to augment the immunogenecity and/or efficacy. Adjuvants can be added directly to the vaccine compositions or can be administered separately, either concurrently with or shortly after, administration of the vaccine. Without limitation, suitable adjuvants include a variety of adjuvants known in the art, either alone or in combination. Non-limiting examples are an aluminum salt such as aluminum hydroxide gel or aluminum phosphate or alum, but can also be a salt of calcium, magnesium, iron or zinc, or may be an insoluble suspension of acylated tyrosine, or acylated sugars, cationically or anionically derivatized saccharides, or polyphosphazenes. Adjuvants can also be selected, for example, from a variety of oil in water emulsions, Toll like receptors agonists, (ex Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof.

A vaccine composition yielding a productive antibody response may be used in multiple ways. For example, the vaccine may be used for direct immunization of patients at risk for fungal infection. Alternatively, the compounds and compositions of the present invention may be used to isolate or generate antibodies to the compounds of the invention. Isolated antibodies might be prepared, either polyclonal or monoclonal in nature, using known methods available in the art. For example, the compounds of the invention may be used to screen human antibody phage display libraries, by methods well known to practitioners skilled in the art. As another example, the compositions described herein may be used to elicit an antibody response in an appropriate host and the resulting antibodies may be immortalized by hybridoma technology, using known methods well established in the art. In yet another non-limiting example, using methods known in the art, the compounds described herein may be used to directly produce human antibodies using human B-cell hybridoma technology. Any antibodies thus produced may be used to confer passive protection, either for prophylactic or therapeutic use. Non-limiting examples for uses of these isolated antibodies might include direct protection against fungal disease via immunotherapy, combination therapy with existing anti-fungal agents, or immunoconjugate preparation, eg. direct conjugation to anti-fungal agents. Furthermore, these antibodies can be used to develop a diagnostic platform for detection of fungal infection in patient samples.

In view of the described achievement in producing a vaccine antigen that elicits specific responses to fungal cell wall components, any of the foregoing antibody based strategies could be extended to antibody fragments or engineered antibody derivatives, which can include one or more complementarity determining regions (CDRs) of antibodies, or one or more antigen-binding fragments of an antibody. The terms "antibody" and "antibodies" include, but are not limited to, monoclonal antibodies, multispecific antibodies, human antibodies, humanized antibodies, camelised antibodies, chimeric antibodies, single-chain Fvs (scFv), single chain antibodies, single domain antibodies, Fab fragments, F(ab') fragments, etc., and epitope-binding fragments of any of the above.

A portion of the chitin present in the fungal cell wall is modified by chitin deacetylases to produce chitosan and there is evidence that a mixture of chitin/chitosan polymers may be necessary for proper cell wall integrity and function (19, 20). NMR data on the modified chitin fragments shows some residual free amino groups, raising the possibility that the vaccine can target both pure chitin as well as chitosan containing regions in the chitinous cell wall.

In addition to chitin, β-mannan and β-glucan polymers comprise the fundamental carbohydrate constituents of the fungal cell wall. Vaccine induced antibodies that target specific β-mannan or β-glucan carbohydrates have been shown to confer protection against fungal disease, displaying both vaccine based efficacy and passive protection (9-11). To date, chitin has not been examined as an anti-fungal vaccine target. In vivo, these three carbohydrate components are covalently cross linked to form the cell wall lattice (21, 22). Vaccine formulations consisting of modified chitin alone, or a combination of two or more of the conserved carbohydrate epitopes of the fungal cell wall, are contemplated to produce a broadly protective vaccine response. Such a combination vaccine could be designed either as a co-administered mixture or as a cross linked scaffold that more closely mimics the surface topography of the fungal cell wall. It is anticipated that these vaccines will be highly effective at inducing a pan fungal immune response.

The invention will be better understood by reference to the following examples, which illustrate but do not limit the invention described herein.

EXAMPLES

Example 1: Partial Re-N-Acetylation/Deamination of Chitosan to Yield Modified Chitin Fragments 3 g of chitosan (16.8 mmol of $GlcNH_2$; Sigma cat. #419419) was suspended in 150 mL of $H_2O$ in a 250 mL round bottomed flask and placed on a stir plate.

Acetic anhydride, 795 μL, 0.5 equivalents, relative to the number of amino groups, was added to 15 mL of EtOH.

The acetic anhydride solution was added to the stirring chitosan suspension, dropwise over 30 minutes, via an addition funnel. The reaction became very viscous, but it was still possible to stir the reaction mixture.

The reaction was allowed to proceed for another 30 minutes at room temperature.

18 mL of glacial acetic acid was added to the reaction mixture, giving a pH of ~3.

6 mL of a freshly prepared 5% aqueous solution of $NaNO_2$ was added to the reaction and the mixture was stirred for 1 hour at room temperature. The reaction liberated a substantial amount of gas and became much less viscous during the course of the reaction.

The reaction mixture was neutralized with 16.5 mL of 10 N NaOH.

The sample was dialyzed overnight, against 4 L of 1 M NaCl, in a dialysis membrane with a 7,000 molecular weight cut off. The sample was further dialyzed against 4 changes of 4 L of water at room temperature.

The reaction mixture was centrifuged for 15 minutes at 4,000 RPM to remove the insoluble material, then filtered through 0.45 um syringe filters.

Samples were removed for HPLC and NMR analysis.

Example 2: Preparation of Modified Chitin-Tetanus Toxoid Vaccine Conjugate by Reductive Amination 5 mg of tetanus toxoid (TT, 3.3 mL from 3 mg/mL solution in saline; Serum Staten Institute) was added to 50 mg of modified chitin fragment.

The Schiff Base reaction was allowed to proceed for 6 hours at room temperature.

Repurified sodium cyanoborohydride, 10 mg, was added in a volume of 10 μL, $H_2O$ to the reaction mixture. The reaction was left to proceed at room temperature and monitored after one and three days by SDS-PAGE.

Following the reaction, the chitin-TT mixture was diluted to ~2 mL with PBS and dialyzed against 4 L of PBS. The dialyzed sample was filtered through a 0.45 μm syringe filter. The final dialysate was quantitated by BCA assay and analyzed by SDS-PAGE and HPLC.

Example 3: Immunization of Balb/C Mice with Modified Chitin-TT Vaccine Conjugate 40 female Balb/C mice were received and housed under standard day/night cycles with food and water, ad libitum. The animals were allowed to acclimate to the facility for a minimum of one week, then randomly divided into four groups and immunized as follows:

1. An emulsion of PBS in Freund's Complete Adjuvant (200 μL) was delivered by intraperitoneal injection into 10 mice on day 0. On days 28 and 38, animals received injections of PBS in Freund's Incomplete Adjuvant, delivered in the same manner.
2. Modified Chitin-TT conjugate (25 μg of antigen) was injected into 10 mice as an emulsion in Freund's Complete Adjuvant (200 μL), by intraperitoneal injection on Day 0. On days 28 and 38, animals received booster injections of Chitin-TT (25 μg) in Freund's Incomplete Adjuvant, delivered in the same manner as the primary immunization.
3. Animals were injected with Modified Chitin-TT (50 μg), as per the protocol for Group 2.

4. Animals were injected with Modified Chitin-TT (100 μg), as per Groups 2 & 3.

Mice were bled and serum was prepared on Days −4, 38 and 50 in order to evaluate chitin specific antibody responses.

Animals were bled and serum was prepared 4 days prior to the initial injection (Study Day −4), in order to determine antibody titers in pre-immune serum. Mice were immunized on Study Day 0 according to the experimental groups outlined above. The LMW Chitin-TT antigen was suspended in PBS at concentrations of 0.25, 0.5 and 1.0 mg/mL, mixed with Freund's Complete adjuvant at a 1:1 ratio, and vortexed for 20 minutes to create an emulsion. 200 μL of emulsion containing PBS/Freund's control or the test antigens (final conc. 0.125, 0.25 or 0.5 mg/mL for a total of 25, 50, or 100 μg protein conjugate, respectively) was administered by intraperitoneal injection, as indicated above, to each mouse on Day 0. For the subsequent boosts on Day 28 and Day 38, antigen was prepared similarly in Freund's Incomplete Adjuvant and administered in the same manner. Immunized animals were bled and serum was prepared on Day 38 and Day 50 in order to evaluate antibody responses.

Example 4: Assay for Antibody Response of Balb/C Mice Immunized with Modified Chitin-TT Vaccine Conjugate 2 μg/mL solutions of two different Modified Chitin human serum albumin (HSA) conjugates were prepared in PBS.

100 μL of each solution was coated into half the wells of a 96-well assay plate (½ plate for each antigen) and incubated overnight at room temperature.

The wells were washed 3× with PBST, then blocked for 1 hour with 1% BSA in PBS.

Wells were washed 3× with PBST.

Modified Chitin Vaccine mouse sera were pooled and diluted 1:20 in PBS.

Treatment groups were as follows:

1. PBS/Freund's
2. Modified Chitin-TT/Freund's; 25 μg/mouse
3. Modified Chitin-TT/Freund's; 50 μg/mouse
4. Modified Chitin-TT/Freund's; 100 μg/mouse 200 μL of a ten fold dilution of each pooled serum sample was plated into the first column of wells of the Chitin-HSA coated microplate.

A two fold dilution series was made for a total of 12 different serum concentrations, ranging from 1:200 to 1:409,600.

The samples were incubated for 2 hours at room temperature.

The plate was washed 3× with PBST, then incubated 1 hour at RT with 100 μL of anti-mouse IgG (γ-chain specific)-HRP diluted 1:2500 in 1% BSA/PBST Wells were washed 3× with PBST, then incubated with 100 μL of SureBlue Reserve TMB peroxidase substrate for 5 minutes at room temperature.

The reaction was stopped with 100 μL 1 N HCl.

The absorbance was read on a microplate reader at 450 nm.

Example 5: Assay for Specificity of the Antibody Response of Balb/C Mice Immunized with Modified Chitin-TT Vaccine Conjugate A. Antigen Inhibition 2 μg/mL solutions of modified chitin HSA conjugates (lots #2 and #3) were prepared in PBS.

100 μL of each solution was coated into half the wells of a 96-well assay plate and incubated overnight at room temperature.

The wells were washed 3× with PBST and blocked 1 hour with 1% BSA in PBS.

Wells were washed 3× with PBST and stored dry at 4° C. until use.

2 mg/mL solutions of GlcNAc, HA and modified Chitin fragments were prepared in PBS and 200 μL of each solution was transferred to a set of titer tubes.

A two fold dilution series in PBS was made for a total of 11 different concentrations of each inhibitor, ranging from 2 mg/mL to 1.95 μg/mL, as well as an uninhibited control (final inhibitor concentrations of 1 mg/mL to 976 ng/mL).

Pooled sample from the Modified Chitin-TT/Freund's treatment group (100 μg/mouse, Day 50 bleed) was diluted to 20:000 fold in 1% BSA/PBST.

100 μL of diluted serum sample was transferred into each of the titer tubes (final 40:000 dilution) and incubated with the inhibitors for 30 minutes at room temperature.

100 μL of each serum sample/inhibitor was transferred into the Modified Chitin-HSA coated microplate and incubated for 2 hours at room temperature.

The plate was washed 3× with PBST, then incubated 1 hour at RT with 100 μL of anti-mouse IgG (γ-chain specific)-HRP diluted 1:2500 in 1% BSA/PBST Wells were washed 3× with PBST, then incubated with 100 μL of SureBlue Reserve TMB peroxidase substrate for 5 minutes at room temperature.

The reaction was stopped with 100 μL 1 N HCl and the absorbance was read on a microplate reader at 450 nm.

B. Antibody Reactivity Specificity Controls

2 μg/mL solutions of the test compounds (serine-O-GlcNAc, ovalbumin, fetuin, hyaluronic acid (HA), fetal bovine serum) were prepared in PBS, with the exception of FBS, which was prepared as a 10% solution (v:v) in PBS.

100 μL of each solution was coated into the wells of a 96-well assay plate. The test antigens were incubated in the plate overnight at 4° C.

The wells were washed 3× with PBS and blocked for 1 hour with 1% BSA/PBS.

Wells were washed 3× with PBST and stored dry at 4° C. until use.

Modified Chitin Vaccine mouse sera were pooled by treatment group and diluted 1:20 in PBS Treatment groups were as follows:

1. PBS/Freund's
2. Modified Chitin-TT/Freund's; 25 μg/mouse
3. Modified Chitin-TT/Freund's; 50 μg/mouse
4. Modified Chitin-TT/Freund's; 100 μg/mouse The pooled serum samples were further diluted to a final of 1:20,000 fold in 1% BSA/PBST.

100 μL of diluted serum sample from each group was transferred in triplicate to the wells of the assay plate and incubated for 1 hour at room temperature.

The plate was washed 3× with PBST, then incubated 1 hour at RT with 100 μL L of anti-mouse IgG (γ-chain specific)-HRP diluted 1:2500 in 1% BSA/PBST Wells were washed 3× with PBST, then incubated with 100 μL of SureBlue Reserve TMB peroxidase substrate for 5 minutes at room temperature.
The reaction was stopped with 100 μL 1 N HCl.
The absorbance was read on a plate reader at 450 nm.
Note that the ELISA response for all of the replicates for Group 4 were out of the linear range. These samples were arbitrarily assigned a value of 3.0, which is near the detection limit of the plate reader. These values probably represent an underestimate.
C. Chitin/Chitosan Absorption and Inhibition
2 μg/mL solutions of the test compounds (modified chitin-HSA or LMW HA-HSA) were prepared in PBS.
100 μL of each solution was coated into the wells of a 96-well assay plate and incubated overnight at 4° C.
The wells were washed 3× with PBST and blocked for 1 hour with 1% BSA in PBS.
Wells were washed 3× with PBST.
In the meantime, pooled Modified Chitin Vaccine mouse sera was diluted to a final concentration of 1:5000 in 1% BSA/PBS.
HA MAb #2 was diluted to 1:2000 in 1% BSA/PBS.
5 mL of diluted serum sample or HA MAb was incubated overnight on a rotator at 4° C. with 100 mg of either chitin or chitosan (both made as insoluble suspensions).
A fraction of diluted chitin vaccine #1 serum or HA MAb was set aside at 4° C. to serve as positive controls and to mix with chitin/chitosan extracts for inhibition experiment.
In parallel, chitin and chitosan was incubated with 5 mL of 1% BSA/PBS in the same manner, in order to extract soluble chitin/chitosan for inhibition testing.
Samples were centrifuged 5 minutes at 4500 to pellet out insoluble chitin and chitosan.
The supernatant fractions were removed to fresh tubes and diluted 4 fold (final 1:20,000 for Modified Chitin Vaccine and 1:8,000 for HA MAb) in 1% BSA/PBS.
Untreated Modified Chitin vaccine serum sample and untreated HA MAb were likewise diluted to equivalent final concentrations in 1% BSA/PBS (100 μL Ab or serum+300 μL BSA/PBS)
For inhibition testing, untreated serum or Ab solutions were diluted 4 fold with either chitin or chitosan extract to equivalent final concentrations (final 1:20,000 for Modified Chitin Vaccine and 1:8,000 for HA MAb). The solutions were pre-incubated for 30 minutes at room temperature prior to addition to the ELISA plate.
100 μL of each sample was added, in triplicate, to ELISA strips coated with either modified Modified Chitin-HSA or LMW HA-HSA, as appropriate.
The samples were incubated in the strips for one hour at room temperature.
The strips were washed 3× with PBST, then incubated 1 hour at RT with 100 μL of anti-mouse IgG (γ-chain specific)-HRP, diluted 1:2500 in 1% BSA/PBST.
Wells were washed 3× with PBST, then incubated with 100 μL of SureBlue Reserve TMB peroxidase substrate for 5 minutes at room temperature.
The reaction was stopped with 100 μL 1 N HCl.
The HA ELISA samples developed color very rapidly, so the reaction was stopped within ~1 minute. Likewise, the positive control in the Modified Chitin Vaccine samples developed rapidly, so the reaction was terminated after 2 minutes.

The absorbance was read on a microplate reader at 450 nm.

Example 6: Assays for Immunoreactivity of Serum Antibodies from Modified Chitin-TT Vaccine Immunized Balb/C Mice Toward *C. albicans* Whole Cells A. Binding of Whole Serum to *C. albicans* Cells
A single colony of *C. albicans* was picked from a Saboraud Dextrose Agar plate and used to inoculate 2 mL of YPD growth medium. The culture was grown overnight at 30° C., with shaking at 250 RPM.
100 μL of a $5\times10^6$ cells/mL suspension was added into each well of an amine surface modified Strip Well microplate. The cells were allowed to settle for one hour at room temperature.
100 μL of a 2% solution of glutaraldehyde in PBS was added to each well.
The cells were allowed to cross link overnight at room temperature.
The fixative was aspirated away and the wells were washed 3× with PBST.
Wells were blocked for 1 hour at room temp with 1% BSA in PBS.
In the meantime, pooled Modified Chitin Vaccine mouse sera were diluted to a concentration of 1:20,000 in 1% BSA/PBS.
100 μL of 2 mg/mL solutions of modified chitin or PBS were distributed, in triplicate, into titer tubes.
For inhibition testing, 100 μL of serum was added to the tubes containing the inhibitors (final 1:40,000 for Modified Chitin Vaccine serum samples and 1 mg/mL for inhibitors). The solutions were pre-incubated for 30 minutes at room temperature prior to addition to the ELISA plate.
100 μL of each sample was added to the *C. albicans* coated stripwell plate. The samples were incubated for one hour at room temperature.
The strips were washed 3× with PBST, then incubated 1 hour at RT with 100 μL of anti-mouse IgG (γ-chain specific)-HRP, diluted 1:2500 in 1% BSA/PBST.
Wells were washed 3× with PBST, then incubated with 100 μL of SureBlue Reserve TMB peroxidase substrate at room temperature.
The reaction was stopped after two minutes with 100 μL 1 N HCl.
The absorbance was read on a plate reader at 450 nm.
B. Binding of Affinity Purified Modified Chitin Reactive Antibodies to *C. albicans*
20 mg of modified chitin and periodate oxidized HA were dissolved in 2 mL of 20 mM $NaPO_4$, pH 7.5. Oxidized HA required overnight at room temperature to dissolve.
UltraLink Hydrazide gel (4 mL of slurry, 2 mL of settled resin) was washed with 5 volumes of 20 mM $NaPO_4$, pH 7.5.
The dissolved saccharides were added to the washed resin and allowed to react for 24 hours at room temperature.
The unbound material was drained away and the resins were washed with the following:
1. 20 column volumes of 20 mM $NaPO_4$, pH 7.5
2. 5 column volumes of 10×PBS.
3. 10 column volumes of 1×PBS.

Pooled Modified Chitin Vaccine mouse sera (from PBS control group and 100 μg modified chitin-TT immunized group) were diluted to an initial concentration of 1:40 in 1% BSA/PBS 100 μL (200 μL of slurry) of Modified Chitin and oxidized HA UltraLink hydrazide gels were washed with 500 μL of PBS in a micro spin column.

200 μL of each serum and the affinity resins were mixed and incubated for 1 hr at RT.

The unbound material was removed by centrifugation for 30 seconds at 8500 RPM.

The resins were washed 3× with 500 μL PBST.

200 μL of 0.2 M glycine, pH 2.8 was added to each resin and allowed to interact for ~3 min.

Eluted protein was collected by centrifugation directly into a tube containing 50 μL of 1 M Tris, pH 8.

A single colony of *C. albicans* was picked from a Sabouraud Dextrose Agar plate and used to inoculate 2 mL of YPD growth medium and the culture was grown overnight at 30° C., with shaking at 250 RPM.

100 μL of $1\times10^7$ cells/mL suspension was added into each well of an amine surface modified Strip Well microplate. The cells were allowed to settle for 2 hours at room temperature.

100 μL of a 2% solution of glutaraldehyde in PBS was added to each well.

The cells were allowed to cross link for one hour at room temperature.

The fixative was carefully aspirated away and the wells were washed 3× with PBST.

Wells were blocked for 1 hour at room temp with 1% BSA in PBS.

The antigen affinity purified antibodies were diluted 1:1, 000 with 1% BSA in PBS.

A 2 fold dilution series was prepared in titer tubes.

100 μL of the antibody dilutions were added in triplicate to the *C. albicans* coated plate.

The samples were incubated for 1 hour at room temperature.

The plate was washed 3× with PBST, then incubated 1 hour at RT with 100 μL of anti-mouse IgG (γ-chain specific)-HRP, diluted 1:2500 in 1% BSA/PBST.

Wells were washed 3× with PBST, then incubated with 100 μL of SureBlue Reserve TMB peroxidase substrate for 5 minutes at room temperature.

The reaction was stopped with 100 μL 1 N HCl.

The absorbance was read on a plate reader at 450 nm.

C. Binding of Vaccine-Induced Antibodies to *Candida albicans* by Flow Cytometry:

*Candida* Cells:

Using a sterile loop, *C. albicans* from frozen stock were streaked on an SDA plate and incubated at 30 C. A single colony from the SDA plate was picked using inoculating loop and inoculated into a 250-ml flask containing 50 ml of YPD and incubated at 30 C with shaking at 150 rpm for at least 18 h. For experiments where mycelia stage of *candida* was used, the cells were incubated at 37 C for 150 minutes and 300 minutes in YPD containing serum following 0/N incubation to induce and favor differentiation into mycelia stage of *candida*. The O/N culture was transferred into a 50 ml tube and centrifuged at 1000 g for 20 mins and the pellet was washed with 2 ml PBS solution at least 3 times. The pellet was resuspended in 2 ml PBS and the concentration was adjusted to 0.1 OD600 (4×106/ml).

Cryptococcal Cells:

Fungal growth-streaking from stock overnight was performed using a sterile loop, and streaking the strain *Cryptococcus neoformans* type A frozen stock to isolation on an SDA plate and incubated at 30° C. A single colony from the SDA plate was picked using inoculating loop and inoculated into a 250-ml flask containing 50 ml of YPD and incubated at 30 C with shaking at 150 rpm for at least 18 h. For experiments where mycelia stage of *Cryptococcus* was used, the cells were incubated at 37 C for 150 minutes and 300 minutes in YPD containing serum following O/N incubation to induce and favor differentiation into mycelia stage of *candida*. The O/N culture was transferred into a 50 ml tube and centrifuged at 1000 g for 20 mins and the pellet was washed with 2 ml PBS solution at least 3 times. The pellet was resuspended in 2 ml PBS and the concentration was adjusted to 1.0 OD600 reading (4×10 7/ml).

Sera and Antibodies:

Mice sera from various vaccine groups was diluted in 1:10, 1:50 and 1:100 in PBS and used at 15 ul volume/tube. The control antibodies were diluted as: Mouse mAb to *candida,* 1:5, 1:10 and 1:20 dilutions; For Rabbit pAb to *candida,* 1:50, 1:100 and 1:200 dilutions and used at 20 ul volume/tube. FITC-labeled secondary antibodies were diluted 1:25 in PBS and used at 15 ul/tube. Propidium Iodide was used at 1:2 in PBS (5 ul/tube).

Flow Cytometry:

About 100 ul of fungal cells were transferred into the tubes and appropriate serum and antibodies were added and incubated on ice for 60 minutes. The cells were then washed 2 times with 1 ml PBS (By spinning at 1000 g for 10 mins at 40 C, decanting supernatant) followed by incubation with secondary antibody for 30 mins on ice protected from light.

Diluted propidium iodide (No Wash) was added and the cells incubated for an additional 10 mins on ice followed by 2 PBS washes and finally fixed in 200 ul of 1% paraformaldehyde. The data was then acquired on a FACS Calibur instrument.

Example 7: Modified Chitin-TT Vaccine Confers Protection from a Lethal Challenge of *C. albicans* Pathogenic Fungus A. Immunization of Balb/C Mice with Modified Chitin-TT Vaccine, and CD1 Mice with Chitoheaose-TT and Laminarin-TT Conjugates.

40 female mice were received and housed under standard day/night cycles with food and water, ad libitum. The animals were allowed to acclimate to the facility for a minimum of one week, then randomly divided into two groups and immunized as follows:

Initially, BalB/c mice were divided into two groups, n=20 mice/group:

1. PBS/Freund's; 200 μL/mouse; intraperitoneal injection
2. Mod Chitin-TT/Freund's; 200 μL/mouse; i.p.; 100 μg/mouse For the mock immunized control animals, an emulsion of PBS in Complete Freund's Adjuvant (200 μL) was delivered by intraperitoneal injection into 20 mice on day 0. On days 28 and 38, animals received injections of PBS in Incomplete Freund's Adjuvant, delivered in the same manner as the primary immunization.

For the vaccination group, Modified Chitin-TT conjugate (100 μg of antigen, as an emulsion in Complete Freund's Adjuvant) was delivered by intraperitoneal injection into 20 mice (200 μL), on Day 0. On days 28 and 38, animals received booster injections of Chitin-TT (50 μg) in Incomplete Freund's Adjuvant, delivered in the same manner as the primary immunization.

Mice were bled and serum was prepared on Days −4, 38, 50, and 62, for evaluation of antibody responses.

Same protocol was used to immunize CD1 mice with modified chitin-TT; laminarin-TT and Chitohexaose-TT conjugates B. Challenge of Chitin-TT Vaccine Immunized Balb/C and CD1 Mice with a Lethal Dose of *C. albicans*

The animals from each of the immunization groups, above, were randomly divided into three groups of ten for each immunization cohort, and inoculated with *C. albicans* cells, as follows.

Experimental groups: n=10 mice/group, randomly divided into groups

Groups 1 and 2 comprise animals from PBS (mock) immunized animals

1. Saline; 200 mouse; tail vein injection
2. $5\times10^6$ *C. albicans;* 200 μL from $2.5\times10^7$ CFU/mL; tail vein injection Groups 3 and 4 comprise animals from modified chitin TT immunized animals
3. Saline; 200 μL/mouse; tail vein injection
4. $5\times10^6$ *C. albicans;* 200 μL from $2.5\times10^7$ CFU/mL; tail vein injection Monitoring mice:

1. Mice were checked daily for mortality and signs of distress: Decreased food and water consumption, weight loss, self-imposed isolation/hiding, rapid breathing, opened-mouthbreathing, increased/decreased movement, abnormal posture/positioning, dehydration, twitching, trembling, and tremors.
2. Mice showing signs of distress accompanied by any of the following were defined as moribund: impaired ambulation (unable to reach food and water), evidence of muscle atrophy or signs of emaciation, lethargy (drowsiness, aversion to activity, lack of physical or mental alertness), prolonged anorexia, difficulty breathing, and neurological disturbances. Mice were euthanized when they look moribund and death appeared imminent. The date of death was recorded as the following day.

Example 8: Detection and Characterization of Chitin and β-Glucan Antibodies in Human Normal Sera 2 μg/mL solutions of different human serum albumin (HSA) conjugates (modified chitin, chitohexaose, and laminarin) were prepared in PBS.

100 μL of each solution was coated into half the wells of a 96-well assay plate (½ plate for each antigen) and incubated overnight at room temperature.

The wells were washed 3× with PBST, then blocked for 1 hour with 1% BSA in PBS.

Wells were washed 3× with PBST.

Normal human sera diluted 1:20 in PBS.

200 μL of a ten fold dilution of each pooled serum sample was plated into the first column of wells of the various HSA conjugates coated microplate.

A two fold dilution series was made for a total of 12 different serum concentrations, ranging from 1:200 to 1:409,600.

The samples were incubated for 2 hours at room temperature.

The plate was washed 3× with PBST, then incubated 1 hour at RT with 100 (0.1 L of anti-human IgG (γ-chain specific)-HRP diluted 1:2500 in 1% BSA/PBST Wells were washed 3× with PBST, then incubated with 100 (0.1 L of SureBlue Reserve TMB peroxidase substrate for 5 minutes at room temperature.

The reaction was stopped with 100 μL 1 N HCl.

The absorbance was read on a microplate reader at 450 nm.

Example 9: Preparation of a β1,3 Glucan/Chitin Conjugate Tetanus Toxoid Vaccine Following is an example of one of several envisioned methods to prepare a combination fungal vaccine comprising two or more conserved components of the fungal cell wall. In this example, laminarin (linear, unbranched polymer of β-1,3 glucan) was reduced and oxidized with sodium periodate, subsequently conjugated directly to chitosan via reductive amination, and finally, the cross linked carbohydrates were conjugated to tetanus toxoid.

Laminarin was reduced with sodium borohydride and subsequently oxidized with sodium meta periodate by standard methods.

100 mg of oxidized laminarin was dissolved in PBS (several minutes at 37° C. to dissolve) and mixed with low molecular weight chitosan at a 1:5 ratio. The chitosan remained as an insoluble suspension.

The reaction was placed in a 37° C. shaking incubator for 24 hours.

20 mg of $NaCNBH_3$ was added and the reaction was continued another 24 hours at 37° C.

The reaction suspension was transferred to a disposable plastic column and the insoluble material was washed extensively with $H_2O$ to remove any residual, unreacted laminarin.

The washed, insoluble material was resuspended in 5 mL of 10% aqueous acetic acid 1 mL of freshly prepared aqueous sodium nitrite was added and the reaction was allowed to proceed for 60 minutes at room temperature. Most of the insoluble material entered into solution during the course of the reaction.

The reaction mixture was centrifuged 5 minutes at 4500×G to remove the remaining insoluble material. The soluble fraction was further processed as described below.

The soluble fraction was diluted to 15 mL, in a final concentration of 1 M NaCl and dialyzed against 4 changes of 4 liters of $H_2O$. The dialyzed material was lyophilized to give a fluffy white powder, 90 mg total yield.

The polysaccharide conjugate was analyzed by SEC HPLC and the presence of both chitin and β-glucan in the product was confirmed by $^1H$ NMR.

10 mg of tetanus toxoid (TT, 3.3 mL from 3 mg/mL solution in saline) was added to 40 mg of the laminarin-chitin conjugate.

A 2 μL aliquot of the sample was added to 98 μL of 1×LDS sample buffer+5 μL of 1 M DTT for SDS-PAGE analysis.

Another 2 μL of sample was added to 98 μL of 1×PBS for HPLC analysis.

The solution was allowed to react for 24 hours at 37° C. in a shaking incubator (300 RPM).

Repurified sodium cyanoborohydride, 40 mg, was added directly to the reaction. The reactions were left to proceed for 24 hours at 37° C. in a shaking incubator (300 RPM).

Following the reaction, the conjugation reaction was concentrated to ~2.5 mL in an Amicon ultrafiltration device with a 10,000 MWCO membrane. The sample was dialyzed against 3 exchanges of 4 L of PBS. The final dialysate was quantitated by BCA assay and analyzed by SDS-PAGE and SEC HPLC. After the samples were adjusted to a concentration of 1 mg/mL, they were sterile filtered through a 0.22 micron filter.

LITERATURE REFERENCES

1. De Jonge R, van Esse H P, Kombrink A, Shinya T, Desaki Y, Bours R, van der Krol S, Shibuya N, Joosten M H, Thomma B P. 2010. Conserved fungal LysM effector Ecp6 prevents chitin-triggered immunity in plants. *Science* 329: 953-5
2. Lee C G. 2009. Chitin, chitinases and chitinase-like proteins in allergic inflammation and tissue remodeling. *Yonsei Med J* 50: 22-30
3. Cutler J E, Deepe G S, Jr., Klein B S. 2007. Advances in combating fungal diseases: vaccines on the threshold. *Nat Rev Microbiol* 5: 13-28
4. Ostrosky-Zeichner L, Casadevall A, Galgiani J N, Odds F C, Rex J H. 2010. An insight into the antifungal pipeline: selected new molecules and beyond. *Nat Rev Drug Discov* 9: 719-27
5. Pfaller M A, Diekema D J. 2007. Epidemiology of invasive candidiasis: a persistent public health problem. *Clin Microbiol Rev* 20: 133-63
6. Casadevall A, Pirofski L A. 2007. Antibody-mediated protection through cross-reactivity introduces a fungal heresy into immunological dogma. *Infect Immun* 75: 5074-8
7. Spellberg B. 2007. Prospects for and barriers to a fungal vaccine. *Expert Opin Biol Ther* 7: 1785-8
8. Cassone A, Torosantucci A. 2006. Opportunistic fungi and fungal infections: the challenge of a single, general antifungal vaccine. *Expert Rev Vaccines* 5: 859-67
9. Torosantucci A, Bromuro C, Chiani P, De Bernardis F, Berti F, Galli C, Norelli F, Bellucci C, Polonelli L, Costantino P, Rappuoli R, Cassone A. 2005. A novel glyco-conjugate vaccine against fungal pathogens. *J Exp Med* 202: 597-606
10. Xin H, Dziadek S, Bundle D R, Cutler J E. 2008. Synthetic glycopeptide vaccines combining beta-mannan and peptide epitopes induce protection against candidiasis. *Proc Natl Acad Sci USA* 105: 13526-31
11. Han Y, Cutler J E. 1995. Antibody response that protects against disseminated candidiasis. *Infect Immun* 63: 2714-9
12. Rachini A, Pietrella D, Lupo P, Torosantucci A, Chiani P, Bromuro C, Proietti C, Bistoni F, Cassone A, Vecchiarelli A. 2007. An anti-beta-glucan monoclonal antibody inhibits growth and capsule formation of *Cryptococcus neoformans* in vitro and exerts therapeutic, anticryptococcal activity in vivo. *Infect Immun* 75: 5085-94
13. Torosantucci A, Chiani P, Bromuro C, De Bernardis F, Palma A S, Liu Y, Mignogna G, Maras B, Colone M, Stringaro A, Zamboni S, Feizi T, Cassone A. 2009. Protection by anti-beta-glucan antibodies is associated with restricted beta-1,3 glucan binding specificity and inhibition of fungal growth and adherence. *PLoS One* 4: e5392
14. Bromuro C, Torosantucci A, Chiani P, Conti S, Polonelli L, Cassone A. 2002. Interplay between protective and inhibitory antibodies dictates the outcome of experimentally disseminated Candidiasis in recipients of a *Candida albicans* vaccine. *Infect Immun* 70: 5462-70
15. Bredehorst R, Pomato N, Scheel O, Thiem J. 1998. U.S. Pat. No. 5,705,634A
16. Nakao E. 1994. U.S. Pat. No. 5,312,908
17. Nishimura T, Eto E, Yamad T. 1989. U.S. Pat. No. 4,804,750A
18. Gislason J, Einarsson J M, How N C, Bahrke S. 2009. Patent No. US20090281058A1
19. Lenardon M D, Munro C A, Gow N A. 2010. Chitin synthesis and fungal pathogenesis. *Curr Opin Microbiol* 13: 416-23
20. Baker L G, Specht C A, Donlin M J, Lodge J K. 2007. Chitosan, the deacetylated form of chitin, is necessary for cell wall integrity in *Cryptococcus neoformans. Eukaryot Cell* 6: 855-67
21. Latge J P. 2007. The cell wall: a carbohydrate armour for the fungal cell. *Mol Microbiol* 66: 279-90
22. Levitz S M. 2010. Innate recognition of fungal cell walls. *PLoS Pathog* 6: e1000758
23. Nitz M, Bundle D. R. 2001. J. Synthesis of Di- to Hexasaccharide 1,2-Linked-Mannopyranan Oligomers, a Terminal S-Linked Tetrasaccharide Congener and the Corresponding BSA Glycoconjugates *J Org Chem* 66: 8411-2324. Antinori S, 2013. New Insights into HIV/AIDS-Associated Cryptococcosis. ISRN AIDS 471363
25. Rappleye C A, Eissenberg L G, Goldman W E. 2007. *Histoplasma capsulatum* alpha-(1,3)-glucan blocks innate immune recognition by the beta-glucan receptor. *PNAS.* 104(4):1366-70
26. Fujikawa T. et al. 2012. Surface alpha 1,3-Glucan Facilitates Fungal Stealth Infection by Interfering with Innate Immunity in Plants *PLOS Pathogens* 8:|e1002882
27. Reese, A. J. et al. 2007. Loss of cell wall alpha (1-3) glucan affects *Cryptococcus neoformans* from ultrastructure to virulence. *Mol. Microbiol.* 63, 1385-1398.

What is claimed is:

1. A compound comprising one or more polysaccharide moieties each independently represented by the formula, $\beta(1\rightarrow4)$-[GlcNH—R]$_n$-2,5-anhydromannose wherein n is a positive integer from 3 to 500, and R is H or an acyl group, and the one or more polysaccharide moieties are chitin/chitosan mixed polymers, and an immunogenic carrier protein selected from the group consisting of tetanus toxoid, diphtheria toxoid, and a fungal protein virulence factor covalently linked to the one or more polysaccharide moieties at the anhydromannose group of the polysaccharide moieties.

2. The compound of claim 1, wherein n is a positive integer from 3 to 100.

3. The compound of claim 2, wherein n is a positive integer from 6 to 50.

4. The compound of claim 1, wherein the acyl group R is an acetyl group.

5. The compound of claim 1, wherein at least 30% of the acyl groups in the compound are acetyl.

6. The compound of claim 1, further comprising one or more linear β-mannan or glucan epitopes covalently linked to the carrier protein.

7. The compound of claim 6, wherein the β-mannan is a β-1,2-mannose tetrasaccharide.

8. The compound of claim 6, wherein one of the one or more glucan epitopes is a linear α-1,3-glucan epitope.

9. The compound of claim 6, wherein one of the one or more glucan epitopes is a linear β-1,3-glucan epitope.

10. The compound of claim 1, wherein the carrier protein is covalently linked to the one or more polysaccharide moieties via one or more immunogenic scaffold moieties.

11. The compound of claim 10, wherein each of the scaffold moieties is selected from the group consisting of a polysaccharide, a peptidoglycan, a polypeptide, and a polyglycerol.

12. The compound of claim 10, wherein the scaffold is linear.

13. The compound of claim 10, wherein the scaffold is dendrimeric.

14. The compound of claim 10, further comprising one or more linear β-mannan or glucan epitopes covalently linked to the carrier protein or the scaffold.

15. The compound of claim 14, wherein the β-mannan is a β-1,2-mannose tetrasaccharide.

16. The compound of claim 14, wherein one of the one or more glucan epitopes is a linear α-1,3-glucan epitope.

17. The compound of claim 14, wherein one of the one or more glucan epitopes is a linear β-1,3-glucan epitope.

18. A composition comprising the compound of claim 1, wherein for at least 80% of molecules of the compound in the composition n has a value from 6 to 50.

19. A composition comprising the compound of claim 1, wherein the mean value of n is from 10 to 50.

* * * * *